(12) United States Patent
Zigelboim et al.

(10) Patent No.: US 10,905,540 B2
(45) Date of Patent: Feb. 2, 2021

(54) STENT-GRAFTS SYSTEMS WITH SKIRT

(71) Applicant: ENDOSPAN LTD., Pituach (IL)

(72) Inventors: Or Zigelboim, Giv'atayim (IL); Yaniv Marmur, Yokneam Moshava (IL); Alon Shalev, Ra'anana (IL)

(73) Assignee: ENDOSPAN LTD., Pituach (IL)

( * ) Notice: Subject to any disclaimer, the term of this patent is extended or adjusted under 35 U.S.C. 154(b) by 101 days.

(21) Appl. No.: 15/775,418

(22) PCT Filed: Nov. 9, 2016

(86) PCT No.: PCT/IL2016/051207
§ 371 (c)(1),
(2) Date: May 11, 2018

(87) PCT Pub. No.: WO2017/081679
PCT Pub. Date: May 18, 2017

(65) Prior Publication Data
US 2018/0333251 A1 Nov. 22, 2018

Related U.S. Application Data

(60) Provisional application No. 62/371,983, filed on Aug. 8, 2016, provisional application No. 62/254,432, filed on Nov. 12, 2015.

(51) Int. Cl.
*A61F 2/07* (2013.01)
*A61F 2/962* (2013.01)
*A61F 2/06* (2013.01)

(52) U.S. Cl.
CPC ............... *A61F 2/07* (2013.01); *A61F 2/962* (2013.01); *A61F 2002/061* (2013.01);
(Continued)

(58) Field of Classification Search
CPC .... A61F 2/07; A61F 2/06; A61F 2/064; A61F 2/24; A61F 2/962; A61F 2/2418;
(Continued)

(56) References Cited

U.S. PATENT DOCUMENTS 5,129,910 A 7/1992 Phan et al.
5,632,772 A 5/1997 Alcime et al.
(Continued)

FOREIGN PATENT DOCUMENTS

EP 1621159 2/2006
EP 1779809 5/2007
(Continued)

OTHER PUBLICATIONS

European Search Report dated Mar. 15, 2017 which issued during the prosecution of Applicant's European App No. 10791726.2.
(Continued)

*Primary Examiner* — Ashley L Fishback
(74) *Attorney, Agent, or Firm* — Sughrue Mion, PLLC

(57) ABSTRACT

An endovascular prosthesis includes a stent-graft and an external coagulation inducer. The stent-graft includes a first portion of structural strut members and a first portion of a graft member, which, when the endovascular prosthesis is unconstrained, in a radially-expanded state, together are shaped so as to define a blood-carrying tubular structure defining a lumen. The external coagulation inducer includes an extra-luminal skirt, which includes a second portion of the structural strut members and a second portion of the graft member, and is configured to assume: (i) when the endovascular prosthesis is removably disposed in a delivery sheath, a radially-compressed delivery state, in which the structural strut members of the first portion do not coincide with the structural stent members of the second portion, and (ii) when the endovascular prosthesis is unconstrained, a (Continued)

radially-expanded state, in which the extra-luminal skirt extends radially outward from an external surface of the stent-graft.

18 Claims, 27 Drawing Sheets

(52) U.S. Cl.
CPC ... *A61F 2002/065* (2013.01); *A61F 2002/075* (2013.01); *A61F 2002/077* (2013.01); *A61F 2210/0014* (2013.01); *A61F 2210/0076* (2013.01); *A61F 2230/0006* (2013.01); *A61F 2230/0013* (2013.01); *A61F 2230/0019* (2013.01); *A61F 2230/0054* (2013.01); *A61F 2230/0069* (2013.01); *A61F 2230/0084* (2013.01); *A61F 2230/0091* (2013.01); *A61F 2230/0093* (2013.01); *A61F 2250/0039* (2013.01)

(58) Field of Classification Search
CPC .......... A61F 2002/061; A61F 2002/065; A61F 2002/075; A61F 2002/077; A61F 2002/068; A61F 2250/0039; A61F 2210/0014; A61F 2210/0076; A61B 2017/1107
See application file for complete search history.

(56) References Cited

U.S. PATENT DOCUMENTS

| | | | |
|---|---|---|---|
| 5,676,696 | A | 10/1997 | Marcade |
| 5,944,750 | A | 8/1999 | Tanner et al. |
| 6,015,431 | A | 1/2000 | Thornton et al. |
| 6,030,415 | A | 2/2000 | Chuter |
| 6,149,682 | A | 11/2000 | Frid |
| 6,395,018 | B1 | 5/2002 | Castaneda |
| 6,451,048 | B1 | 9/2002 | Berg et al. |
| 6,645,242 | B1 | 11/2003 | Quinn |
| 6,729,356 | B1 | 5/2004 | Baker et al. |
| 6,964,679 | B1 | 11/2005 | Marcade et al. |
| 7,044,962 | B2 | 5/2006 | Elliott |
| 7,112,217 | B1 | 9/2006 | Kugler et al. |
| 7,122,052 | B2 | 10/2006 | Greenhalgh |
| 7,135,037 | B1 | 11/2006 | Chuter et al. |
| 7,144,421 | B2 | 12/2006 | Carpenter et al. |
| 7,226,474 | B2 | 6/2007 | Iancea et al. |
| 7,413,573 | B2 | 8/2008 | Hartley et al. |
| 7,628,803 | B2 | 12/2009 | Pavcnik et al. |
| 8,221,494 | B2 | 7/2012 | Schreck et al. |
| 8,287,586 | B2 | 10/2012 | Schaeffer et al. |
| 8,333,800 | B2 | 12/2012 | Bruszewski et al. |
| 2001/0044647 | A1 | 11/2001 | Pinchuk et al. |
| 2001/0047198 | A1 | 11/2001 | Drasler |
| 2002/0052643 | A1 | 5/2002 | Wholey et al. |
| 2002/0052644 | A1 | 5/2002 | Shaolian et al. |
| 2002/0147490 | A1* | 10/2002 | Pletzer ............... A61F 2/06 623/1.11 |
| 2003/0204242 | A1 | 10/2003 | Zarins et al. |
| 2003/0208192 | A1 | 11/2003 | Truckai et al. |
| 2004/0117003 | A1 | 6/2004 | Ouriel et al. |
| 2005/0059923 | A1 | 3/2005 | Gamboa |
| 2006/0100684 | A1 | 5/2006 | Elliott |
| 2006/0271166 | A1 | 11/2006 | Thill et al. |
| 2007/0073373 | A1 | 3/2007 | Bonsignore |
| 2008/0015682 | A1 | 1/2008 | Majercak et al. |
| 2008/0195191 | A1 | 8/2008 | Luo et al. |
| 2008/0275540 | A1 | 11/2008 | Wen |
| 2009/0171437 | A1 | 7/2009 | Brocker et al. |
| 2009/0287145 | A1 | 11/2009 | Cragg et al. |
| 2012/0143317 | A1 | 6/2012 | Cam et al. |
| 2012/0150274 | A1 | 6/2012 | Shalev et al. |

FOREIGN PATENT DOCUMENTS

| | | |
|---|---|---|
| EP | 2085050 | 8/2009 |
| WO | 00/42949 | 7/2000 |
| WO | 2006/088905 | 8/2006 |
| WO | 2007/144782 | 12/2007 |
| WO | 2008/140796 | 11/2008 |
| WO | 2014/197743 | 12/2014 |

OTHER PUBLICATIONS

Aortic Aneurysm O'Gara, Patrick T. Circulation. 2003; 107:e43-e45.
U.S. Appl. No. 62/371,983, filed Aug. 8, 2016.
An International Search Report and a Written Opinion both dated Jan. 19, 2017, which issued during the prosecution of Applicant's PCT/IL2016/051207.
An Office Action dated Apr. 24, 2014, which issued during the prosecution of Applicant's U.S. Appl. No. 13/380,278.
An Office Action dated Jan. 12, 2017, which issued during the prosecution of U.S. Appl. No. 14/518,542.
An International Search Report dated Feb. 4, 2011, which issued during the prosecution of Applicant's PCT/IB2010/052861.
A Written Opinion dated Feb. 4, 2011, which issued during the prosecution of Applicant's PCT/IB2010/052861.
U.S. Appl. No. 62/254,432, filed Nov. 12, 2015.
Communication Article dated Feb. 28, 2018, which issued during the prosecution of European Patent Application No. 10791726.2.
Maldonado TS et al., "Initial successful management of type I endoleak after endovascular aortic aneurysm repair with n/butyl cyanoacrylate adhesive," Journal of Vascular Surgery, vol. 38, Issue 4, pp. 664-670, Oct. 2003.
Bruen KJ et al., "Endovascular chimney technique versus open repair of juxtarenal and suprarenal aneurysms," Journal of Vascular Surgery, vol. 53, Issue 4, pp. 895-905, Apr. 2011.
Lee WA, "An assessment of snorkels, chimneys, sandwich grafts and fenestrations," UCSF Vascular Symposium 2012, Apr. 26, 2012.
Rancic Z et al., "Periscope graft to extend distal landing zone in ruptured thoracoabdominal aneurysms with short distal necks," Journal of Vascular Surgery, vol. 51, Issue 5, pp. 1293-1296, May 2010.
Scali ST et al., "Critical analysis of results after chimney EVAR raises cause for concern," J Vasc Surg Oct. 2014 ; 60(4): 865-874.
An Office Action dated Mar. 8, 2019, which issued during the prosecution of Canadian Patent Application No. 3009244.
European Search Report dated Oct. 17, 2018 which issued during the prosecution of Applicant's European App No. 18195339.9.
An International Search Report and a Written Opinion both dated May 23, 2018, which issued during the prosecution of Applicant's PCT/IL2018/050325.
A non-final Office Action issued in U.S. Appl. No. 15/894,539, dated Jan. 27, 2020.

* cited by examiner

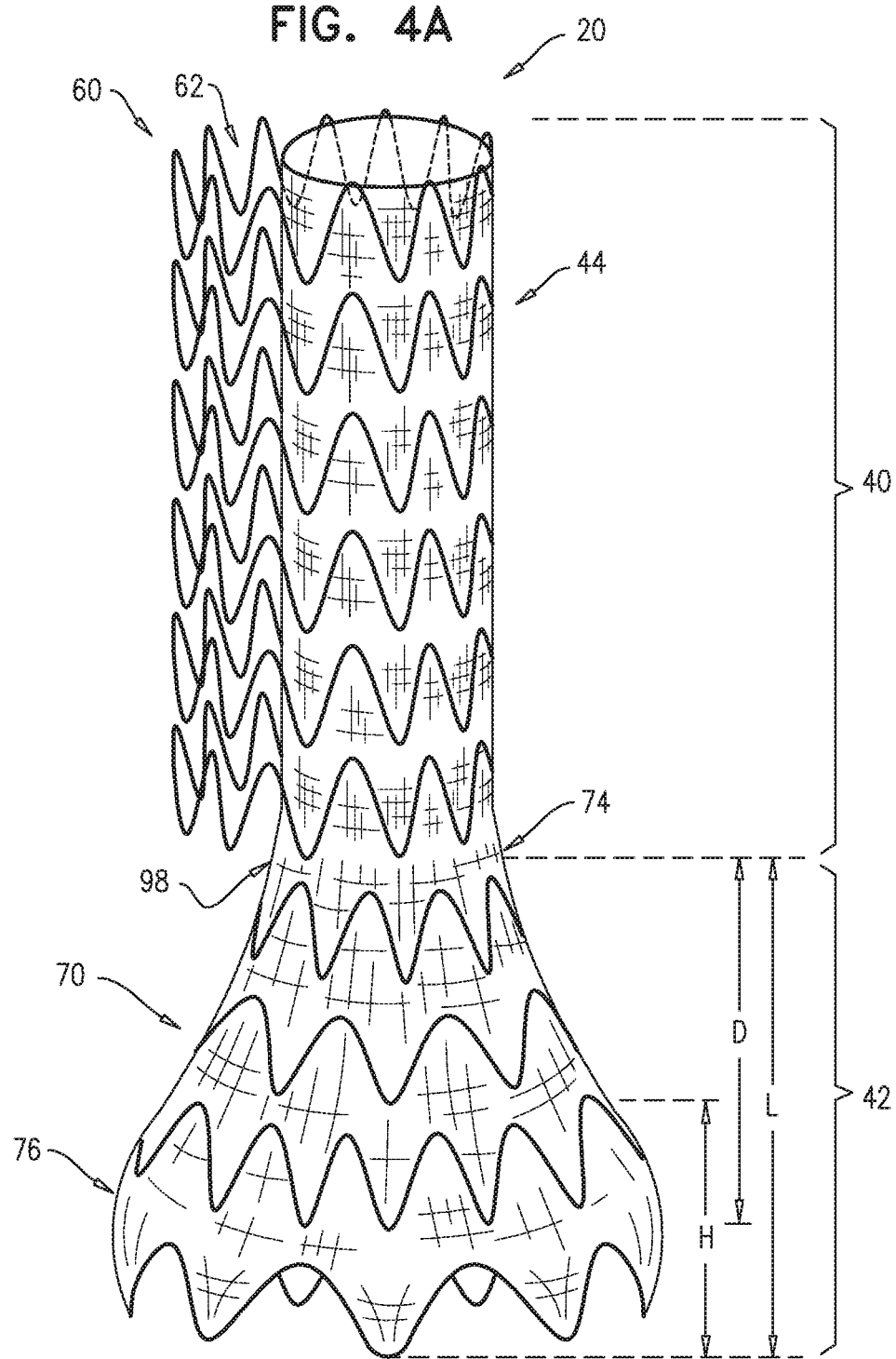

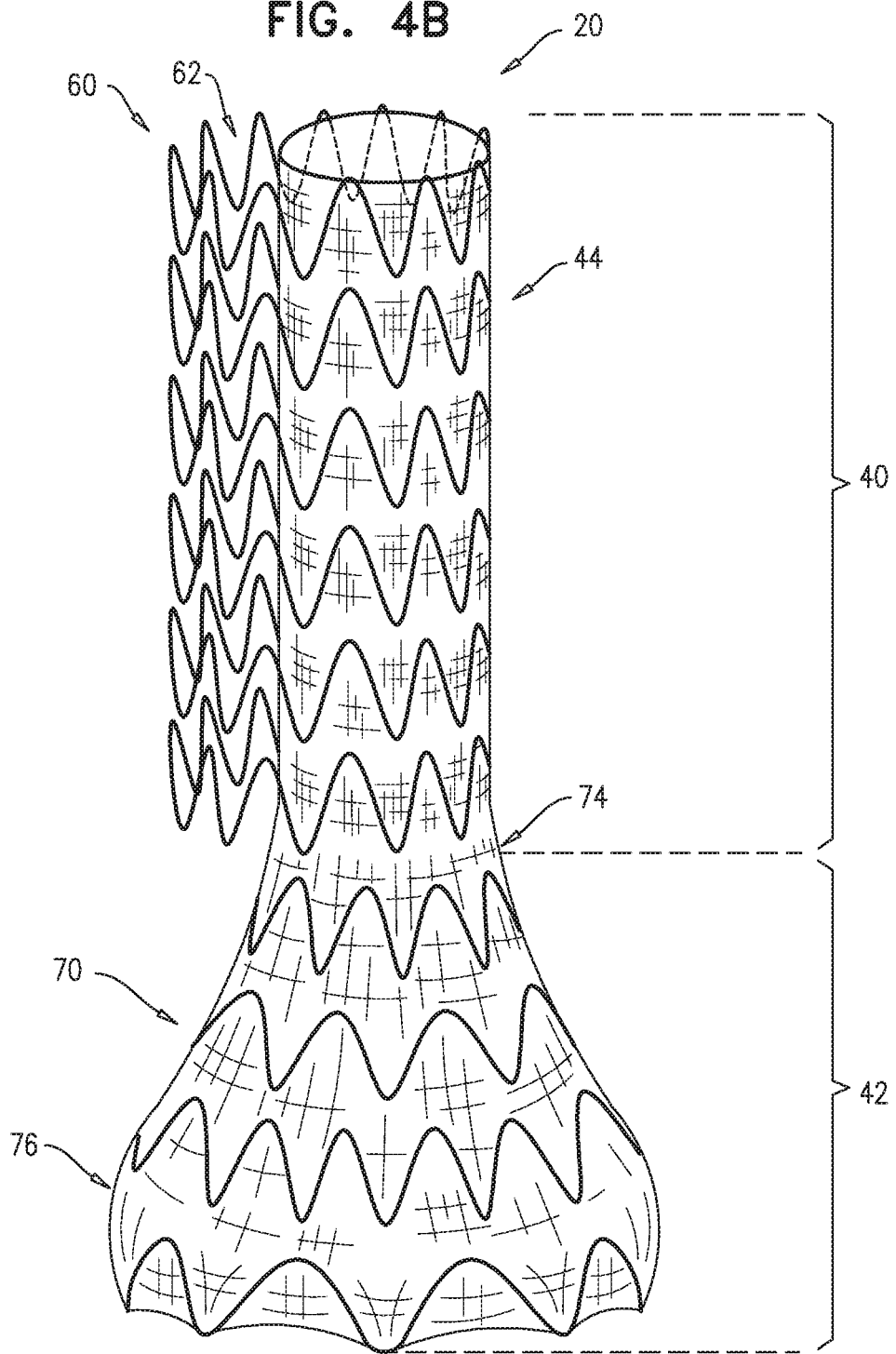

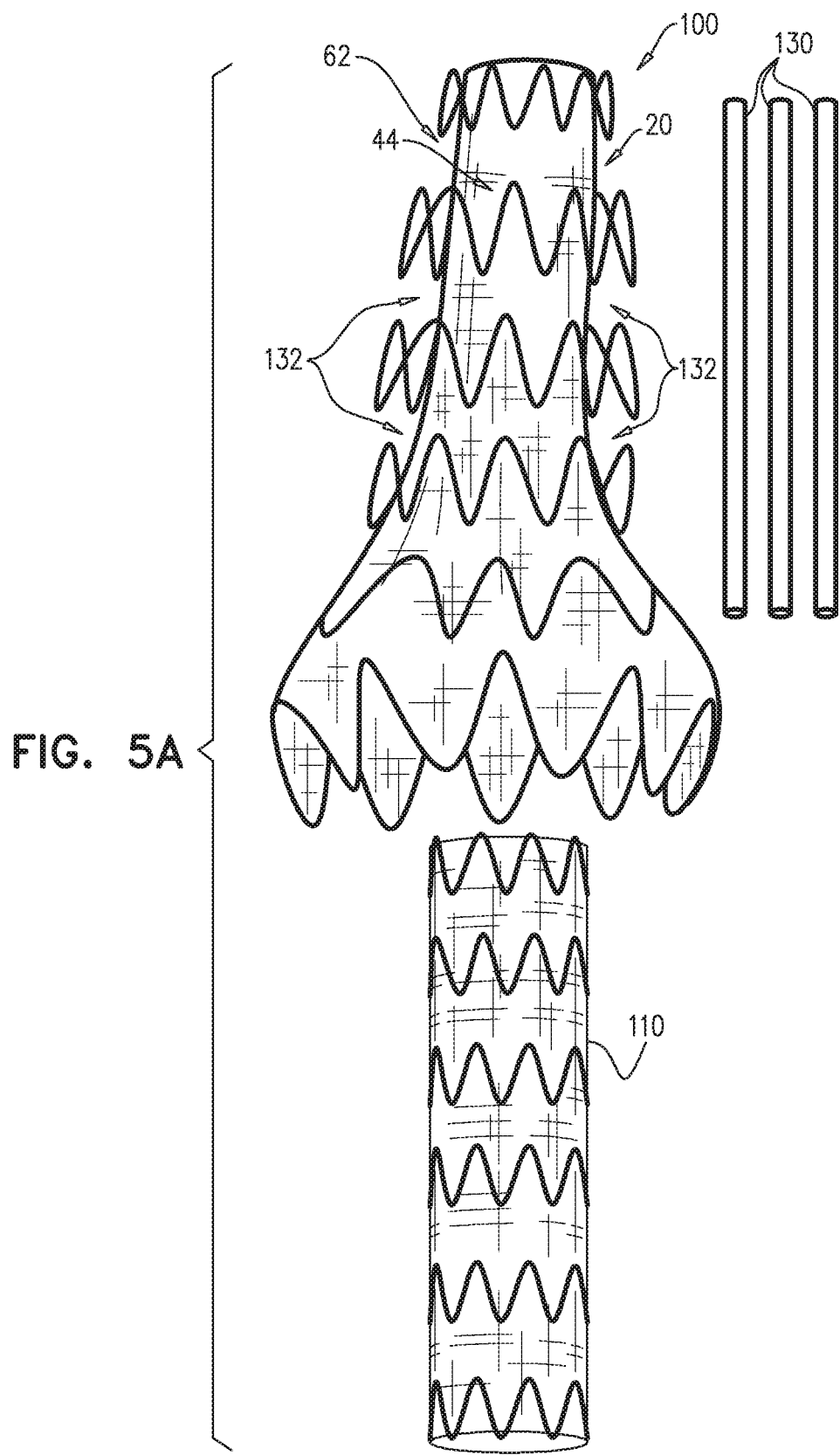

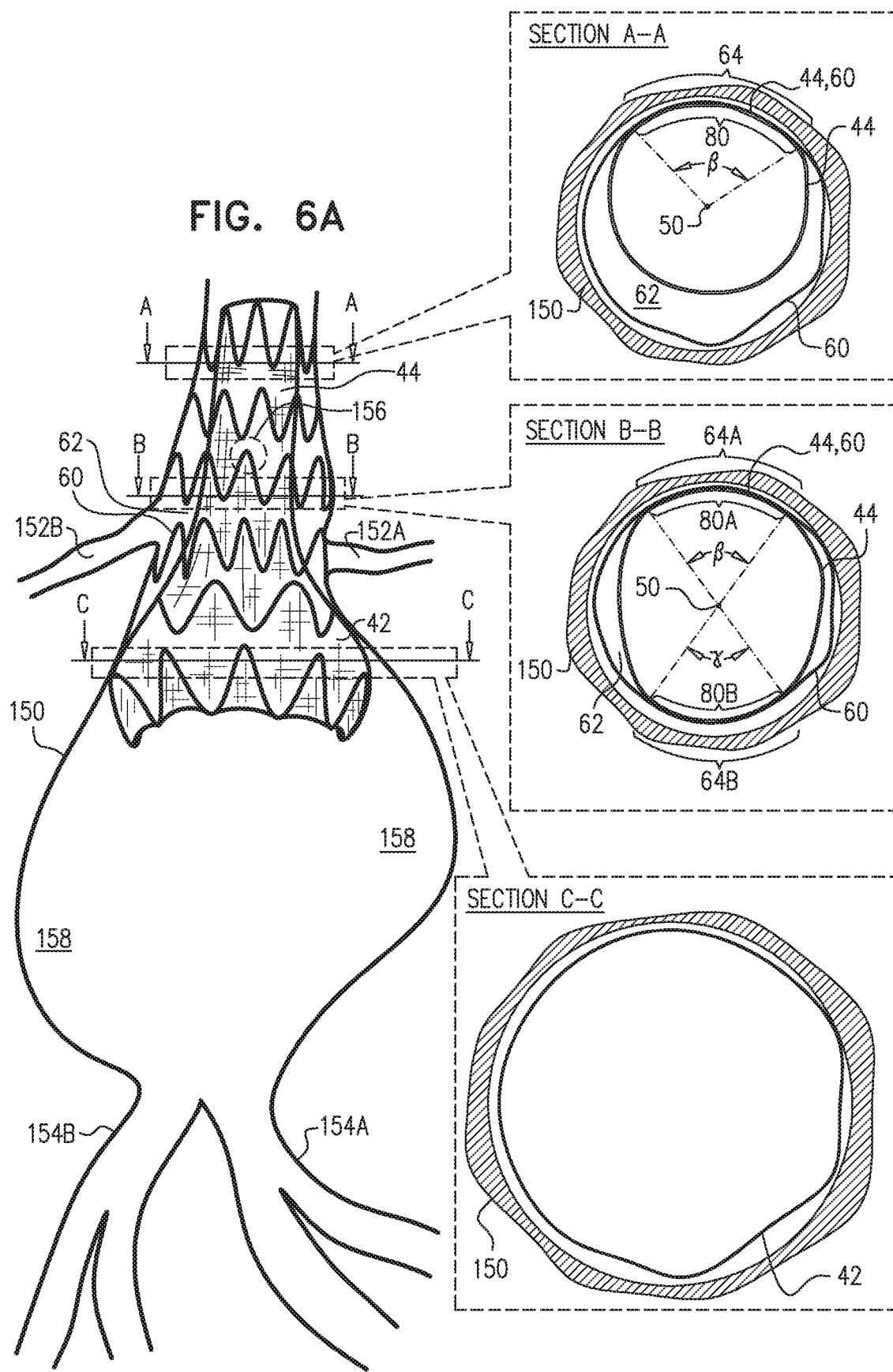

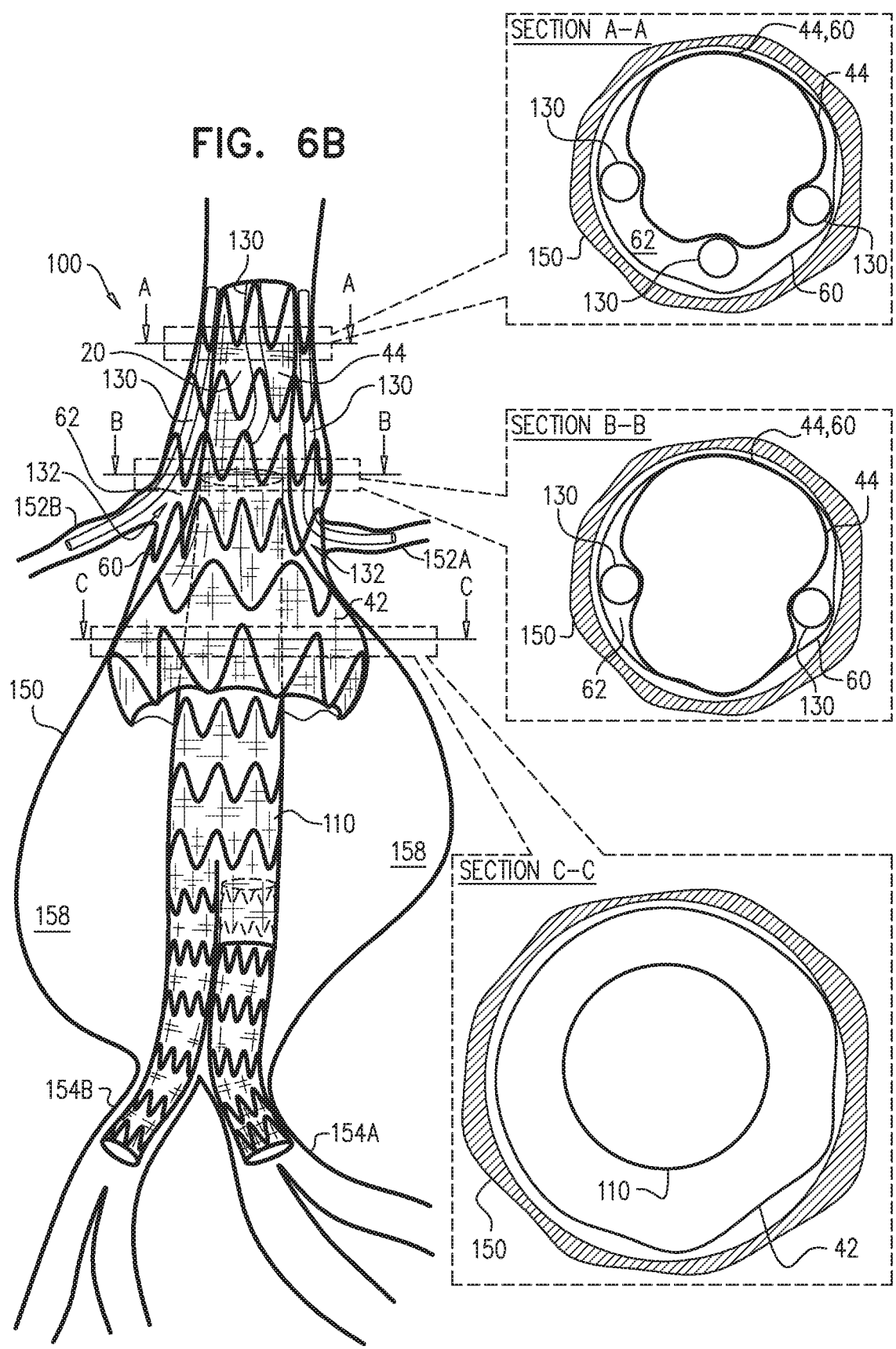

STENT-GRAFTS SYSTEMS WITH SKIRT

CROSS-REFERENCE TO RELATED APPLICATIONS

The present application claims priority from U.S. Provisional Application 62/254,432, filed Nov. 12, 2015, and U.S. Provisional Application 62/371,983, filed. Aug. 8, 2016, which are assigned to the assignee of the present application and are incorporated herein by reference.

FIELD OF THE APPLICATION

The present invention relates generally to implantable medical devices, and specifically to implantable stent-grafts.

BACKGROUND OF THE APPLICATION

Endovascular prostheses are sometimes used to treat aortic aneurysms. Such treatment includes implanting a stent or stent-graft within the diseased vessel to bypass the anomaly. An aneurysm is a sac formed by the dilation of the wall of the artery. Aneurysms may be congenital, but are usually caused by disease or, occasionally, by trauma. Aortic aneurysms which commonly form between the renal arteries and the iliac arteries are referred to as abdominal aortic aneurysms ("AAAs"). Other aneurysms occur in the aorta, such as thoracic aortic aneurysms ("TAAs") and aortic uni-iliac ("AUI") aneurysms. A TAA may occur downstream the aortic arch, i.e., in the descending aorta. Alternatively, a TAA may occur in the aortic arch itself, where the aorta branches to supply the brachiocephalic, left carotid and subclavian arteries, or may occur in the ascending aorta.

Endo-Vascular Aneurysm Repair (EVAR) has transformed the practice of treatment of aortic aneurysms from an open surgical approach to a much less invasive surgical approach. The first step of an endovascular intervention usually requires introducing a delivery system into the vasculature of a subject. If the crossing profile, i.e., the external diameter, of the delivery system is 24 Fr or lower (3 Fr=1 millimeter), a true percutaneous approach may be used, because vascular closure devices are available for proper closure of such puncture sites.

Blood vessels occasionally weaken or even rupture. For example, in the aortic artery, the vascular wall can weaken or tear, resulting in dangerous conditions such as aneurysm and dissection. Treatment of such conditions can be performed by implanting a prosthesis within the vascular system using minimally-invasive surgical procedures. An endoluminal prosthesis typically includes one or more stents affixed to graft material and is delivered to the treatment site by endovascular insertion. Once the endoluminal prosthesis is radially enlarged, it should remain in place indefinitely by self-attachment to the vessel wall, acting as a substitute vessel for the flow of blood or other fluids.

Aortic dissection is a tear or partial tear in the inner wall of the aorta, which causes blood to flow between the layers of the wall of the aorta, forcing the layers apart. Aortic dissections may be divided into two types in accordance with the Stanford classification. Type A dissections involve the ascending aorta and/or aortic arch, and possibly the descending aorta. Type B dissections involve the descending aorta or the arch (distal to right brachiocephalic artery origin), without involvement of the ascending aorta.

SUMMARY OF THE APPLICATION

Some embodiments of the present invention provide a multi-component endovascular system, which comprises a branch-enabling main endovascular prosthesis, and, typically, one or more branching endovascular prostheses. The branch-enabling main endovascular prosthesis is shaped so as to define a proximal branch-enabling longitudinal portion, and, typically, a distal skirt longitudinal portion. The proximal branch-enabling longitudinal portion comprises a proximal blood-carrying tubular structure and a blood-vessel-fixation structure. The blood-vessel-fixation structure comprises structural strut members, and, when the main endovascular prosthesis is unconstrained in a radially-expanded state, defines a structurally-supported space alongside and external to the proximal blood-carrying tubular structure, along the entire proximal branch-enabling longitudinal portion. The blood-vessel-fixation structure includes a non-contacting portion, which does not directly contact the proximal blood-carrying tubular structure, and which has an average graft surface area coverage of less than 20%.

The endovascular system may be used to treat a main artery, e.g., a descending aorta, suffering from an aneurysm, a dissection, or, more generally, a pathologically dilated main artery. Upon deployment of the branch-enabling main endovascular prosthesis, the blood-vessel-fixation structure creates the structurally-supported space alongside the proximal blood-carrying tubular structure, between the proximal blood-carrying tubular structure and a circumferential portion of a wall of the main artery, upstream of and alongside arteries that branch from the main artery. The branching endovascular prostheses are positioned extending along a portion of the branch-enabling main endovascular prosthesis and into respective branching arteries. The branching prostheses thus provide a blood-flow path from the main artery to the branching arteries. The structurally-supported space creates a non-compressible path for deployment of the branching endovascular prostheses around the proximal blood-carrying tubular structure. The low average graft surface area coverage of the non-contacting portion of the blood-vessel-fixation structure provides lateral openings through which the branching endovascular prostheses can be readily advanced for cannulation of the branching arteries. As a result, the endovascular system accommodates common anatomic variations in the axial and circumferential locations of the branching arteries, without the need to customize the main endovascular prosthesis for each patient.

The distal skirt longitudinal portion, if provided, presses against the arterial wall downstream of the branching arteries, thereby limiting blood flow into a sub-branching-arteries aneurysmal sac. The distal skirt longitudinal portion thus isolates the aneurysmal sac from the "gutter" created by the blood-vessel-fixation structure in the structurally-supported space.

For some applications, the endovascular system additionally comprises an extension endovascular prosthesis, which is sealingly coupled to the branch-enabling main endovascular prosthesis during the deployment procedure. Upon deployment of all of the endoluminal prostheses of the endovascular system, the endovascular system defines a blood-flow path from upstream of the branching arteries, to the branching arteries and downstream of the branching arteries.

The proximal blood-carrying tubular structure comprises a proximal portion of a graft member and structural strut members, which are fixed to the proximal portion of the graft member so as to provide a proximal blood-carrying lumen through the proximal blood-carrying tubular structure, when the main endovascular prosthesis is unconstrained in the radially-expanded state. The distal skirt longitudinal portion, if provided, comprises a distal skirt tubular structure, which comprises a distal portion of the graft member and structural strut members, which are fixed to the distal portion of the graft member.

Typically, a greatest distal-skirt outer cross-sectional area (A) equals at least 150% of a smallest distal-skirt outer cross-sectional area, and (B) equals at least 120% of an average proximal-blood-carrying inner cross-sectional area of the blood-carrying tubular structure, when the main endovascular prosthesis is unconstrained in the radially-expanded state. Typically, an average total proximal outer cross-sectional area of the proximal branch-enabling longitudinal portion, including the proximal blood-carrying tubular structure and the structurally-supported space, equals at least 120%, such as at least 140%, e.g., at least 170%, of the average proximal-blood-carrying inner cross-sectional area, when the main endovascular prosthesis is unconstrained in the radially-expanded state.

For some applications, the structural strut members comprise a plurality of proximal circumferential structural strut members, which, when the main endovascular prosthesis is unconstrained in the radially-expanded state (a) define blood-vessel-fixation structure, including the non-contacting portion and a contacting portion of the blood-vessel-fixation structure, and (h) are disposed entirely surrounding the proximal blood-carrying tubular structure, such that the contacting portion of the blood-vessel-fixation structure directly contacts a contact circumferential portion of the proximal blood-carrying tubular structure. Typically, the contact circumferential portion of the proximal blood-carrying tubular structure has an average arc angle of no more than 180 degrees, such as no more than 150 degrees, measured about a central longitudinal axis of the proximal blood-carrying tubular structure, when the main endovascular prosthesis is unconstrained in the radially-expanded state.

Some embodiments of the present invention provide an endovascular system, which comprises an endovascular prosthesis and one or more branching stent-grafts. The endovascular prosthesis comprises a stent-graft and an external coagulation inducer, which is fixed to an external surface of the stent-graft, and comprises a solid material. The external coagulation inducer is configured to impede blood flow external to the lumen of a blood-carrying tubular structure of the stent-graft of the endovascular prosthesis when a longitudinal portion of the endovascular prosthesis is placed side-by-side (i.e., in parallel with) with the one or more branching stent-grafts. The external coagulation inducer reduces the likelihood of long-term leakage (i.e., blood flow) through "gutters," which are the residual intravascular space disposed outside the lumens of the stent-graft and the branching stent-graft(s). As a result, the likelihood of type 1 endoleak is reduced.

For some applications, the external coagulation inducer comprises a plurality of non-contiguous external coagulation regions, which together define the external coagulation inducer. For example, the external coagulation regions may be disposed and configured to impede blood flow in respective chimneys of respective branching arteries.

For some applications, the material of the external coagulation inducer may be considered "fluffy," e.g., similar to steel wool. When the endovascular prosthesis is unconstrained in a radially-expanded state, (a) the external coagulation inducer is shaped so as to encompass at least a cube having an edge length of 3 mm and entirely filled with 216 sub-cubes, each of which has an edge length of 0.5 mm, and (b) at least 50% of the sub-cubes contain some of the solid material of the external coagulation inducer. Typically, at least 10% of the volume of the cube is void of solid matter. Alternatively or additionally, for some applications, at least 50% of the sub-cubes contain at least one external surface of the solid material of the external coagulation inducer, when the endovascular prosthesis is unconstrained in the radially-expanded state.

For some applications, the external coagulation inducer comprises a plurality of elongate coagulation members, each of which (a) is fixed, at at least one point along the elongate coagulation member, to the external surface of the stent-graft, and (b) has a length of between 1 and 15 cm when the endovascular prosthesis is unconstrained in the radially-expanded state. For some applications, each of the elongate coagulation members comprises one or more elongated members, which may, for example, have a diameter of between 0.1 and 0.5 mm. For some applications, each of the elongate members comprises a wire, i.e., a single extruded strand, or a fiber. For other applications, each of the elongate members comprises an, which comprises interlocked fibers.

For some applications, the external coagulation inducer comprises an extra-luminal skirt, which comprises a fiber mesh. Typically, at least 50% of an outer surface of the fiber mesh is not covered (either inside or outside) with graft material. The extra-luminal skirt is configured to assume (i) when the endovascular prosthesis is removably disposed in the delivery sheath, a radially-compressed delivery state, and (ii) when the endovascular prosthesis is unconstrained, a radially-expanded state, in which the extra-luminal skirt extends radially outward from the external surface of the stent-graft.

For some applications, the external coagulation inducer comprises one or more scales-segment members, each of which (a) comprises a plurality of scales, (b) is fixed, at at least one point along the scales-segment member, to the external surface of the stent-graft, and (c) extends around at least 20 mm of a circumference of the stent-graft.

For some applications, the external coagulation inducer comprises an extra-luminal skirt, which is configured to reduce the likelihood of long-term leakage through gutters, so as to reduce the likelihood of type 1 endoleak. In this configuration, the stent-graft comprises a first portion of structural strut members of the endovascular prosthesis and a first portion of a graft member of the endovascular prosthesis. The structural strut members of the first portion and the graft member of the first portion are attached to each other, and, when the endovascular prosthesis is unconstrained in the radially-expanded state, together are shaped so as to define a blood-carrying tubular structure defining a lumen. The extra-luminal skirt comprises a second portion of the structural strut members and a second portion of the graft member. The extra-luminal skirt is configured to assume (a) a radially-compressed delivery state when the endovascular prosthesis is removably disposed in the delivery sheath; in this state, the structural strut members of the first portion do not coincide with the structural strut members of second portion, and (b) a radially-expanded state when the endovascular prosthesis is unconstrained; in this state, the extra-luminal skirt extends radially outward from the external surface of the stent-graft.

For some applications, the external coagulation inducer surrounds an entire circumference of the stent-graft, when the endovascular prosthesis is unconstrained in the radially-expanded state. Typically, the external coagulation inducer extends along at least 50% of a total length of the stent-graft. In this configuration, the endovascular prosthesis may be deployed as a branching stent-graft. Typically, a substantial portion of the length of the endovascular prosthesis is disposed alongside a main stent-graft, and a portion of the endovascular prosthesis is disposed in a branching artery. The external coagulation inducer reduces the likelihood of long-term leakage outside the lumens of the endovascular prosthesis and the main stent-graft.

In some embodiments of the present invention, an endovascular system is provided that comprises a main steingraft, a branching stent-graft, and an anti-gutter linking endovascular prosthesis. The anti-gutter linking endovascular prosthesis comprises structural strut members, a graft member, and an internal coagulation inducer, which is attached to an internal surface of a lumen defined by the anti-gutter linking endovascular prosthesis. The internal coagulation inducer typically extends entirely around the circumference of the anti-gutter linking endovascular prosthesis. The main stent-graft, the branching stent-graft, the anti-gutter linking endovascular prosthesis, and the internal coagulation inducer are sized such that the main stent-graft and the branching stent-graft are disposable alongside each other passing through the internal coagulation inducer of the anti-gutter linking endovascular prosthesis, the main stent-graft, the branching stent-graft, and the anti-gutter linking endovascular prosthesis are in respective radially-expanded states. Upon deployment, the main stent-graft and the branching stent-graft run parallel to one another through the internal coagulation inducer of the anti-gutter linking endovascular prosthesis, with portions of the main stent-graft and the branching stent-graft touching the internal coagulation inducer, such that the internal coagulation inducer reduces the likelihood of long-term leakage (i.e., blood flow) through any gutters that might be created outside of the lumens of the main and branching stent-grafts.

There is therefore provided, in accordance with an inventive concept 1 of the present invention, an endovascular system including an endovascular prosthesis, which (1) is configured to transition from a radially-compressed delivery state to a radially-expanded state, (2) includes structural strut members and a graft member, and (3) is shaped so as to define:

(a) a proximal branch-enabling longitudinal portion, which includes:
  (i) a proximal blood-carrying tubular structure, which (A) includes a proximal portion of the graft member and some of the structural strut members, which are fixed to the proximal portion of the graft member so as to provide a proximal blood-carrying lumen through the proximal blood-carrying tubular structure, when the prosthesis is unconstrained in the radially-expanded state, and (B) has an average proximal-blood-carrying inner cross-sectional area, when the prosthesis is unconstrained in the radially-expanded state; and
  (ii) a blood-vessel-fixation structure, which includes some of the structural strut members, and which, when the prosthesis is unconstrained in the radially-expanded state:
    (A) defines a structurally-supported space alongside and external to the proximal blood-carrying tubular structure, along the entire proximal branch-enabling longitudinal portion,
    (B) includes a contacting portion, which directly contacts the proximal blood-carrying tubular structure, and which, at a plurality of locations of the contacting portion, is directly fixed to the proximal blood-carrying tubular structure, and
    (C) includes a non-contacting portion, which (1) does not directly contact the proximal blood-carrying tubular structure, and (2) has an average graft surface area coverage of less than 20%, and (b) a distal skirt longitudinal portion, which includes a distal skirt tubular structure, which (i) includes a distal portion of the graft member and some of the structural strut members, which are fixed to the distal portion of the graft member, and (ii) when the prosthesis is unconstrained in the radially-expanded state, has smallest and greatest distal-skirt outer cross-sectional areas at respective different longitudinal locations, wherein the greatest distal-skirt outer cross-sectional area (A) equals at least 150% of the smallest distal-skirt outer cross-sectional area, and (B) equals at least 120% of the average proximal-blood-carrying inner cross-sectional area, wherein an average total proximal outer cross-sectional area of the proximal branch-enabling longitudinal portion, including the proximal blood-carrying tubular structure and the structurally-supported space along the proximal branch-enabling longitudinal portion, equals at least 140% of the average proximal-blood-carrying inner cross-sectional area, when the prosthesis is unconstrained in the radially-expanded state.

Inventive concept 2. The endovascular system according to inventive concept 1, wherein the average total proximal outer cross-sectional area of the proximal branch-enabling longitudinal portion, including the proximal blood-carrying tubular structure and the structurally-supported space along the proximal branch-enabling longitudinal portion, equals at least 170% of the average proximal-blood-carrying inner cross-sectional area, when the prosthesis is unconstrained in the radially-expanded state.

Inventive concept 3. The endovascular system according to inventive concept 1, wherein a volume of the structurally-supported space along the distal skirt longitudinal portion equals less than 10% of a volume of the distal skirt tubular structure, when the prosthesis is unconstrained in the radially-expanded state.

Inventive concept 4. The endovascular system according to inventive concept 3, wherein the structurally-supported space is disposed entirely along the proximal branch-enabling longitudinal portion, such that none of the structurally-supported space is disposed along the distal skirt longitudinal portion, when the prosthesis is unconstrained in the radially-expanded state.

Inventive concept 5. The endovascular system according to inventive concept 1, wherein the average graft surface area coverage is less than 10%.

Inventive concept 6. The endovascular system according to inventive concept 5, wherein the average graft surface area coverage is less than 5%.

Inventive concept 7. The endovascular system according to inventive concept 6, wherein the average graft surface area coverage is 0%.

Inventive concept 8. The endovascular system according to inventive concept 1, wherein the proximal blood-carrying tubular structure is generally cylindrical, when the prosthesis is unconstrained in the radially-expanded state.

Inventive concept 9. The endovascular system according to inventive concept 1, wherein the blood-vessel-fixation structure is generally cylindrical, when the prosthesis is unconstrained in the radially-expanded state.

Inventive concept 10. The endovascular system according to inventive concept 1, wherein, when the prosthesis is unconstrained in the radially-expanded state, the proximal blood-carrying tubular structure is generally cylindrical, and the blood-vessel-fixation structure is generally cylindrical.

Inventive concept 11. The endovascular system according to inventive concept 1, wherein the structural strut members of the blood-vessel-fixation structure are circumferential and are disposed at respective longitudinal positions along the blood-vessel-fixation structure, when the prosthesis is unconstrained in the radially-expanded state.

Inventive concept 12. The endovascular system according to inventive concept 1, wherein the contacting portion of the blood-vessel-fixation structure directly contacts an external surface of the proximal blood-carrying tubular structure, when the prosthesis is unconstrained in the radially-expanded state.

Inventive concept 13. The endovascular system according to inventive concept 1, wherein the distal skirt longitudinal portion monotonically widens in a proximal-to-distal direction along an entire length of the distal skirt longitudinal portion, when the prosthesis is unconstrained in the radially-expanded state.

Inventive concept 14. The endovascular system according to inventive concept 1, wherein the distal skirt longitudinal portion (a) monotonically widens in a proximal-to-distal direction to the longitudinal location having the greatest distal-skirt outer cross-sectional area, and (b) narrows in a proximal-to-distal direction from the longitudinal location having the greatest distal-skirt outer cross-sectional area, when the prosthesis is unconstrained in the radially-expanded state.

Inventive concept 15. The endovascular system according to inventive concept 14, wherein the longitudinal location having the greatest distal-skirt outer cross-sectional area is longitudinally located on a distal half of the distal skirt longitudinal portion, when the prosthesis is unconstrained in the radially-expanded state.

Inventive concept 16. The endovascular system according to inventive concept 15, wherein die longitudinal location having the greatest distal-skirt outer cross-sectional area is longitudinally located a distance from a proximal end of the distal skirt longitudinal portion, which distance equals between 50% and 85% of a length of the distal skirt longitudinal portion, when the prosthesis is unconstrained in the radially-expanded state.

Inventive concept 17. The endovascular system according to inventive concept 1, wherein an average spring constant of the structural strut members of the proximal blood-carrying tubular structure is no more than 85% of an average spring constant of the structural strut members of the blood-vessel-fixation structure.

Inventive concept 18. The endovascular system according to inventive concept 1, wherein an average unconstrained perimeter of the proximal blood-carrying tubular structure is 40 to 90 mm, when the prosthesis is unconstrained in the radially-expanded state.

Inventive concept 19. The endovascular system according to inventive concept 1, wherein, when the prosthesis is unconstrained in the radially-expanded state:
the proximal branch-enabling longitudinal portion defines, at a plurality of longitudinal locations, a plurality of respective different ratios of (a) a total proximal outer cross-sectional area of the proximal branch-enabling longitudinal portion, including the proximal blood-carrying tubular structure and the structurally-supported space along the proximal branch-enabling longitudinal portion, to (b) a proximal-blood-carrying inner cross-sectional area of the proximal blood-carrying tubular structure, and
a greatest one of the ratios is at least 2.5.

Inventive concept 20. The endovascular system according to inventive concept 1, wherein the proximal blood-carrying tubular structure is self-expanding.

Inventive concept 21. The endovascular system according to inventive concept 1, wherein the distal skirt longitudinal portion is self-expanding.

Inventive concept 22. The endovascular system according to inventive concept 1, wherein the structural strut members include a superelastic alloy.

Inventive concept 23. The endovascular system according to inventive concept 22, wherein the superelastic alloy includes Nitinol.

Inventive concept 24. The endovascular system according to inventive concept 1, wherein the structural strut members include elastic stainless steel.

Inventive concept 25. The endovascular system according to any one of inventive concepts 1-24, wherein the structural strut members include a plurality of proximal circumferential structural strut members, which, when the prosthesis is unconstrained in the radially-expanded state:
define the blood-vessel-fixation structure, including the contacting and non-contacting portions thereof, and
are disposed entirely surrounding the proximal blood-carrying tubular structure, such that the contacting portion of the blood-vessel-fixation structure directly contacts a contact circumferential portion of the proximal blood-carrying tubular structure.

Inventive concept 26. The endovascular system according to inventive concept 25, wherein the contact circumferential portion of the proximal blood-carrying tubular structure has an average arc angle, measured about a central longitudinal axis of proximal blood-carrying tubular structure, of no more than 180 degrees, when the prosthesis is unconstrained in the radially-expanded state.

Inventive concept 27. The endovascular system according to inventive concept 26, wherein the average arc angle is no more than 150 degrees.

Inventive concept 28. The endovascular system according to inventive concept 25, wherein the contact circumferential portion of the proximal blood-carrying tubular structure has an average arc angle, measured about a central longitudinal axis of proximal blood-carrying tubular structure, of at least 140 degrees, when the prosthesis is unconstrained in the radially-expanded state.

Inventive concept 29. The endovascular system according to inventive concept 28, wherein the average arc angle is at least 210 degrees.

Inventive concept 30. The endovascular system according to inventive concept 25, wherein the proximal circumferential structural strut members at least partially define the proximal blood-carrying tubular structure, when the prosthesis is unconstrained in the radially-expanded state.

Inventive concept 31. The endovascular system according to inventive concept 30, wherein, in addition to the proximal circumferential structural strut members, one or more others of the structural strut members are securely directly attached to the graft member and at least partially define the proximal blood-carrying tubular structure, when the prosthesis is unconstrained in the radially-expanded state.

Inventive concept 32. The endovascular system according to inventive concept 31, wherein the one or more other structural strut members include one or more circumferential structural strut members, which are disposed at respective longitudinal positions along the proximal blood-carrying tubular structure.

Inventive concept 33. The endovascular system according to inventive concept 25, wherein the contact circumferential portion of the proximal blood-carrying tubular structure is entirely circumferentially contiguous along at least a longitudinal portion of the proximal blood-carrying tubular structure, when the prosthesis is unconstrained in the radially-expanded state.

Inventive concept 34. The endovascular system according to inventive concept 25, wherein the contact circumferential portion of the proximal blood-carrying tubular structure is circumferentially non-contiguous along at least a longitudinal portion of the proximal blood-carrying tubular structure, when the prosthesis is unconstrained in the radially-expanded state.

Inventive concept 35. The endovascular system according to inventive concept 25, wherein an arc angle of the contact circumferential portion of the proximal blood-carrying tubular structure, measured about a central longitudinal axis of proximal blood-carrying tubular structure, is greater at a distal end of the proximal blood-carrying tubular structure than at a proximal end of the proximal blood-carrying tubular structure, when the prosthesis is unconstrained in the radially-expanded state.

Inventive concept 36. The endovascular system according to inventive concept 35, wherein the contact circumferential portion of the proximal blood-carrying tubular structure is circumferentially non-contiguous at at least the distal end of the proximal blood-carrying tubular structure, when the prosthesis is unconstrained in the radially-expanded state.

Inventive concept 37. The endovascular system according to inventive concept 36, wherein the contact circumferential portion of the proximal blood-carrying tubular structure is entirely circumferentially contiguous at at least the proximal end of the proximal blood-carrying tubular structure, when the prosthesis is unconstrained in the radially-expanded state.

Inventive concept 38. The endovascular system according to inventive concept 35, wherein the arc angle monotonically non-decreases from the proximal end to the distal end of the proximal blood-carrying tubular structure, when the prosthesis is unconstrained in the radially-expanded state.

Inventive concept 39. The endovascular system according to inventive concept 25,
wherein the blood-vessel-fixation structure has an average unconstrained perimeter when the prosthesis is unconstrained in the radially-expanded state,
wherein the proximal blood-carrying tubular structure includes a non-contact circumferential portion, which includes the entire proximal blood-carrying tubular structure circumference other than the contact circumferential portion of the proximal blood-carrying tubular structure, when the prosthesis is unconstrained in the radially-expanded state, and
wherein an average spring constant of the structural strut members of the non-contact circumferential portion of the proximal blood-carrying tubular structure is no more than 90% of an average spring constant of the structural strut members of the contacting portion of the blood-vessel-fixation structure.

Inventive concept 40. The endovascular system according to inventive concept 25, wherein an average unconstrained perimeter of the blood-vessel-fixation structure is 70 to 130 mm, when the prosthesis is unconstrained in the radially-expanded state.

Inventive concept 41. The endovascular system according to inventive concept 25, wherein, when the prosthesis is unconstrained in the radially-expanded state:
the proximal blood-carrying tubular structure includes a non-contact circumferential portion, which includes the entire proximal blood-carrying tubular structure circumference other than the contact circumferential portion of the proximal blood-carrying tubular structure, and
an average graft surface area coverage of the non-contact circumferential portion of the proximal blood-carrying tubular structure is at least 90%.

Inventive concept 42. The endovascular system according to inventive concept 41, wherein the average graft surface area coverage of the non-contact circumferential portion of the proximal blood-carrying tubular structure is at least 95%, when the prosthesis is unconstrained in the radially-expanded state.

Inventive concept 43. The endovascular system according to any one of inventive concepts 1-24, wherein the proximal blood-carrying tubular structure and the blood-vessel-fixation structure include some of the same structural strut members, when the prosthesis is unconstrained in the radially-expanded state.

Inventive concept 44. The endovascular system according to inventive concept 43, wherein the proximal blood-carrying tubular structure includes, in addition to the some of the same structural strut members, others of the structural strut members, which are securely directly attached to the graft member and at least partially define the proximal blood-carrying tubular structure, when the prosthesis is unconstrained in the radially-expanded state.

Inventive concept 45. The endovascular system according to any one of inventive concepts 1-24,
wherein the endovascular prosthesis is a main endovascular prosthesis,
wherein the endovascular system further includes an extension endovascular prosthesis, which is configured to transition from a radially-compressed delivery state to a radially-expanded state, and
wherein the main and the extension endovascular prostheses are configured to be sealingly couplable together so as to together define a blood-flow path from the proximal blood-carrying tubular structure to the extension endovascular prosthesis, when the main and the extension endovascular prostheses are in their respective radially-expanded states.

Inventive concept 46. The endovascular system according to inventive concept 45,
wherein the main endovascular prosthesis further includes a prosthesis-engagement member, and
wherein, when the main and the extension endovascular prostheses are in their respective radially-expanded states:
the prosthesis-engagement member (a) is tubular, and (b) is disposed at least partially within the main endovascular prosthesis, and
the prosthesis-engagement member and the extension endovascular prosthesis are configured to be sealingly couplable together such that the main and the extension endovascular prostheses together define the blood-flow path from the proximal blood-carrying tubular structure to the extension endovascular prosthesis.

Inventive concept 47. The endovascular system according to any one of inventive concepts 1-24,
wherein the endovascular prosthesis is a main endovascular prosthesis, and
wherein the endovascular system further includes at least one branching endovascular prosthesis, which is configured to transition from a radially-compressed delivery state to a radially-expanded state, and which has an average inner cross-sectional area that equals between 15% and 50% of the average proximal-blood-carrying inner cross-sectional area of the proximal blood-carrying tubular structure, when the main and the branching endovascular prostheses are in their respective radially-expanded states.

Inventive concept 48. The endovascular system according to any one of inventive concepts 1-24, wherein the endovascular system does not include any branching endovascular prostheses.

Inventive concept 49. The endovascular system according to inventive concept 48,
wherein the endovascular prosthesis is a main endovascular prosthesis,
wherein the endovascular system further includes an extension endovascular prosthesis, which is configured to transition from a radially-compressed delivery state to a radially-expanded state, and
wherein the main and the extension endovascular prostheses are configured to be sealingly coupleable together so as to together define a blood-flow path from the proximal blood-carrying tubular structure to the extension endovascular prosthesis, when the main and the extension endovascular prostheses are in their respective radially-expanded states.

There is further provided, in accordance with an inventive concept 1 inventive concept 50 of the present invention, a method including:
providing an endovascular prosthesis, which (1) is configured to transition from a radially-compressed delivery state to a radially-expanded state, (2) includes structural strut members and a graft member, and (3) is shaped so as to define a proximal branch-enabling longitudinal portion, which includes (i) a proximal blood-carrying tubular structure, which includes a proximal portion of the graft member and some of the structural strut members, which are fixed to the proximal portion of the graft member so as to provide a proximal blood-carrying lumen through the proximal blood-carrying tubular structure, when the prosthesis is unconstrained in the radially-expanded state; and (ii) a blood-vessel-fixation structure, which includes some of the structural strut members, and which, when the prosthesis is unconstrained in the radially-expanded state, (A) defines a structurally-supported space alongside and external to the proximal blood-carrying tubular structure, along the entire proximal branch-enabling longitudinal portion, (B) includes a contacting portion, which directly contacts the proximal blood-carrying tubular structure, and which, at a plurality of locations of the contacting portion, is directly fixed to the proximal blood-carrying tubular structure, and (C) includes a non-contacting portion, which (1) does not directly contact the proximal blood-carrying tubular structure, and (2) has an average graft surface area coverage of less than 20%;
while the endovascular prosthesis is removably constrained in the radially-compressed delivery state, transvascularly introducing the endovascular prosthesis into a main artery of a subject and positioning the endovascular prosthesis such that the proximal blood-vessel-fixation structure is upstream of and alongside one or more branching arteries that branch from the main artery, and the proximal blood-carrying tubular structure is entirely within the main artery; and
releasing the endovascular prosthesis from the radially-compressed delivery state such that blood-vessel-fixation structure creates the structurally-supported space between the blood-carrying tubular structure and a circumferential portion of a wall of the main artery.

Inventive concept 51. The method according to inventive concept 50, wherein positioning the endovascular prosthesis includes positioning the endovascular prosthesis such that the proximal blood-vessel-fixation structure is upstream of, alongside, and downstream of the one or more branching arteries, such that the blood-vessel-fixation structure longitudinally spans the one or more branching arteries.

Inventive concept 52. The method according to inventive concept 50, wherein providing the endovascular prosthesis includes providing the endovascular prosthesis in which, when the prosthesis is unconstrained in the radially-expanded state, an average total proximal outer cross-sectional area of the proximal branch-enabling longitudinal portion, including the proximal blood-carrying tubular structure and the structurally-supported space along the proximal branch-enabling longitudinal portion, equals at least 140% of an average proximal-blood-carrying inner cross-sectional area of the proximal blood-carrying tubular structure.

Inventive concept 53. The method according to inventive concept 52, wherein providing the endovascular prosthesis includes providing the endovascular prosthesis in which, when the prosthesis is unconstrained in the radially-expanded state, the average total proximal outer cross-sectional area of the proximal branch-enabling longitudinal portion, including the proximal blood-carrying tubular structure and the structurally-supported space along the proximal branch-enabling longitudinal portion, equals at least 170% of the average proximal-blood-carrying inner cross-sectional area.

Inventive concept 54. The method according to inventive concept 50,
wherein providing the endovascular prosthesis includes providing the endovascular prosthesis shaped so as to further define a distal skirt longitudinal portion, which includes a distal skirt tubular structure, which (i) includes a distal portion of the graft member and some of the structural strut members, which are fixed to the distal portion of the graft member, and (ii) when the prosthesis is unconstrained in the radially-expanded state, has smallest and greatest distal-skirt outer cross-sectional areas at respective different longitudinal locations, wherein the greatest distal-skirt outer cross-sectional area (A) equals at least 150% of the smallest distal-skirt outer cross-sectional area, and (B) equals at least 120% of an average proximal-blood-carrying inner cross-sectional area of the proximal blood-carrying tubular structure, and
wherein releasing the endovascular prosthesis includes releasing the endovascular prosthesis such that the distal skirt longitudinal portion presses against the wall of the main artery downstream of the one or more branching arteries.

Inventive concept 55. The method according to inventive concept 54, wherein providing the endovascular prosthesis includes providing the endovascular prosthesis in which a volume of the structurally-supported space along the distal skirt longitudinal portion equals less than 10% of a volume of the distal skirt tubular structure, when the prosthesis is unconstrained in the radially-expanded state.

Inventive concept 56. The method according to inventive concept 55, wherein providing the endovascular prosthesis includes providing the endovascular prosthesis in which the structurally-supported space is disposed entirely along the proximal branch-enabling longitudinal portion, such that none of the structurally-supported space is disposed along the distal skirt longitudinal portion, when the prosthesis is unconstrained in the radially-expanded state.

Inventive concept 57. The method according to inventive concept 54, wherein providing the endovascular prosthesis includes providing the endovascular prosthesis in which the distal skirt longitudinal portion monotonically widens in a proximal-to-distal direction along an entire length of the distal skirt longitudinal portion, when the prosthesis is unconstrained in the radially-expanded state.

Inventive concept 58. The method according to inventive concept 54, wherein providing the endovascular prosthesis includes providing the endovascular prosthesis in which the distal skirt longitudinal portion (a) monotonically widens in a proximal-to-distal direction to the longitudinal location having the greatest distal-skirt outer cross-sectional area, and (b) narrows in a proximal-to-distal direction from the longitudinal location having the greatest distal-skirt outer cross-sectional area, when the prosthesis is unconstrained in the radially-expanded state.

Inventive concept 59. The method according to inventive concept 58, wherein providing the endovascular prosthesis includes providing the endovascular prosthesis in which the longitudinal location having the greatest distal-skirt outer cross-sectional area is longitudinally located on a distal half of the distal skirt longitudinal portion, when the prosthesis is unconstrained in the radially-expanded state.

Inventive concept 60. The method according to inventive concept 59, wherein providing the endovascular prosthesis includes providing the endovascular prosthesis in which the longitudinal location having the greatest distal-skirt outer cross-sectional area is longitudinally located a distance from a proximal end of the distal skirt longitudinal portion, which distance equals between 50% and 85% of a length of the distal skirt longitudinal portion, when the prosthesis is unconstrained in the radially-expanded state.

Inventive concept 61. The method according to inventive concept 54, wherein providing the endovascular prosthesis includes providing the endovascular prosthesis in which the distal skirt longitudinal portion is self-expanding.

Inventive concept 62. The method according to inventive concept 50, wherein the endovascular prosthesis is a main endovascular prosthesis, and wherein the method further includes:
providing an extension endovascular prosthesis, which is configured to transition from a radially-compressed delivery state to a radially-expanded state;
while the extension endovascular prosthesis is removably constrained in its radially-compressed delivery state, transvascularly introducing the extension endovascular prosthesis into the main artery; and
releasing the extension endovascular prosthesis from its radially-compressed delivery state so as to sealingly coupling the main and the extension endovascular prostheses together, such that the main and the extension endovascular prostheses together define a blood-flow path from the proximal blood-carrying tubular structure to the extension endovascular prosthesis.

Inventive concept 63. The method according to inventive concept 62,
wherein providing the main endovascular prosthesis includes providing the main endovascular prosthesis in which the main endovascular prosthesis further includes a prosthesis-engagement member, which (a) is tubular, and (b) is disposed at least partially within the main endovascular prosthesis, when the main and the extension endovascular prostheses are in their respective radially-expanded states, and
wherein sealingly coupling the main and the extension endovascular prostheses together includes sealingly coupling the prosthesis-engagement member and the extension endovascular prosthesis together, such that the main and the extension endovascular prostheses together define the blood-flow path from the proximal blood-carrying tubular structure to the extension endovascular prosthesis.

Inventive concept 64. The method according to inventive concept 50, wherein the endovascular prosthesis is a main endovascular prosthesis, and wherein the method further includes:
providing at least one branching endovascular prosthesis, which is configured to transition from a radially-compressed delivery state to a radially-expanded state, and which has an average inner cross-sectional area that equals between 15% and 50% of the average proximal-blood-carrying inner cross-sectional area of the proximal blood-carrying tubular structure, when the main and the branching endovascular prostheses are in their respective radially-expanded states;
while the branching endovascular prosthesis is removably constrained in its radially-compressed delivery state, (a) transvascularly introducing the branching endovascular prosthesis into the main artery, and (b) advancing the branching endovascular prosthesis through a portion of the structurally-supported space and into one of the branching arteries; and
releasing the branching endovascular prosthesis from its radially-compressed delivery state so as to provide a blood-flow path from the main artery to the branching artery.

Inventive concept 65. The method according to inventive concept 64,
wherein providing the branching endovascular prosthesis includes providing the branching endovascular prosthesis in which the blood-vessel-fixation structure is shaped so as to define a plurality of lateral openings when the branching endovascular prosthesis is in its radially-expanded state, and
wherein advancing the branching endovascular prosthesis through the portion of the structurally-supported space and into one of the branching arteries includes passing the branching endovascular prosthesis through one of the lateral openings.

Inventive concept 66. The method according to inventive concept 50, wherein the method does not include deploying any branching endovascular prostheses through a portion of the structurally-supported space.

Inventive concept 67. The method according to inventive concept 50, wherein a smallest one of the one or more branching arteries has a proximal diameter that is no more than 30% of a diameter of the main artery at a branching location.

Inventive concept 68. The method according to inventive concept 67, wherein the proximal diameter is no more than 20% of the diameter of the main artery at the branching location.

Inventive concept 69. The method according to inventive concept 50, wherein providing the endovascular prosthesis includes providing the endovascular prosthesis in which the average graft surface area coverage is less than 10%.

Inventive concept 70. The method according to inventive concept 69, wherein providing the endovascular prosthesis includes providing the endovascular prosthesis in which the average graft surface area coverage is less than 5%.

Inventive concept 71. The method according to inventive concept 70, wherein providing the endovascular prosthesis includes providing the endovascular prosthesis in which the average graft surface area coverage is 0%.

Inventive concept 72. The method according to inventive concept 50, wherein providing the endovascular prosthesis includes providing the endovascular prosthesis in which the proximal blood-carrying tubular structure is generally cylindrical, when the prosthesis is unconstrained in the radially-expanded state.

Inventive concept 73. The method according to inventive concept 50, wherein providing the endovascular prosthesis includes providing the endovascular prosthesis in which the blood-vessel-fixation structure is generally cylindrical, when the prosthesis is unconstrained in the radially-expanded state.

Inventive concept 74. The method according to inventive concept 50, wherein providing the endovascular prosthesis includes providing the endovascular prosthesis in which, when the prosthesis is unconstrained in the radially-expanded state, the proximal blood-carrying tubular structure is generally cylindrical, and the blood-vessel-fixation structure is generally cylindrical.

Inventive concept 75. The method according to inventive concept 50, wherein providing the endovascular prosthesis includes providing the endovascular prosthesis in which the structural strut members of the blood-vessel-fixation structure are circumferential and are disposed at respective longitudinal positions along the blood-vessel-fixation structure, when the prosthesis is unconstrained in the radially-expanded state.

Inventive concept 76. The method according to inventive concept 50, wherein providing the endovascular prosthesis includes providing the endovascular prosthesis in which the contacting portion of the blood-vessel-fixation structure directly contacts an external surface of the proximal blood-carrying tubular structure, when the prosthesis is unconstrained in the radially-expanded state.

Inventive concept 77. The method according to inventive concept 50, wherein providing the endovascular prosthesis includes providing the endovascular prosthesis in which an average spring constant of the structural strut members of the proximal blood-carrying tubular structure is no more than 85% of an average spring constant of the structural strut members of the blood-vessel-fixation structure.

Inventive concept 78. The method according to inventive concept 50, wherein providing the endovascular prosthesis includes providing the endovascular prosthesis in which an average unconstrained perimeter of the proximal blood-carrying tubular structure is 40 to 90 mm, when the prosthesis is unconstrained in the radially-expanded state.

Inventive concept 79. The method according to inventive concept 50, wherein providing the endovascular prosthesis includes providing the endovascular prosthesis in which, when the prosthesis is unconstrained in the radially-expanded state:

the proximal branch-enabling longitudinal portion defines, at a plurality of longitudinal locations, a plurality of respective different ratios of (a) a total proximal outer cross-sectional area of the proximal branch-enabling longitudinal portion, including the proximal blood-carrying tubular structure and the structurally-supported space along the proximal branch-enabling longitudinal portion, to (b) a proximal-blood-carrying inner cross-sectional area of the proximal blood-carrying tubular structure, and a greatest one of the ratios is at least 2.5.

Inventive concept 80. The method according to inventive concept 50, wherein providing the endovascular prosthesis includes providing the endovascular prosthesis in which the proximal blood-carrying tubular structure is self-expanding.

Inventive concept 81. The method according to inventive concept 50, wherein providing the endovascular prosthesis includes providing the endovascular prosthesis in which the structural strut members include a superelastic alloy.

Inventive concept 82. The method according to inventive concept 81, wherein providing the endovascular prosthesis includes providing the endovascular prosthesis in which the superelastic alloy includes Nitinol.

Inventive concept 83. The method according to inventive concept 50, wherein providing the endovascular prosthesis includes providing the endovascular prosthesis in which the structural strut members include elastic stainless steel.

Inventive concept 84. The method according to inventive concept 50, wherein providing the endovascular prosthesis includes providing the endovascular prosthesis in which the structural strut members include a plurality of proximal circumferential structural strut members, which, when the prosthesis is unconstrained in the radially-expanded state:

define the blood-vessel-fixation structure, including the contacting and non-contacting portions thereof, and are disposed entirely surrounding the proximal blood-carrying tubular structure, such that the contacting portion of the blood-vessel-fixation structure directly contacts a contact circumferential portion of the proximal blood-carrying tubular structure.

Inventive concept 85. The method according to inventive concept 84, wherein providing the endovascular prosthesis includes providing the endovascular prosthesis in which the contact circumferential portion of the proximal blood-carrying tubular structure has an average arc angle, measured about a central longitudinal axis of proximal blood-carrying tubular structure, of no more than 180 degrees, when the prosthesis is unconstrained in the radially-expanded state.

Inventive concept 86. The method according to inventive concept 85, wherein providing the endovascular prosthesis includes providing the endovascular prosthesis in which the average arc angle is no more than 150 degrees.

Inventive concept 87. The method according to inventive concept 84, wherein providing the endovascular prosthesis includes providing the endovascular prosthesis in which the contact circumferential portion of the proximal blood-carrying tubular structure has an average arc angle of at least 140 degrees, measured about a central longitudinal axis of proximal blood-carrying tubular structure, when the prosthesis is unconstrained in the radially-expanded state.

Inventive concept 88. The method according to inventive concept 87, wherein providing the endovascular prosthesis includes providing the endovascular prosthesis in which the average arc angle is at least 210 degrees.

Inventive concept 89. The method according to inventive concept 84, wherein providing the endovascular prosthesis includes providing the endovascular prosthesis in which the proximal circumferential structural strut members at least partially define the proximal blood-carrying tubular structure, when the prosthesis is unconstrained in the radially-expanded state.

Inventive concept 90. The method according to inventive concept 89, wherein providing the endovascular prosthesis includes providing the endovascular prosthesis in which, in addition to the proximal circumferential structural strut members, one or more others of the structural strut members are securely directly attached to the graft member and at least partially define the proximal blood-carrying tubular structure, when the prosthesis is unconstrained in the radially-expanded state.

Inventive concept 91. The method according to inventive concept 90, wherein providing the endovascular prosthesis includes providing the endovascular prosthesis in which the one or more other structural strut members include one or more circumferential structural strut members, which are disposed at respective longitudinal positions along the proximal blood-carrying tubular structure.

Inventive concept 92. The method according to inventive concept 84, wherein providing the endovascular prosthesis includes providing the endovascular prosthesis in which the contact circumferential portion of the proximal blood-carrying tubular structure is entirely circumferentially contiguous along at least a longitudinal portion of the proximal blood-carrying tubular structure, when the prosthesis is unconstrained in the radially-expanded state.

Inventive concept 93. The method according to inventive concept 84, wherein providing the endovascular prosthesis includes providing the endovascular prosthesis in which the contact circumferential portion of the proximal blood-carrying tubular structure is circumferentially non-contiguous along at least a longitudinal portion of the proximal blood-carrying tubular structure, when the prosthesis is unconstrained in the radially-expanded state.

Inventive concept 94. The method according to inventive concept 84, wherein providing the endovascular prosthesis includes providing the endovascular prosthesis in which an arc angle of the contact circumferential portion of the proximal blood-carrying tubular structure, measured about a central longitudinal axis of proximal blood-carrying tubular structure, is greater at a distal end of the proximal blood-carrying tubular structure than at a proximal end of the proximal blood-carrying tubular structure, when the prosthesis is unconstrained in the radially-expanded state.

Inventive concept 95. The method according to inventive concept 94, wherein providing the endovascular prosthesis includes providing the endovascular prosthesis in which the contact circumferential portion of the proximal blood-carrying tubular structure is circumferentially non-contiguous at at least the distal end of the proximal blood-carrying tubular structure, when the prosthesis is unconstrained in the radially-expanded state.

Inventive concept 96. The method according to inventive concept 95, wherein providing the endovascular prosthesis includes providing the endovascular prosthesis in which the contact circumferential portion of the proximal blood-carrying tubular structure is entirely circumferentially contiguous at at least the proximal end of the proximal blood-carrying tubular structure, when the prosthesis is unconstrained in the radially-expanded state.

Inventive concept 97. The method according to inventive concept 94, wherein providing the endovascular prosthesis includes providing the endovascular prosthesis in which the arc angle monotonically non-decreases from the proximal end to the distal end of the proximal blood-carrying tubular structure, when the prosthesis is unconstrained in the radially-expanded state.

Inventive concept 98. The method according to inventive concept 84, wherein providing the endovascular prosthesis includes providing the endovascular prosthesis in which:
the blood-vessel-fixation structure has an average unconstrained perimeter when the prosthesis is unconstrained in the radially-expanded state,
the proximal blood-carrying tubular structure includes a non-contact circumferential portion, which includes the entire proximal blood-carrying tubular structure circumference other than the contact circumferential portion of the proximal blood-carrying tubular structure, when the prosthesis is unconstrained in the radially-expanded state, and
an average spring constant of the structural strut members of the non-contact circumferential portion of the proximal blood-carrying tubular structure is no more than 90% of an average spring constant of the structural strut members of the contacting portion of the blood-vessel-fixation structure.

Inventive concept 99. The method according to inventive concept 84, wherein providing the endovascular prosthesis includes providing the endovascular prosthesis in which an average unconstrained perimeter of the blood-vessel-fixation structure is 70 to 130 mm, when the prosthesis is unconstrained in the radially-expanded state.

Inventive concept 100. The method according to inventive concept 84, wherein providing the endovascular prosthesis includes providing the endovascular prosthesis in which, when the prosthesis is unconstrained in the radially-expanded state:
the proximal blood-carrying tubular structure includes a non-contact circumferential portion, which includes the entire proximal blood-carrying tubular structure circumference other than the contact circumferential portion of the proximal blood-carrying tubular structure, and
an average graft surface area coverage of the non-contact circumferential portion of the proximal blood-carrying tubular structure is at least 90%.

Inventive concept 101. The method according to inventive concept 100, wherein providing the endovascular prosthesis includes providing the endovascular prosthesis in which the average graft surface area coverage of the non-contact circumferential portion of the proximal blood-carrying tubular structure is at least 95%, when the prosthesis is unconstrained in the radially-expanded state.

Inventive concept 102. The method according to inventive concept 50, wherein providing the endovascular prosthesis includes providing the endovascular prosthesis in which the proximal blood-carrying tubular structure and the blood-vessel-fixation structure include some of the same structural strut members, when the prosthesis is unconstrained in the radially-expanded state.

Inventive concept 103. The method according to inventive concept 102, wherein providing the endovascular prosthesis includes providing the endovascular prosthesis in which the proximal blood-carrying tubular structure includes, in addition to the some of the same structural strut members, others of the structural strut members, which are securely directly attached to the graft member and at least partially define the proximal blood-carrying tubular structure, when the prosthesis is unconstrained in the radially-expanded state.

There is still further provided, in accordance with an inventive concept 104 of the present invention, an endovascular system including:
a delivery sheath; and
an endovascular prosthesis, which (a) is removably disposed in the delivery sheath in a radially-compressed delivery state, (b) is configured to assume a radially-expanded state when unconstrained, and (c) includes:
- a stent-graft, which includes structural strut members and a graft member, wherein the structural strut members and the graft member are attached to each other and, when the endovascular prosthesis is unconstrained in the radially-expanded state, together are shaped so as to define a blood-carrying tubular structure defining a lumen; and
- an external coagulation inducer, which (a) is fixed to an external surface of the stent-graft both when the stent-graft is and is not removably disposed in the delivery sheath, and (h) includes a solid material, wherein, when the endovascular prosthesis is unconstrained in the radially-expanded state, (a) the external coagulation inducer is shaped so as to encompass at least a cube having an edge length of 3 mm and entirely filled with 216 sub-cubes, each of which has an edge length of 0.5 mm, (b) at least 50% of the sub-cubes contain some of the solid material of the external coagulation inducer, and (c) at least 10% of the volume of the cube is void of solid matter.

Inventive concept 105. The endovascular system according to inventive concept 104, wherein, when the endovascular prosthesis is unconstrained in the radially-expanded state, at least 85% of the sub-cubes contain some of the solid material of the external coagulation inducer.

Inventive concept 106. The endovascular system according to inventive concept 104, wherein at least 50% of the sub-cubes contain at least one external surface of the solid material of the external coagulation inducer, when the endovascular prosthesis is unconstrained in the radially-expanded state.

Inventive concept 107. The endovascular system according to inventive concept 106, wherein at least 70% of the sub-cubes contain at least one external surface of the solid material of the external coagulation inducer, when the endovascular prosthesis is unconstrained in the radially-expanded state.

Inventive concept 108. The endovascular system according to inventive concept 104, wherein, when the endovascular prosthesis is unconstrained in the radially-expanded state, (a) the external coagulation inducer is shaped so as to encompass at least a cube having an edge length of 4 mm and entirely filled with 512 sub-cubes, each of which has an edge length of 0.5 mm, and (b) at least 50% of the sub-cubes contain some of the solid material of the external coagulation inducer.

Inventive concept 109. The endovascular system according to inventive concept 108, wherein, when the endovascular prosthesis is unconstrained in the radially-expanded state, (a) the external coagulation inducer is shaped so as to encompass at least a cube having an edge length of 5 mm and entirely filled with 1000 sub-cubes, each of which has an edge length of 0.5 mm, and (b) at least 50% of the sub-cubes contain some of the solid material of the external coagulation inducer.

Inventive concept 110. The endovascular system according to inventive concept 104, wherein the solid material is shaped as one or more elongate members.

Inventive concept 111. The endovascular system according to inventive concept 110, wherein each of the elongate members includes a wire.

Inventive concept 112. The endovascular system according to inventive concept 110, wherein each of the elongate members includes a fiber.

Inventive concept 113. The endovascular system according to inventive concept 110, wherein each of the elongate members includes yarn, which includes interlocked fibers.

Inventive concept 114. The endovascular system according to inventive concept 104, wherein, when the endovascular prosthesis is unconstrained in the radially-expanded state, the external coagulation inducer extends along an axial length of the stent-graft equal to at least 1 cm.

Inventive concept 115. The endovascular system according to inventive concept 114, wherein the axial length is at least 2 cm.

Inventive concept 116. The endovascular system according to inventive concept 104, wherein, when the endovascular prosthesis is unconstrained in the radially-expanded state, the external coagulation inducer circumscribes one or more circumferential arcs having an aggregate angle measured about a central longitudinal axis of the stent-graft, the aggregate angle at least 25 degrees.

Inventive concept 117. The endovascular system according to inventive concept 116, wherein the aggregate angle is at least 50 degrees.

Inventive concept 118. The endovascular system according to inventive concept 117, wherein the aggregate angle is at least 90 degrees.

Inventive concept 119. The endovascular system according to inventive concept 118, wherein the aggregate angle is at least 180 degrees.

Inventive concept 120. The endovascular system according to inventive concept 119, wherein the aggregate angle is at least 300 degrees.

Inventive concept 121. The endovascular system according to inventive concept 116, wherein the one or more circumferential arcs include two or more non-contiguous circumferential arcs, when the endovascular prosthesis is unconstrained in the radially-expanded state.

Inventive concept 122. The endovascular system according to inventive concept 104, wherein, when the endovascular prosthesis is unconstrained in the radially-expanded state, the external coagulation inducer surrounds an entire circumference of the stent-graft.

Inventive concept 123. The endovascular system according to inventive concept 104, wherein the external coagulation inducer includes a plurality of non-contiguous external coagulation regions, when the endovascular prosthesis is unconstrained in the radially-expanded state.

Inventive concept 124. The endovascular system according to inventive concept 104, wherein, when the endovascular prosthesis is unconstrained in the radially-expanded state, the external coagulation inducer has a greatest radial dimension, measured radially outward from the external surface of the stent-graft, the greatest radial dimension at least 20% of a radius of the stent-graft at an axial location, along the stent-graft, of the greatest radial dimension.

Inventive concept 125. The endovascular system according to inventive concept 124, wherein the greatest radial dimension is at least 40% of the radius at the axial location.

Inventive concept 126. The endovascular system according to inventive concept 104, wherein, when the endovascular prosthesis is unconstrained in the radially-expanded state, the external coagulation inducer has a greatest radial dimension, measured radially outward from the external surface of the stent-graft, the greatest radial dimension at least 5 mm.

Inventive concept 127. The endovascular system according to inventive concept 126, wherein the greatest radial dimension is at least 7.5 mm.

Inventive concept 128. The endovascular system according to inventive concept 127, wherein the greatest radial dimension is at least 10 mm.

Inventive concept 129. The endovascular system according to inventive concept 104, wherein, when the endovascular prosthesis is unconstrained in the radially-expanded state, the stent-graft, at all axial locations therealong farther than respective distances from axial ends of the stent-graft, includes at least one circumferentially-contiguous circumferential arc free of all material more than 1 mm radially outward from an external surface of the graft member, wherein each of the respective distances is 5 mm, and wherein the circumferentially-contiguous circumferential arc has an angle measured about a central longitudinal axis of the stent-graft, the angle equal to at least 90 degrees.

Inventive concept 130. The endovascular system according to inventive concept 129, wherein the angle is at least 180 degrees.

Inventive concept 131. The endovascular system according to inventive concept 129, wherein each of the respective distances is 10 mm.

Inventive concept 132. The endovascular system according to inventive concept 104, wherein, when the endovascular prosthesis is unconstrained in the radially-expanded state, the external coagulation inducer is located farther than respective distances from axial ends of the stent-graft, each of the respective distance at least 5 mm.

Inventive concept 133. The endovascular system according to inventive concept 132, wherein each of the respective distances is at least 10 mm.

Inventive concept 134. The endovascular system according to inventive concept 104, wherein the stent-graft is shaped so as to define at least one fenestration, when the endovascular prosthesis is unconstrained in the radially-expanded state.

Inventive concept 135. The endovascular system according to inventive concept 104, wherein the stent-graft is a main stent-graft, and wherein the endovascular system further includes one or more branching stent-grafts.

There is additionally provided, in accordance with an inventive concept 136 of the present invention, an endovascular system including:

a delivery sheath; and an endovascular prosthesis, which (a) is removably disposed in the delivery sheath in a radially-compressed delivery state, (b) is configured to assume a radially-expanded state when unconstrained, and (c) includes:

a stent-graft, which includes structural strut members and a graft member, wherein the structural strut members and the graft member are attached to each other and, when the endovascular prosthesis is unconstrained in the radially-expanded state, together are shaped so as to define a blood-carrying tubular structure defining a lumen; and an external coagulation inducer, which includes a plurality of elongate coagulation members, each of which (a) is fixed, at at least one point along the elongate coagulation member, to an external surface of the stent-graft both when the stent-graft is and is not removably disposed in the delivery sheath, and (h) has a length of between 1 and 15 cm when the endovascular prosthesis is unconstrained in the radially-expanded state.

Inventive concept 137. The endovascular system according to inventive concept 136, wherein each of the elongate coagulation members includes one or more elongate members having a diameter of between 0.1 and 0.5 mm.

Inventive concept 138. The endovascular system according to inventive concept 137, wherein each of the elongate members includes a wire.

Inventive concept 139. The endovascular system according to inventive concept 137, wherein each of the elongate members includes a fiber.

Inventive concept 140. The endovascular system according to inventive concept 137, wherein each of the elongate members includes yarn, which includes interlocked fibers.

Inventive concept 141. The endovascular system according to inventive concept 136, wherein the elongate coagulation members are configured to self-curl to preset shapes when the endovascular prosthesis is unconstrained in the radially-expanded state.

Inventive concept 142. The endovascular system according to inventive concept 141, wherein the preset shapes are generally circular.

Inventive concept 143. The endovascular system according to inventive concept 141, wherein the preset shapes are generally helical.

Inventive concept 144. The endovascular system according to inventive concept 141, wherein the preset shapes are generally sinusoidal.

Inventive concept 145. The endovascular system according to inventive concept 141, wherein the preset shapes are generally spiral.

Inventive concept 146. The endovascular system according to inventive concept 141, wherein the preset shapes are generally amorphous.

Inventive concept 147. The endovascular system according to inventive concept 136, wherein each of the elongate coagulation members further includes of a plurality of coagulation-fibers, which are connected to the elongate coagulation member and distributed therealong.

Inventive concept 148. The endovascular system according to inventive concept 147, wherein the coagulation-fibers have an average diameter of between 0.01 and 0.1 mm.

Inventive concept 149. The endovascular system according to inventive concept 147, wherein coagulation-fibers have an average length of between 1 and 15 mm.

Inventive concept 150. The endovascular system according to inventive concept 136, wherein, when the endovascular prosthesis is unconstrained in the radially-expanded state, the external coagulation inducer extends along an axial length of the stent-graft equal to at least 1 cm.

Inventive concept 151. The endovascular system according to inventive concept 150, wherein the axial length is at least 2 cm.

Inventive concept 152. The endovascular system according to inventive concept 136, wherein the external coagulation inducer includes a plurality of non-contiguous external coagulation regions, when the endovascular prosthesis is unconstrained in the radially-expanded state.

Inventive concept 153. The endovascular system according to inventive concept 136, wherein, when the endovascular prosthesis is unconstrained in the radially-expanded state, the external coagulation inducer has a greatest radial dimension, measured radially outward from the external surface of the stent-graft, the greatest radial dimension at least 20% of a radius of the stent-graft at an axial location, along the stent-graft, of the greatest radial dimension.

Inventive concept 154. The endovascular system according to inventive concept 153, wherein the greatest radial dimension is at least 40% of the radius at the axial location.

Inventive concept 155. The endovascular system according to inventive concept 136, wherein, when the endovascular prosthesis is unconstrained in the radially-expanded state, the external coagulation inducer has a greatest radial dimension, measured radially outward from the external surface of the stent-graft, the greatest radial dimension at least 5 mm.

Inventive concept 156. The endovascular system according to inventive concept 155, wherein the greatest radial dimension is at least 7.5 mm.

Inventive concept 157. The endovascular system according to inventive concept 156, wherein the greatest radial dimension is at least 10 mm.

Inventive concept 158. The endovascular system according to inventive concept 136, wherein, when the endovascular prosthesis is unconstrained in the radially-expanded state, the external coagulation inducer circumscribes one or more circumferential arcs having an aggregate angle measured about a central longitudinal axis of the stent-graft, the aggregate angle at least 90 degrees.

Inventive concept 159. The endovascular system according to inventive concept 158, wherein the aggregate angle is at least 180 degrees.

Inventive concept 160. The endovascular system according to inventive concept 159, wherein the aggregate angle is at least 300 degrees.

Inventive concept 161. The endovascular system according to inventive concept 158, wherein the one or more circumferential arcs include two or more circumferential arcs, when the endovascular prosthesis is unconstrained in the radially-expanded state.

Inventive concept 162. The endovascular system according to inventive concept 136, wherein, when the endovascular prosthesis is unconstrained in the radially-expanded state, the external coagulation inducer surrounds an entire circumference of the stent-graft.

Inventive concept 163. The endovascular system according to inventive concept 136,
wherein, when the endovascular prosthesis is unconstrained, in the radially-expanded state, the stent-graft, at all axial locations therealong farther than respective distances from axial ends of the stent-graft, includes at least one circumferentially-contiguous circumferential arc free of all material more than 1 mm radially outward from an external surface of the graft member,
wherein each of the respective distances is 5 mm, and
wherein the circumferentially-contiguous circumferential arc has an angle measured about a central longitudinal axis of the stent-graft, the angle equal to at least 90 degrees.

Inventive concept 164. The endovascular system according to inventive concept 163, wherein the angle is at least 180 degrees.

Inventive concept 165. The endovascular system according to inventive concept 163, wherein each of the respective distances is 10 mm.

Inventive concept 166. The endovascular system according to inventive concept 136, wherein, when the endovascular prosthesis is unconstrained in the radially-expanded state, the external coagulation inducer is located farther than respective distances from axial ends of the stent-graft, each of the respective distance at least 5 mm.

Inventive concept 167. The endovascular system according to inventive concept 166, wherein each of the respective distances is at least 10 mm.

Inventive concept 168. The endovascular system according to inventive concept 136, wherein the stent-graft is shaped so as to define at least one fenestration, when the endovascular prosthesis is unconstrained in the radially-expanded state.

Inventive concept 169. The endovascular system according to inventive concept 136, wherein the stent-graft is a main stent-graft, and wherein the endovascular system further includes one or more branching stent-grafts.

There is yet additionally provided, in accordance with an inventive concept 170 of the present invention, an endovascular system including:
  a delivery sheath; and
  an endovascular prosthesis, which (a) is removably disposed in the delivery sheath in a radially-compressed delivery state, (b) is configured to assume a radially-expanded state when unconstrained, and (c) includes:
    a stent-graft, which includes structural strut members and a graft member, wherein the structural strut members and the graft member are attached to each other and, when the endovascular prosthesis is unconstrained in the radially-expanded state, together are shaped so as to define a blood-carrying tubular structure defining a lumen; and
    an external coagulation inducer, which includes one or more scales-segment members, each of which (a) includes a plurality of scales, (b) is fixed, at at least one point along the scales-segment member, to an external surface of the stent-graft both when the stent-graft is and is not removably disposed in the delivery sheath, and (c) extends around at least 20 mm of a circumference of the stent-graft, wherein the scales extend, on average, around at least 5 mm of the circumference of the stent-graft.

Inventive concept 171. The endovascular system according to inventive concept 170, wherein at least one of the scales is open proximally and attached to the external surface of the stent-graft at a distal portion of the scale.

Inventive concept 172. The endovascular system according to inventive concept 170, wherein the scales are configured to assume a radially-compressed state and a radially-expanded state.

Inventive concept 173. The endovascular system according to inventive concept 170, wherein each of the scales includes a scale structural member and a scale graft member, and wherein the scale structural member is biased to increase an effective radial extent of the scale when the scale is radially unconstrained.

Inventive concept 174. The endovascular system according to inventive concept 173, wherein the scale structural member includes a self-expandable wire.

Inventive concept 175. The endovascular system according to inventive concept 170, wherein a planar shape of each of one or more of the scales is a triangle with a proximally-facing base.

Inventive concept 176. The endovascular system according to inventive concept 170, wherein a planar shape of each of one or more of the scales is a deltoid with proximally, distally, and laterally oriented vertices.

Inventive concept 177. The endovascular system according to inventive concept 170, wherein a planar shape of each of one or more of the scales-segment members is a rectangle.

Inventive concept 178. The endovascular system according to inventive concept 170, wherein a planar shape of each of one or more of the scales-segment members is a parallelogram.

Inventive concept 179. The endovascular system according to inventive concept 170, wherein an average radial extent of the scales, when radially expanded, is at least 3 millimeters.

Inventive concept 180. The endovascular system according to inventive concept 170, wherein, when the endovascular prosthesis is unconstrained in the radially-expanded state, at least one of the scales-segment members, taken alone, circumscribes an arc having an angle of at least 50 degrees.

Inventive concept 181. The endovascular system according to inventive concept 170, wherein, when the endovascular prosthesis is unconstrained in the radially-expanded state, the external coagulation inducer extends along an axial length of the stent-graft equal to at least 1 cm.

Inventive concept 182. The endovascular system according to inventive concept 181, wherein the axial length is at least 2 cm.

Inventive concept 183. The endovascular system according to inventive concept 170, wherein, when the endovascular prosthesis is unconstrained in the radially-expanded state, the external coagulation inducer has a greatest radial dimension, measured radially outward from the external surface of the stent-graft, the greatest radial dimension at least 20% of a radius of the stent-graft at an axial location, along the stent-graft, of the greatest radial dimension.

Inventive concept 184. The endovascular system according to inventive concept 183, wherein the greatest radial dimension is at least 40% of the radius at the axial location.

Inventive concept 185. The endovascular system according to inventive concept 170, wherein, when the endovascular prosthesis is unconstrained in the radially-expanded state, the external coagulation inducer has a greatest radial dimension, measured radially outward from the external surface of the stent-graft, the greatest radial dimension at least 5 mm.

Inventive concept 186. The endovascular system according to inventive concept 185, wherein the greatest radial dimension is at least 7.5 mm.

Inventive concept 187. The endovascular system according to inventive concept 186, wherein the greatest radial dimension is at least 10 mm.

Inventive concept 188. The endovascular system according to inventive concept 170, wherein, when the endovascular prosthesis is unconstrained in the radially-expanded state, the external coagulation inducer circumscribes one or more circumferential arcs having an aggregate angle measured about a central longitudinal axis of the stent-graft, the aggregate angle at least 90 degrees.

Inventive concept 189. The endovascular system according to inventive concept 188, wherein the aggregate angle is at least 180 degrees.

Inventive concept 190. The endovascular system according to inventive concept 189, wherein the aggregate angle is at least 300 degrees.

Inventive concept 191. The endovascular system according to inventive concept 188, wherein the one or more circumferential arcs include two or more circumferential arcs.

Inventive concept 192. The endovascular system according to inventive concept 170, wherein, when the endovascular prosthesis is unconstrained in the radially-expanded state, the stent-graft, at all axial locations therealong farther than respective distances from axial ends of the stent-graft, includes at least one circumferentially-contiguous circumferential arc free of all material more than 1 mm radially outward from an external surface of the graft member,
wherein each of the respective distances is 0.5 mm, and
wherein the circumferentially-contiguous circumferential arc has an angle measured about a central longitudinal axis of the stent-graft, the angle equal to at least 90 degrees.

Inventive concept 193. The endovascular system according to inventive concept 192, wherein the angle is at least 180 degrees.

Inventive concept 194. The endovascular system according to inventive concept 192, wherein each of the respective distances is 10 mm.

Inventive concept 195. The endovascular system according to inventive concept 170, wherein, when the endovascular prosthesis is unconstrained in the radially-expanded state, the external coagulation inducer is located farther than respective distances from axial ends of the stent-graft, each of the respective distance at least 5 mm.

Inventive concept 196. The endovascular system according to inventive concept 195, wherein each of the respective distances is at least 10 mm.

Inventive concept 197. The endovascular system according to inventive concept 170, wherein the stent-graft is shaped so as to define at least one fenestration.

Inventive concept 198. The endovascular system according to inventive concept 170, wherein the stent-graft is a main stent-graft, and wherein the endovascular system further includes one or more branching stent-grafts.

There is also provided, in accordance with an inventive concept 199 of the present invention, an endovascular system including:
a delivery sheath; and
an endovascular prosthesis, which (a) is removably disposed in the delivery sheath in a radially-compressed delivery state, (b) is configured to assume a radially-expanded state when unconstrained, and (c) includes:
  a stent-graft, which includes structural strut members and a graft member, wherein the structural strut members and the graft member are attached to each other and, when the endovascular prosthesis is unconstrained in the radially-expanded state, together are shaped so as to define a blood-carrying tubular structure defining a lumen; and
  an external coagulation inducer, which includes an extra-luminal skirt, which (a) includes a fiber mesh, wherein at least 50% of an outer surface of the fiber mesh is not covered with graft material, and (b) is configured to assume (i) when the endovascular prosthesis is removably disposed in the delivery sheath, a radially-compressed delivery state, and (ii) when the endovascular prosthesis is unconstrained, a radially-expanded state, in which the extra-luminal skirt extends radially outward from an external surface of the stent-graft.

Inventive concept 200. The endovascular system according to inventive concept 199, wherein 100% of the outer surface of the fiber mesh is not covered with graft material.

Inventive concept 201. The endovascular system according to inventive concept 199, wherein the extra-luminal skirt further includes graft material, which covers less than 50% of the outer surface of the fiber mesh.

Inventive concept 202. The endovascular system according to inventive concept 199, wherein the extra-luminal skirt monotonically widens along an entire length of the extra-luminal skirt, when the endovascular prosthesis is unconstrained in the radially-expanded state.

Inventive concept 203. The endovascular system according to inventive concept 202, wherein the extra-luminal skirt monotonically widens in a proximal-to-distal direction along an entire length of the extra-luminal skirt, when the endovascular prosthesis is unconstrained in the radially-expanded state.

Inventive concept 204. The endovascular system according to inventive concept 199, wherein the extra-luminal skirt (a) widens in a proximal-to-distal direction to a longitudinal location having a greatest skirt outer cross-sectional area, and (b) narrows in a proximal-to-distal direction from the longitudinal location having the greatest skirt outer cross-sectional area, when the endovascular prosthesis is unconstrained in the radially-expanded state.

Inventive concept 205. The endovascular system according to inventive concept 199, wherein the extra-luminal skirt completely circumferentially encircles the stent-graft.

Inventive concept 206. The endovascular system according to inventive concept 199, wherein a greatest external perimeter of the extra-luminal skirt equals at least 110% of a greatest external perimeter of the stent-graft, when the endovascular prosthesis is unconstrained in the radially-expanded state.

Inventive concept 207. The endovascular system according to inventive concept 199, wherein the extra-luminal skirt adds less than 30% to a diameter of the stent-graft when the endovascular prosthesis is removably disposed in the delivery sheath in the radially-compressed delivery state.

Inventive concept 208. The endovascular system according to inventive concept 207, wherein the extra-luminal skirt adds less than 20% to the diameter of the stent-graft when the endovascular prosthesis is removably disposed in the delivery sheath in the radially-compressed delivery state.

Inventive concept 209. The endovascular system according to inventive concept 199, wherein the fiber mesh includes Nitinol.

Inventive concept 210. The endovascular system according to inventive concept 199, wherein the fiber mesh includes a polymer coating.

Inventive concept 211. The endovascular system according to inventive concept 199, wherein the fiber mesh includes braided fibers.

Inventive concept 212. The endovascular system according to inventive concept 199, wherein the fiber mesh includes fibers that are arranged to slide with respect to each other so as to cause a change in outer diameter of the extra-luminal skirt.

Inventive concept 213. The endovascular system according to inventive concept 199, wherein the fiber mesh is arranged such that a change in an axial length of the extra-luminal skirt causes a change in an outer diameter of the extra-luminal skirt.

Inventive concept 214. The endovascular system according to inventive concept 199, wherein the stent-graft is a main stent-graft, and wherein the endovascular system further includes one or more branching stent-grafts.

There is further provided, in accordance with an inventive concept 215 of the present invention, an endovascular system including:
 a delivery sheath; and
 an endovascular prosthesis, which (a) is removably disposed in the delivery sheath in a radially-compressed delivery state, (b) is configured to assume a radially-expanded state when unconstrained, (c) includes structural strut members and a graft member, and (d) includes:
  a stent-graft, which includes a first portion of the structural strut members and a first portion of the graft member, wherein the structural strut members of the first portion and the graft member of the first portion are attached to each other and, when the endovascular prosthesis is unconstrained in the radially-expanded state, together are shaped so as to define a blood-carrying tubular structure defining a lumen; and
  an external coagulation inducer, which includes an extra-luminal skirt, which (a) includes a second portion of the structural strut members and a second portion of the graft member, and (b) is configured to assume:
   (i) when the endovascular prosthesis is removably disposed in the delivery sheath, a radially-compressed delivery state, in which the structural strut members of the first portion do not coincide with the structural stent members of the second portion, and
   (ii) when the endovascular prosthesis is unconstrained, a radially-expanded state, in which the extra-luminal skirt extends radially outward from an external surface of the stent-graft.

Inventive concept 216. The endovascular system according to inventive concept 215, wherein the extra-luminal skirt monotonically widens along an entire length of the extra-luminal skirt, when the endovascular prosthesis is unconstrained in the radially-expanded state.

Inventive concept 217. The endovascular system according to inventive concept 216, wherein the extra-luminal skirt monotonically widens in a distal-to-proximal direction along an entire length of the extra-luminal skirt, when the endovascular prosthesis is unconstrained in the radially-expanded state.

Inventive concept 218. The endovascular system according to inventive concept 216, wherein the extra-luminal skirt monotonically widens in a proximal-to-distal direction along an entire length of the extra-luminal skirt, when the endovascular prosthesis is unconstrained in the radially-expanded state.

Inventive concept 219. The endovascular system according to inventive concept 215, wherein when the endovascular prosthesis is unconstrained in the radially-expanded state, the structural strut members of the second portion extend radially outward from the external surface of the stent-graft at an angle of between 30 and 40 degrees with the external surface.

Inventive concept 220. The endovascular system according to inventive concept 215, wherein the extra-luminal skirt completely circumferentially encircles the stent-graft.

Inventive concept 221. The endovascular system according to inventive concept 215, wherein a greatest external perimeter of the extra-luminal skirt equals at least 110% of a greatest external perimeter of the stent-graft, when the endovascular prosthesis is unconstrained in the radially-expanded state.

Inventive concept 222. The endovascular system according to inventive concept 215, wherein the stent-graft is a main stent-graft, and wherein the endovascular system further includes one or more branching stent-grafts.

Inventive concept 223. The endovascular system according to any one of inventive concepts 215-222,
 wherein the extra-luminal skirt is a first extra-luminal skirt, and
 wherein the external coagulation inducer further includes a second extra-luminal skirt, which (a) includes a third portion of the structural strut members and a third portion of the graft member, and (b) is configured to assume:
  (i) when the endovascular prosthesis is removably disposed in the delivery sheath, a radially-compressed delivery state, in which the structural strut members of the first portion do not coincide with the structural stent members of the third portion, and (ii) when the endovascular prosthesis is unconstrained, a radially-expanded state, in which the second extra-luminal skirt extends radially outward from the external surface of the stent-graft.

Inventive concept 224. The endovascular system according to inventive concept 223, wherein the first extra-luminal skirt is disposed proximally to the second extra-luminal skirt, and wherein when the endovascular prosthesis is unconstrained in the radially-expanded state:

the first extra-luminal skirt monotonically widens in a distal-to-proximal direction along an entire length of the first extra-luminal skirt, and the second extra-luminal skirt monotonically widens in a proximal-to-distal direction along an entire length of the second extra-luminal skirt.

Inventive concept 225. The endovascular system according to inventive concept 223, wherein the first extra-luminal skirt is disposed proximally to the second extra-luminal skirt, and wherein when the endovascular prosthesis is unconstrained in the radially-expanded state:

the first extra-luminal skirt monotonically widens in a distal-to-proximal direction along an entire length of the first extra-luminal skirt, and the second extra-luminal skirt monotonically widens in the distal-to-proximal direction along an entire length of the second extra-luminal skirt.

Inventive concept 226. The endovascular system according to any one of inventive concepts 215-222, wherein the structural strut members of the second portion are directly connected to the structural strut members of the first portion, wherein none of the structural strut members of the second portion is directly connected to any of the other structural strut members of the second portion, and wherein none of the structural strut members of the second portion is indirectly connected to any of the other structural strut members of the second portion other than via one or more of the structural strut members of the first portion.

Inventive concept 227. The endovascular system according to any one of inventive concepts 215-222, wherein the structural strut members of the second portion are thinner on average than the structural strut members of the first portion.

Inventive concept 228. The endovascular system according to any one of inventive concepts 215-222, wherein the extra-luminal skirt adds less than 30% to a diameter of the stent-graft when the endovascular prosthesis is removably disposed in the delivery sheath in the radially-compressed delivery state.

Inventive concept 229. The endovascular system according to inventive concept 228, wherein the extra-luminal skirt adds less than 20% to the diameter of the stent-graft when the endovascular prosthesis is removably disposed in the delivery sheath in the radially-compressed delivery state.

There is further provided, in accordance with an inventive concept 230 of the present invention, a method including:

advancing, into a main artery of a subject, an endovascular prosthesis, which is removably disposed in a delivery sheath in a radially-compressed delivery state, and includes (a) structural strut members and a graft member, (b) a main stent-graft, which includes a first portion of the structural strut members and a first portion of the graft member, wherein the structural strut members of the first portion and the graft member of the first portion are attached to each other, and (c) an external coagulation inducer, which includes an extra-luminal skirt, which includes a second portion of the structural strut members and a second portion of the graft member, wherein, when the endovascular prosthesis is removably disposed in the delivery sheath, the external coagulation inducer assumes a radially-compressed delivery state, in which the structural strut members of the first portion do not coincide with the structural stent members of the second portion; and deploying the endovascular prosthesis from the delivery sheath such that (a) the endovascular prosthesis assumes a radially-expanded state in which the first portion of the structural strut members and the first portion of the graft member together are shaped so as to define a blood-carrying tubular structure defining a lumen, and (b) the extra-luminal skirt assumes a radially-expanded state, in which the extra-luminal skirt extends radially outward from an external surface of the stent-graft.

Inventive concept 231. The method according to inventive concept 230, further including deploying one or more branching stent-grafts partially alongside the main stent-graft and partially in respective branching arteries that branch from the main artery, such that portions of the branching stent-grafts contact the extra-luminal skirt.

There is additionally provided, in accordance with an inventive concept 232 of the present invention, an endovascular system including:

an anti-gutter linking endovascular prosthesis, which is configured to assume a radially-expanded state, and which includes:

structural strut members and a graft member, which are attached to each other; and an internal coagulation inducer, which is fixed to an internal surface of a lumen defined by the anti-gutter linking endovascular prosthesis; and a branching stent-graft and a main stent-graft, which is larger than the branching stent-graft, wherein the main and the branching stent-grafts are configured to assume respective radially-expanded state, wherein the branching stent-graft, the main stent-graft, the anti-gutter linking endovascular prosthesis, and the internal coagulation inducer are sized such that the branching stent-graft and the main stent-graft are disposable alongside each other passing through the internal coagulation inducer of the anti-gutter linking endovascular prosthesis, when the branching stent-graft, the main stent-graft, and the anti-gutter linking endovascular prosthesis are in their respective radially-expanded states.

Inventive concept 233. The endovascular system according to inventive concept 232, wherein the internal coagulation inducer includes a solid material, and wherein, when the anti-gutter linking endovascular prosthesis is unconstrained in its radially-expanded state, (a) the internal coagulation inducer is shaped so as to encompass at least a cube having an edge length of 3 mm and entirely filled with 216 sub-cubes, each of which has an edge length of 0.5 mm, (h) at least 50% of the sub-cubes contain some of the solid material of the internal coagulation inducer, and (c) at least 10% of the volume of the cube is void of solid matter.

Inventive concept 234. The endovascular system according to inventive concept 232, wherein the internal coagulation inducer includes a plurality of elongate coagulation members, each of which (a) is fixed, at at least one point along the elongate coagulation member, to the internal surface of the lumen defined by the anti-gutter linking endovascular prosthesis, and (h) has a length of between 1 and 15 cm when the anti-gutter linking endovascular prosthesis is unconstrained in its radially-expanded state.

Inventive concept 235. The endovascular system according to inventive concept 232, wherein the internal coagulation inducer includes one or more scales-segment members, each of which (a) includes a plurality of scales. (h) is fixed, at at least one point along the scales-segment member, to the internal surface of the lumen defined by the anti-gutter linking endovascular prosthesis, and (c) extends around at least 30 mm of a circumference of the lumen defined by the anti-gutter linking endovascular prosthesis, wherein the scales extend, on average, around at least 5 mm of the circumference of the lumen defined by the anti-gutter linking endovascular prosthesis.

Inventive concept 236. The endovascular system according to inventive concept 232, wherein the internal coagulation inducer includes an intra-luminal skirt, which (a) includes a fiber mesh, wherein at least 50% of an outer surface of the fiber mesh is not covered with graft material, and (b) is configured to assume a radially-expanded state, in which the intra-luminal skirt extends radially inward from the internal surface of the lumen defined by the anti-gutter linking endovascular prosthesis, when the anti-gutter linking endovascular prosthesis is unconstrained in its radially-expanded state.

Inventive concept 237. The endovascular system according to inventive concept 232, wherein the internal coagulation inducer includes an intra-luminal skirt, which (a) includes a portion of the structural strut members and a portion of the graft member, and (b) is configured to assume a radially-expanded state, in which the intra-luminal skirt extends radially inward from the internal surface of the lumen defined by the anti-gutter linking endovascular prosthesis, when the anti-gutter linking endovascular prosthesis is unconstrained in its radially-expanded state.

There is still further provided, in accordance with an inventive concept 238 of the present invention, a method including:

advancing, into a main artery of a subject, an endovascular prosthesis, which is removably disposed in a delivery sheath in a radially-compressed delivery state, and includes (a) a main stent-graft, which includes structural strut members and a graft member that are attached to each other, and (h) an external coagulation inducer, which is fixed to an external surface of the main stent-graft;

deploying the endovascular prosthesis from the delivery sheath such that the endovascular prosthesis assumes a radially-expanded state in which the structural strut members and the graft member together are shaped so as to define a blood-carrying tubular structure defining a lumen; and deploying one or more branching stent-grafts partially alongside the main stent-graft and partially in respective branching arteries that branch from the main artery, such that portions of the branching stent-grafts contact the external coagulation inducer.

Inventive concept 239. The method according to inventive concept 238, wherein, when the endovascular prosthesis is unconstrained in the radially-expanded state, the external coagulation inducer has a greatest radial dimension, measured radially outward from the external surface of the main stent-graft, the greatest radial dimension at least 3 mm.

Inventive concept 240. The method according to inventive concept 238, wherein the external coagulation inducer includes a solid material, and wherein, when the endovascular prosthesis is unconstrained in its radially-expanded state, (a) the external coagulation inducer is shaped so as to encompass at least a cube having an edge length of 3 mm and entirely filled with 216 sub-cubes, each of which has an edge length of 0.5 mm, (b) at least 50% of the sub-cubes contain some of the solid material of the external coagulation inducer, and (c) at least 10% of the volume of the cube is void of solid matter.

Inventive concept 241. The method according to inventive concept 238, wherein the external coagulation inducer includes a plurality of elongate coagulation members, each of which (a) is fixed, at at least one point along the elongate coagulation member, to the external surface of the lumen defined by the endovascular prosthesis, and (b) has a length of between 1 and 15 cm when the endovascular prosthesis is unconstrained in its radially-expanded state.

Inventive concept 242. The method according to inventive concept 238, wherein the external coagulation inducer includes one or more scales-segment members, each of which (a) includes a plurality of scales, (b) is fixed, at at least one point along the scales-segment member, to the external surface of the lumen defined by the endovascular prosthesis, and (c) extends around at least 30 mm of a circumference of the lumen defined by the endovascular prosthesis, wherein the scales extend, on average, around at least 5 mm of the circumference of the lumen defined by the endovascular prosthesis.

Inventive concept 243. The method according to inventive concept 238, wherein the external coagulation inducer includes an extra-luminal skirt, which (a) includes a fiber mesh, wherein at least 50% of an outer surface of the fiber mesh is not covered with graft material, and (b) is configured to assume a radially-expanded state, in which the extra-luminal skirt extends radially outward from the external surface of the lumen defined by the endovascular prosthesis, when the endovascular prosthesis is unconstrained in its radially-expanded state.

Inventive concept 244. The method according to inventive concept 238, wherein the structural strut members of the main stent-graft are a first portion of structural strut members of the endovascular prosthesis, and the graft member of the main stent-graft is a first portion of a graft member of the endovascular prosthesis, and wherein the external coagulation inducer includes an extra-luminal skirt, which (a) includes a second portion of the structural strut members and a second portion of the graft member, and (b) is configured to assume a radially-expanded state, in which the extra-luminal skirt extends radially outward from the external surface of the lumen defined by the endovascular prosthesis, when the endovascular prosthesis is unconstrained in its radially-expanded state.

Inventive concept 245. The method according to inventive concept 244, wherein the extra-luminal skirt, which is configured to assume, when the endovascular prosthesis is removably disposed in the delivery sheath, a radially-compressed delivery state, in which the structural strut members of the first portion do not coincide with the structural stent members of the second portion.

There is additionally provided, in accordance with an inventive concept 246 of the present invention, a method including:

advancing, into a main artery of a subject, an anti-gutter linking endovascular prosthesis, which is removably disposed in a delivery sheath in a radially-compressed delivery state, and includes (a) structural strut members and a graft member, which are attached to each other, and (b) an internal coagulation inducer, which is fixed to an internal surface of a lumen defined by the anti-gutter linking endovascular prosthesis;

deploying the anti-gutter linking endovascular prosthesis from the delivery sheath such that the anti-gutter linking endovascular prosthesis assumes a radially-expanded state:

deploying a branching stent-graft passing through the anti-gutter linking endovascular prosthesis and partially disposed in a branching artery that branches from the main artery, such that the branching stent-graft assumes a radially-expanded state; and deploying a main stent-graft in the main artery passing through the anti-gutter linking endovascular prosthesis, such that the main stent-graft assumes a radially-expanded state, the main stent-graft larger than the branching stent-graft, such that the main stent-graft and the branching stent-graft are disposed alongside each other passing through the internal coagulation inducer of the anti-gutter linking endovascular prosthesis, with portions of the main stent-graft and the branching stent-graft touching the internal coagulation inducer.

There is yet additionally provided, in accordance with an inventive concept 247 of the present invention, an endovascular prosthesis, including:

a stent-graft; and an external coagulation inducer, which includes first and second extra-luminal skirts, which (a) include respective structural strut members and respective portions of a graft member, and (h) are configured to assume, when the endovascular prosthesis is unconstrained, respective radially-expanded states, in which the first and the second extra-luminal skirts extend radially outward from an external surface of the stent-graft, wherein, when in the respective radially-expanded states, the first and the second extra-luminal skirts monotonically widen in a same axial direction along respective entire lengths of the first and the second extra-luminal skirts.

The present invention will be more fully understood from the following detailed description of embodiments thereof, taken together with the drawings, in which:

BRIEF DESCRIPTION OF THE DRAWINGS

FIGS. 4A-B are schematic illustrations of additional configurations of a distal skirt longitudinal portion of the endovascular prosthesis of FIGS. 1 and 2A, in accordance with respective applications of the present invention;

FIGS. 5A-C are schematic illustrations of a multi-component endovascular system, in accordance with respective applications of the present invention;

FIGS. 6A-B are schematic illustrations of two stages of an exemplary transvascular delivery procedure for deploying the endovascular system of FIGS. 5A-B in an aneurysmal descending aorta, in accordance with an application of the present invention;

FIGS. 9A-C are schematic illustrations of three stages of an exemplary transvascular delivery procedure for deploying the endovascular system of FIG. 18 in an aneurysmal aortic arch, in accordance with an application of the present invention.

DETAILED DESCRIPTION OF APPLICATIONS

Figure 1:
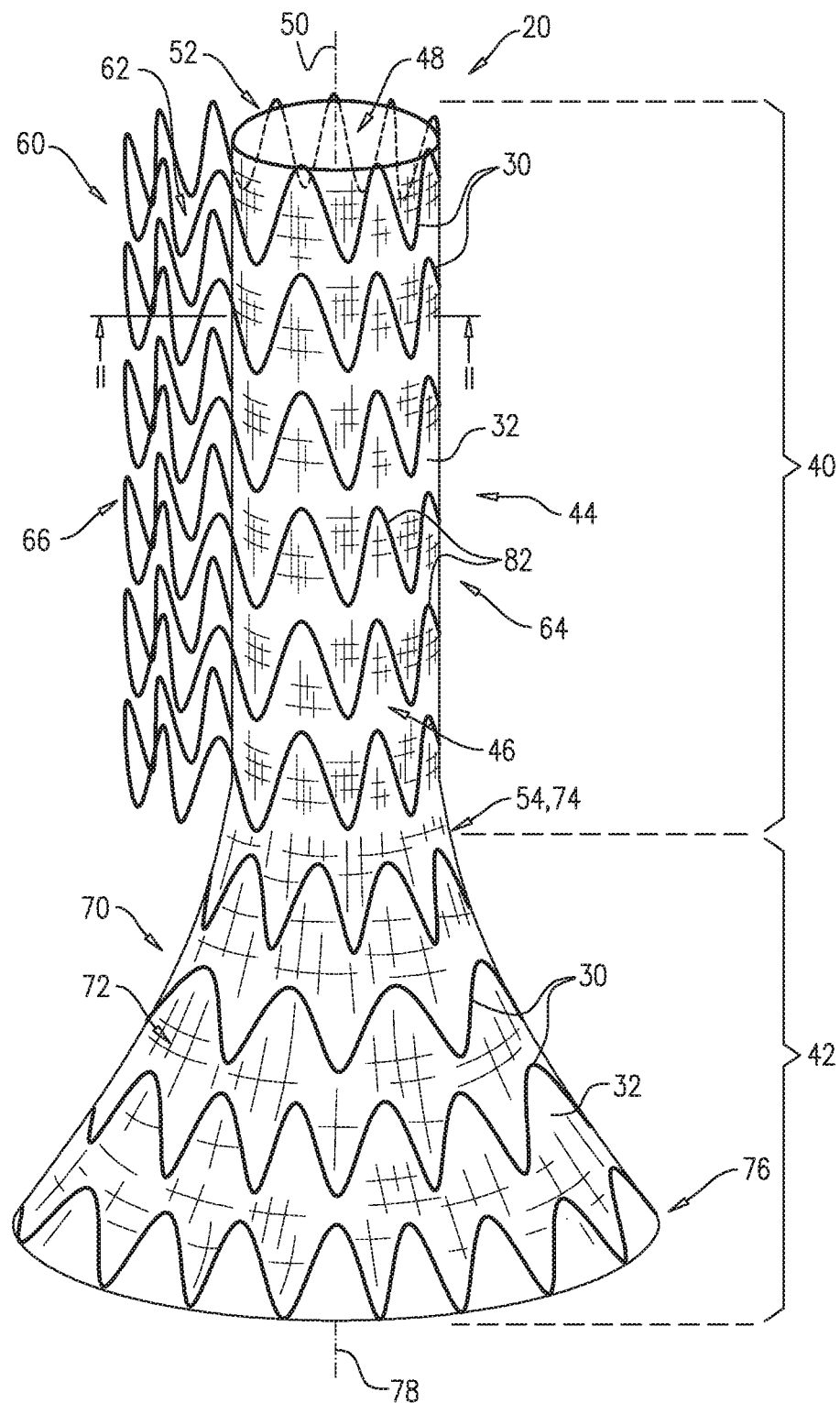
FIG. 1 is a schematic illustration of an endovascular prosthesis, in accordance with an application of the present invention.
Figure 2A:
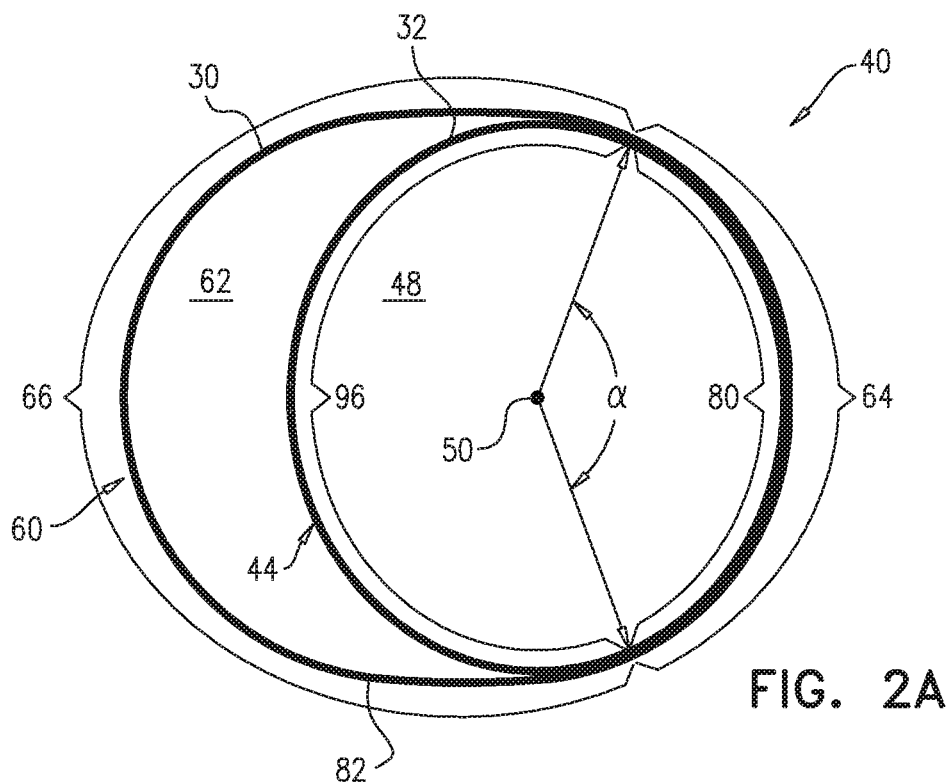
FIG. 2A is a schematic cross-sectional view of a proximal branch-enabling longitudinal portion of the endovascular prosthesis of FIG. 1, taken along the line 11 II of FIG. 1, in accordance with an application of the present invention.
Figure 2B:
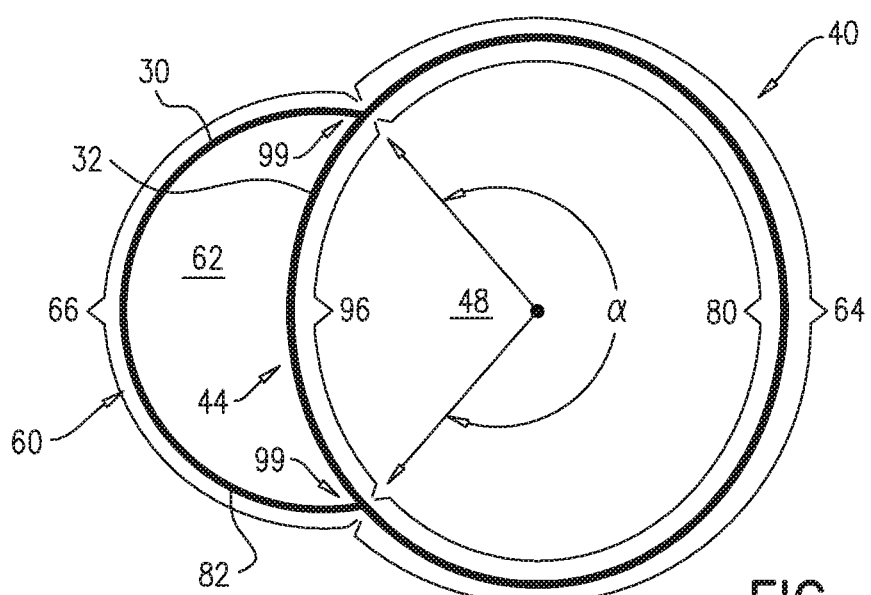
FIG. 2B is a schematic cross-sectional view of another configuration of the proximal branch-enabling longitudinal portion, in accordance with an application of the present invention.

FIG. 1 is a schematic illustration of an endovascular prosthesis 20, in accordance with an application of the present invention. Prosthesis 20 is configured to transition from a radially-compressed delivery state to a radially-expanded state, and is shown in the radially-expanded state in FIG. 1 (as well as in FIGS. 2A-B, 3A-C. 4A-B, and 5A-C). Prosthesis 20 is typically self-expanding, i.e., is configured to automatically transition from the radially-compressed delivery state to the radially-expanded state, such as upon being released from a delivery tube. Prosthesis 20 comprises structural strut members 30 and a graft member 32. Prosthesis 20 is shaped so as to define a proximal branch-enabling longitudinal portion 40, and, typically, but not necessarily, a distal skirt longitudinal portion 42. FIG. 2A is a schematic cross-sectional view of proximal branch-enabling longitudinal portion 40, taken along the line II-II of FIG. 1, in accordance with an application of the present invention. FIG. 2B is a schematic cross-sectional view of another configuration of proximal branch-enabling longitudinal portion 40, in accordance with an application of the present invention. Endovascular prosthesis 20 may be provided as part of an endovascular system, which may additionally comprise other components, such as a delivery tool (e.g., comprising a catheter), and/or other endovascular stent-grafts, such as described hereinbelow with reference to FIGS. 5A-C and/or 6A-B. Alternatively, the endovascular system may comprise only endovascular prosthesis 20.

Proximal branch-enabling longitudinal portion 40 comprises a proximal blood-carrying tubular structure 44 and a blood-vessel-fixation structure 60.

Proximal blood-carrying tubular structure 44 is typically is self-expanding, i.e., is configured to automatically expand during the transition of prosthesis 20 from the radially-compressed delivery state to the radially-expanded state, such as upon being released from a delivery tube, and:
  comprises a proximal portion 46 of graft member 32 and some of structural strut members 30, which are fixed to proximal portion 46 of graft member 32 (on the inside and/or the outside of graft member 32) so as to provide a proximal blood-carrying lumen 48 through proximal blood-carrying tubular structure 44, when prosthesis 20 is unconstrained in the radially-expanded state, and
  when prosthesis 20 is unconstrained in the radially-expanded state, has an average proximal-blood-carrying inner cross-sectional area, a central longitudinal axis 50, and proximal and distal ends 52 and 54.

Blood-vessel-fixation structure 60 (a) comprises some of structural strut members 30, and (b) when prosthesis 20 is unconstrained in the radially-expanded state:
  defines a structurally-supported space 62 alongside and external to proximal blood-carrying tubular structure 44, along the entire proximal branch-enabling longitudinal portion 40,
  includes a contacting portion 64, which directly contacts proximal blood-carrying tubular structure 44, and which, at a plurality of locations of contacting portion 64, is directly fixed to proximal blood-carrying tubular structure 44, such as by stitching (it is noted that contacting portion 64 is typically directly fixed to proximal blood-carrying tubular structure 44 at only a portion of contacting portion 64, i.e., at the plurality of locations of contacting portion 64), and
  includes a non-contacting portion 66, which does not directly contact proximal blood-carrying tubular structure 44, and which has an average graft surface area coverage of less than 20%, such as less than 10%, or less than 5%, e.g., 0%.

The average proximal-blood-carrying inner cross-sectional area is measured perpendicular to central longitudinal axis 50, and is defined by an inner surface of proximal blood-carrying tubular structure 44. As used in the present application, including in the claims, an average cross-sectional area of a tubular structure (whether an inner or an outer cross-sectional area) is the average cross-sectional area of the tubular structure, measured perpendicular to the central longitudinal axis thereof along the length of the tubular structure. Prosthesis 20 is "unconstrained" when no constraining forces are applied to the prosthesis by a deployment tool (such as a delivery shaft in which prosthesis 20 is disposed), anatomy of the subject (such as the wall of a blood vessel, e.g., the aorta), or otherwise. Blood-vessel-fixation structure 60 is optionally self-expanding, i.e., is configured to automatically expand during the transition of prosthesis 20 from the radially-compressed delivery state to the radially-expanded state, such as upon being released from a delivery tube; alternatively, for example, it may be balloon-expandable, or may expand along with proximal blood-carrying tubular structure 44.

The purpose of this paragraph is to explain structurally-supported space 62, which is perhaps best shown in FIGS. 2A-B. Structurally-supported space 62 is defined by blood-vessel-fixation structure 60, even though blood-vessel-fixation structure 60 does not define a continuous surface, i.e., structure 60 defines open areas among and between the struts of structural strut members 30 thereof. For some applications, structural strut members 30 of blood-vessel-fixation structure 60 are circumferential (i.e., are disposed around the circumference of blood-vessel-fixation structure 60), and are disposed at respective longitudinal positions along blood-vessel-fixation structure 60, when prosthesis 20 is unconstrained in the radially-expanded state. For these applications, blood-vessel-fixation structure 60 defines open areas longitudinally (i.e., axially) between the circumferential structural strut members. The structural strut members nevertheless collectively define structurally-supported space 62, such as best shown in FIGS. 2A-B.

Distal skirt longitudinal portion 42 comprises a distal skirt tubular structure 70, which typically is self-expanding, i.e., is configured to automatically expand during the transition of prosthesis 20 from the radially-compressed delivery state to the radially-expanded state, such as upon being released from a delivery tube, and which:
  comprises a distal portion 72 of graft member 32 and some of structural strut members 30 (which are optionally circumferential), which are fixed to distal portion 72 of graft member 32, and
  when prosthesis 20 is unconstrained in the radially-expanded state, has smallest and greatest distal-skirt outer cross-sectional areas at respective different smallest and greatest longitudinal locations 74 and 76, and a central longitudinal axis 78.

Typically, the greatest distal-skirt outer cross-sectional area (A) equals at least 150% of the smallest distal-skirt outer cross-sectional area, and (B) equals at least 120% of the average proximal-blood-carrying inner cross-sectional area. The smallest and greatest distal-skirt outer cross-sectional area are measured perpendicular to central longitudinal axis 78, and are defined by an outer surface of distal skirt tubular structure 70. Typically, central longitudinal axes 50 and 78 are coaxial. For some applications, distal skirt tubular structure 70 has a greatest perimeter at greatest longitudinal location 76 that equals at least 120% of an average perimeter of proximal blood-carrying tubular structure 44.

Typically, an average total proximal outer cross-sectional area of proximal branch-enabling longitudinal portion 40, including proximal blood-carrying tubular structure 44 and structurally-supported space 62 along proximal branch-enabling longitudinal portion 40, equals at least 120%, such as at least 140%, e.g., at least 170%, of the average proximal-blood-carrying inner cross-sectional area, when prosthesis 20 is unconstrained in the radially-expanded state. The average total proximal outer cross-sectional area of proximal branch-enabling longitudinal portion 40 is measured perpendicular to central longitudinal axis 50, and is defined by an outer surface of proximal branch-enabling longitudinal portion 40, including proximal blood-carrying tubular structure 44 and structurally-supported space 62 along proximal branch-enabling longitudinal portion 40. For some applications, when prosthesis 20 is unconstrained in the radially-expanded state, proximal branch-enabling longitudinal portion 40 defines, at a plurality of longitudinal locations, a plurality of respective different ratios of (a) a total proximal outer cross-sectional area of proximal branch-enabling longitudinal portion 40, including proximal blood-carrying tubular structure 44 and structurally-supported space 62 along proximal branch-enabling longitudinal portion 40, to (b) a proximal-blood-carrying inner cross-sectional area of proximal blood-carrying tubular structure 44, and a greatest one of the ratios is at least 2.5, such as at least 3, and/or a smallest one of the ratios is less than 1.5, such as less than 1.25.

As used in the present application, including in the claims, the "average graft surface area coverage" of a structure equals the quotient of (a) the surface area of the structure that is covered by graft member 32 divided by (b) the total surface area of the structure. For the purposes of this definition, the surface area of blood-vessel-fixation structure 60 includes the open areas among and between the struts of structural strut members 30 thereof. As used in the present application, including in the claims, a "central longitudinal axis" of an elongate structure is the set of all centroids of transverse cross-sectional sections of the structure along the structure. Thus the cross-sectional sections are locally perpendicular to the central longitudinal axis, which runs along the structure. (If the structure is circular in cross-section, the centroids correspond with the centers of the circular cross-sectional sections.) It is noted that the cross-sectional shape and/or size of a "tubular structure" may vary along the tubular structure.

Typically, a volume of structurally-supported space 62 along distal skirt longitudinal portion 42 equals less than 10% of a volume of distal skirt tubular structure 70, when prosthesis 20 is unconstrained in the radially-expanded state. For some applications (as shown), structurally-supported space 62 is disposed entirely along proximal branch-enabling longitudinal portion 40, such that none of structurally-supported space 62 is disposed along distal skirt longitudinal portion 42, when prosthesis 20 is unconstrained in the radially-expanded state.

Typically, proximal blood-carrying tubular structure 44 is generally cylindrical, when prosthesis 20 is unconstrained in the radially-expanded state, and/or blood-vessel-fixation structure 60 is generally cylindrical, when prosthesis 20 is unconstrained in the radially-expanded state. Typically, contacting portion 64 of blood-vessel-fixation structure 60 directly contacts an external surface of proximal blood-carrying tubular structure 44, when prosthesis 20 is unconstrained in the radially-expanded state. As used in the present application, "generally cylindrical" means that the structure, when unconstrained, could be placed entirely between inner and outer right circular cylinders without touching either of the cylinders, the outer cylinder having a diameter equal to 150% of a diameter of the inner cylinder. It is to be understood that the cylinders are not components of the apparatus, but are instead abstract geometric shapes used to describe a concrete structural property of the structure of the apparatus.

When unconstrained in the radially-expanded state, prosthesis 20 has an average unconstrained perimeter, which may, for example, be at least 40 mm, no more than 90 mm, and/or 40 to 90 mm.

For some applications, the structural strut members 30 of proximal blood-carrying tubular structure 44 are weaker than the structural strut members 30 of blood-vessel-fixation structure 60. This may be the case because the structural strut members 30 of proximal blood-carrying tubular structure 44 need only maintain the patency of proximal blood-carrying tubular structure 44, while the structural strut members 30 of blood-vessel-fixation structure 60 typically apply an outward radial force against blood vessel wall for fixation of the stent-graft in place. For example, an average spring constant of the structural strut members 30 of proximal blood-carrying tubular structure 44 may be no more than 85% (e.g., no more than 70%) of an average spring constant of the structural strut members 30 of blood-vessel-fixation structure 60. (A circumferential portion of proximal blood-carrying tubular structure 44 may share some common structural strut members 30 with blood-vessel-fixation structure 60.)

Typically, structural strut members 30 comprise a metal, such as a flexible metal, an elastic metal, stainless steel (e.g., elastic stainless steel), or a superelastic alloy (such as Nitinol). Graft member 32 comprises one or more biologically-compatible substantially blood-impervious thin flexible sheets, which may be arranged, for example, as a cylinder or other tubular structure. The flexible sheets may comprise, for example, a polymeric material (e.g., a polyester, or polytetrafluoroethylene), a textile material (e.g., polyethylene terephthalate (PET), e.g., Dacron®, manufactured by E. I. du Pont de Nemours and Company, Wilmington, Del., USA), or expanded polytetrafluoroethylene (ePTFE), e.g., manufactured by W. L. Gore & Associates, Newark, Del., USA), natural tissue (e.g., saphenous vein or collagen), or a combination thereof.

For some applications, such as shown in FIGS. 1 and 2A-B, structural strut members 30 comprise a plurality of proximal circumferential structural strut members 82, which, when prosthesis 20 is unconstrained in the radially-expanded state:
define blood-vessel-fixation structure 60, including contacting and non-contacting portions 64 and 66 thereof, and
are disposed entirely surrounding proximal blood-carrying tubular structure 44, such that contacting portion 64 of blood-vessel-fixation structure 60 directly contacts a contact circumferential portion 80 of proximal blood-carrying tubular structure 44.

For some applications, contact circumferential portion 80 of proximal blood-carrying tubular structure 44 has an average arc angle et (alpha), measured about central longitudinal axis 50, of no more than 180 degrees, such as no more than 150 degrees, when prosthesis 20 is unconstrained in the radially-expanded state. For some applications, the average arc angle α (alpha) is at least 140 degrees, such as at least 210 degrees. It is noted that contact circumferential portion 80 extends along the entire proximal branch-enabling longitudinal portion 40, even though proximal circumferential structural strut members 82 define open areas among the struts thereof, and longitudinally (i.e., axially) between the proximal circumferential structural strut members. For some applications, an arc angle of contact circumferential portion 80, measured about central longitudinal axis 50, varies along proximal branch-enabling longitudinal portion 40, such as described hereinbelow with reference to FIGS. 6A-B.

For some applications, proximal blood-carrying tubular structure 44 and blood-vessel-fixation structure 60 comprise some of the same structural strut members 30, when prosthesis 20 is unconstrained in the radially-expanded state. For some applications, proximal blood-carrying tubular structure 44 comprises, in addition to the some of the same structural strut members 30, others of the structural strut members 30, which are securely directly attached to graft member 32 and at least partially define proximal blood-carrying tubular structure 44, when prosthesis 20 is unconstrained in the radially-expanded state. For some applications, proximal circumferential structural strut members 82 at least partially define proximal blood-carrying tubular structure 44, when prosthesis 20 is unconstrained in the radially-expanded state.

Reference is made to FIG. 2B. The configuration shown in FIG. 23 is generally similar to that shown in FIG. 2A, except that proximal circumferential structural strut members 82 are shaped so as to define sharp turns (i.e., local discontinuities) at circumferential interfaces 99 between blood-vessel-fixation structure 60 and proximal blood-carrying tubular structure 44. In this configuration, the average arc angle α (alpha) may be greater than in the configuration shown in FIG. 2A, such as between 200 and 250 degrees.

Figure 3A:
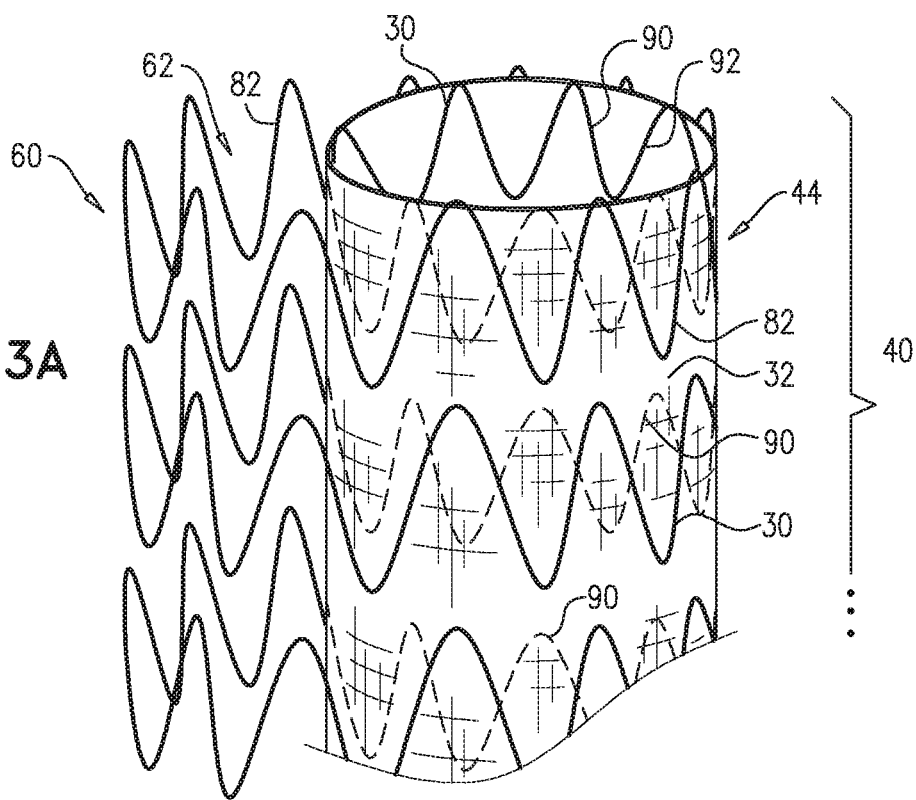
FIGS. 3A-C are schematic illustrations of configurations of a proximal portion of a proximal branch-enabling longitudinal portion of FIGS. 1 and 2A, in accordance with respective applications of the present invention.
Figure 3B:
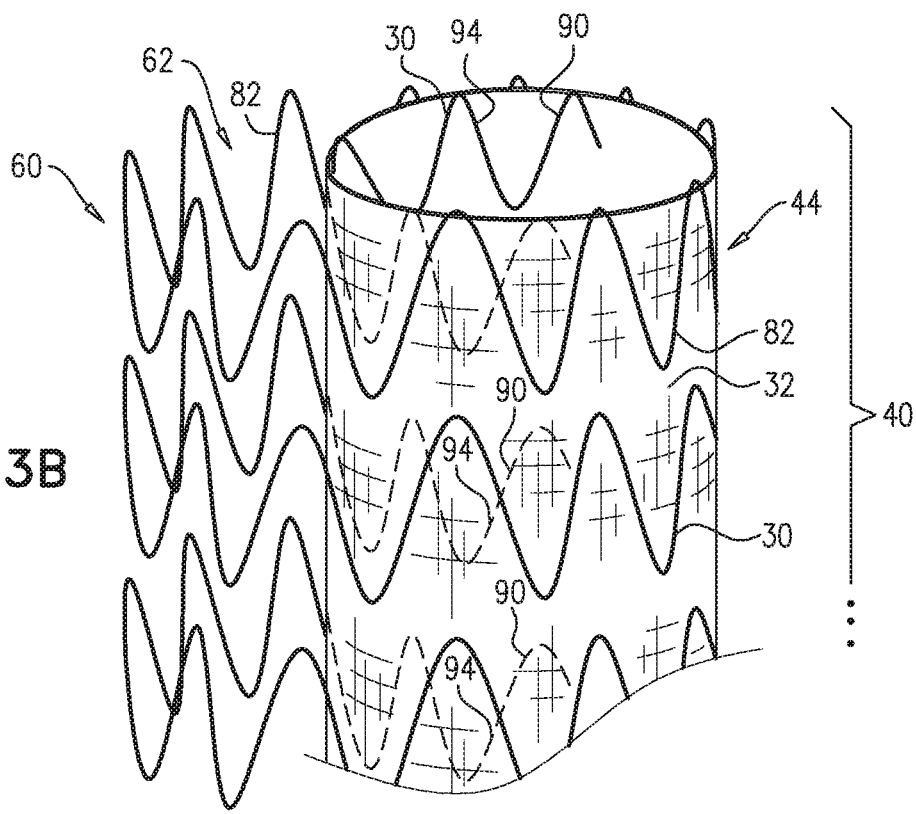
Figure 3C:
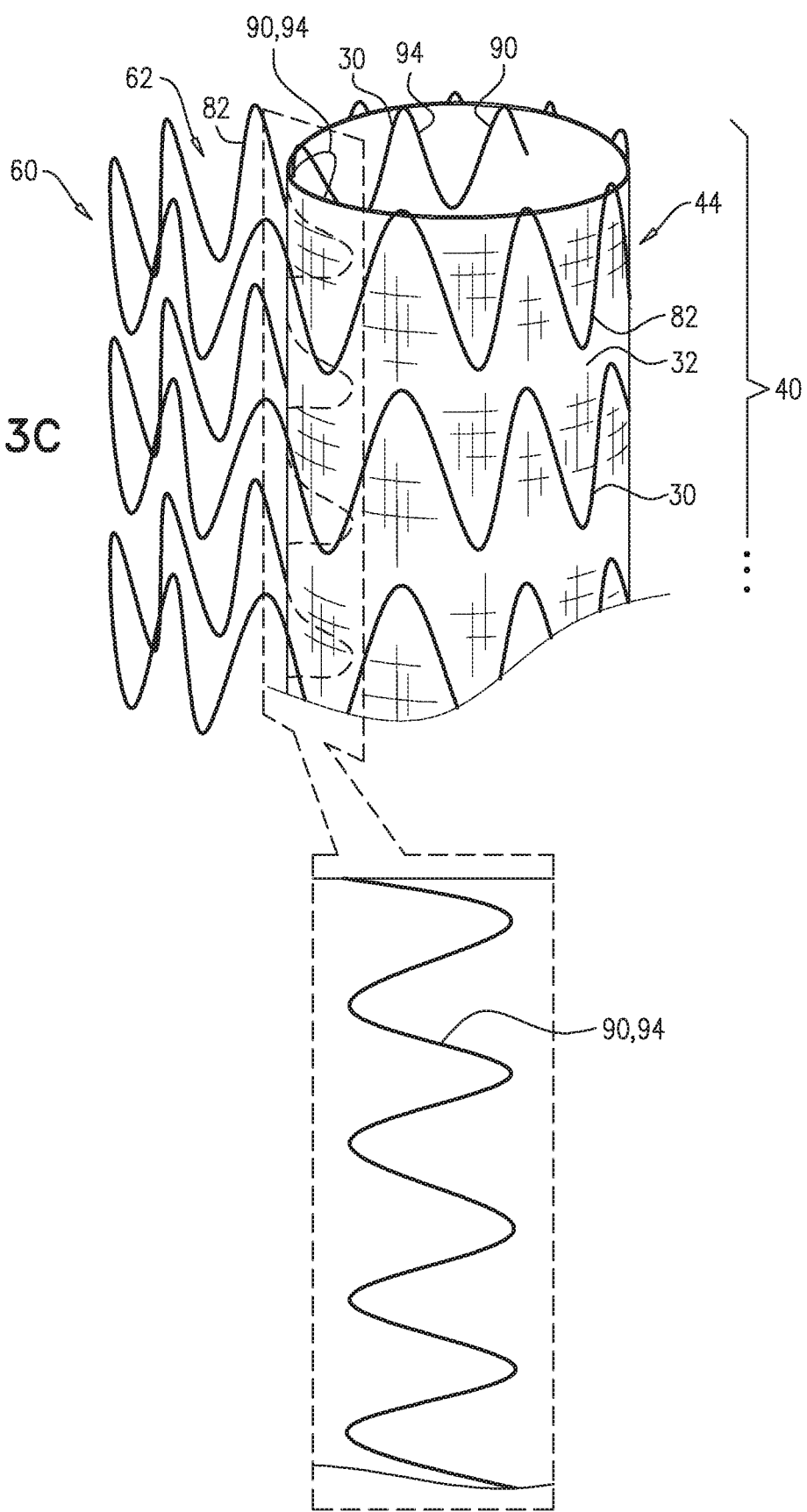

Reference is now made to FIGS. 3A-C, which are schematic illustrations of configurations of a proximal portion of proximal branch-enabling longitudinal portion 40, in accordance with respective applications of the present invention. In these applications, proximal circumferential structural strut members 82 at least partially define proximal blood-carrying tubular structure 44, when prosthesis 20 is unconstrained in the radially-expanded state, as mentioned above. In addition to proximal circumferential structural strut members 82, one or more others 90 of structural strut members 30 are securely directly attached to graft member 32 (on the inside and/or the outside of graft member 32), and at least partially define proximal blood-carrying tubular structure 44, when prosthesis 20 is unconstrained in the radially-expanded state.

For some applications, such as shown in FIG. 3A, the one or more other structural strut members 90 comprise one or more circumferential structural strut members 92, which are disposed at respective longitudinal (i.e., axial) positions along proximal blood-carrying tubular structure 44.

For other applications, such shown in FIG. 3B, the one or more other structural strut members 90 comprise one or more non-circumferential structural strut members 94 (in the sense that they do not completely surround the circumference of blood-carrying tubular structure 44), which are disposed at respective longitudinal positions along proximal blood-carrying tubular structure 44. The one or more non-circumferential structural strut members 94 are disposed at least around a non-contact circumferential portion 96 of proximal blood-carrying tubular structure 44 (labeled in FIGS. 2A-B). Non-contact circumferential portion 96 includes the entire proximal blood-carrying tubular structure circumference other than contact circumferential portion 80 of proximal blood-carrying tubular structure 44.

For still other applications, such as shown in FIG. 3C, the one or more (e.g., exactly one) non-circumferential structural strut members 94 extend longitudinally along proximal blood-carrying tubular structure 44 (on the inside and/or the outside of graft member 32). For example, the one or more (e.g., exactly one) non-circumferential structural strut members 94 may have a zigzag shape or serpentine shape. As mentioned below, the structural strut members 30 of non-contact circumferential portion 96 may be weaker than the structural strut members 30 of contacting portion 64 of blood-vessel-fixation structure 60.

Reference is again made to FIGS. 1 and 2A-B. Blood-vessel-fixation structure 60 has an average unconstrained perimeter when prosthesis 20 is unconstrained in the radially-expanded state; for example, the average unconstrained perimeter may be 70 to 130 mm.

For some applications, the structural strut members 30 of non-contact circumferential portion 96 of proximal blood-carrying tubular structure 44 are weaker than the structural strut members 30 of contacting portion 64 of blood-vessel-fixation structure 60. For example, an average spring constant of the structural strut members 30 of non-contact circumferential portion 96 of proximal blood-carrying tubular structure 44 may be no more than 90% (e.g., no more than 80%) of an average spring constant of the structural strut members 30 of contacting portion 64 of blood-vessel-fixation structure 60.

For some applications, an average graft surface area coverage of non-contact circumferential portion 96 of proximal blood-carrying tubular structure 44 is at least 90% (e.g., at least 95%), when prosthesis 20 is unconstrained in the radially-expanded state.

Reference is again made to FIG. 1, and is additionally made to FIGS. 4A-B, which are schematic illustrations of additional configurations of distal skirt longitudinal portion 42, in accordance with respective applications of the present invention. In the configuration shown in FIG. 1, distal skirt longitudinal portion 42 monotonically widens in a proximal-to-distal direction along an entire length of distal skirt longitudinal portion 42, when prosthesis 20 is unconstrained in the radially-expanded state. In the configurations shown in FIGS. 4A-B, distal skirt longitudinal portion 42 (a) monotonically widens in a proximal-to-distal direction to greatest longitudinal location 76 having the greatest distal-skirt outer cross-sectional area, and (b) narrows in a proximal-to-distal direction from greatest longitudinal location 76, when prosthesis 20 is unconstrained in the radially-expanded state. For some applications, greatest longitudinal location 76 is longitudinally (i.e., axially) located on a distal half H of distal skirt longitudinal portion 42, when prosthesis 20 is unconstrained in the radially-expanded state. For some of these applications, greatest longitudinal location 76 is longitudinally located a distance D from a proximal end 98 of distal skirt longitudinal portion 42, which distance equals between 50% and 85% of a length L of distal skirt longitudinal portion 42, when prosthesis 20 is unconstrained in the radially-expanded state. In the configuration shown in FIG. 4A, graft member 32 is wavy at the distal end of distal skirt longitudinal portion 42, while in the configuration shown in FIG. 4B, graft member 32 extends to the distal end of distal skirt longitudinal portion 42 around the perimeter of the distal end.

Figure 5B:
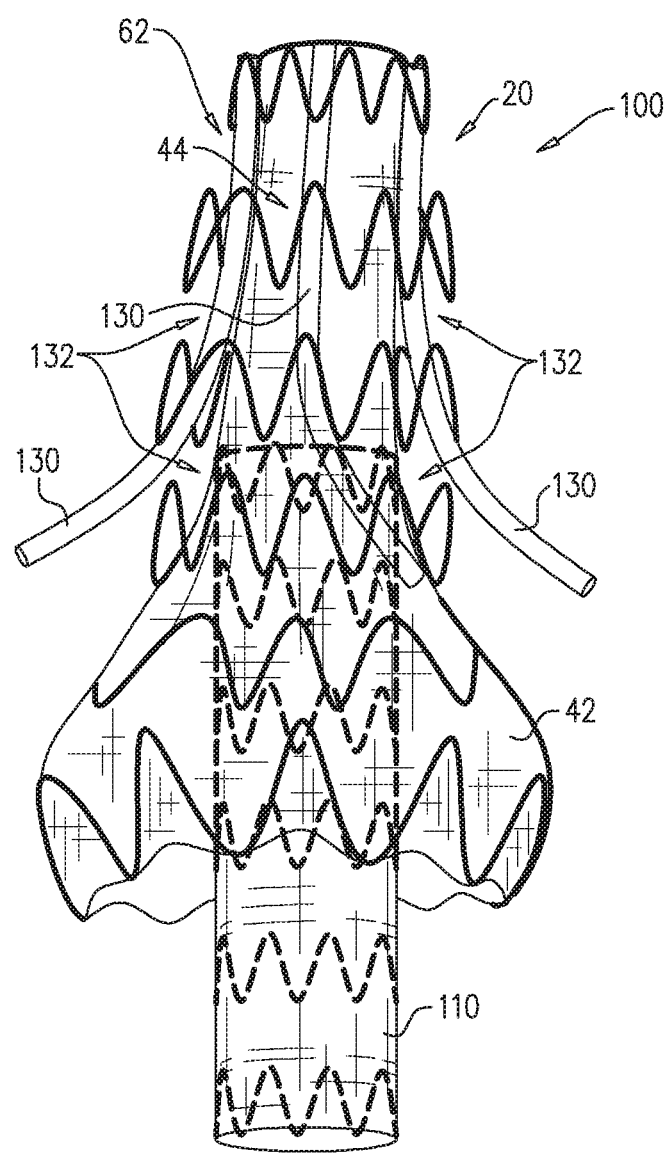
Figure 5C:
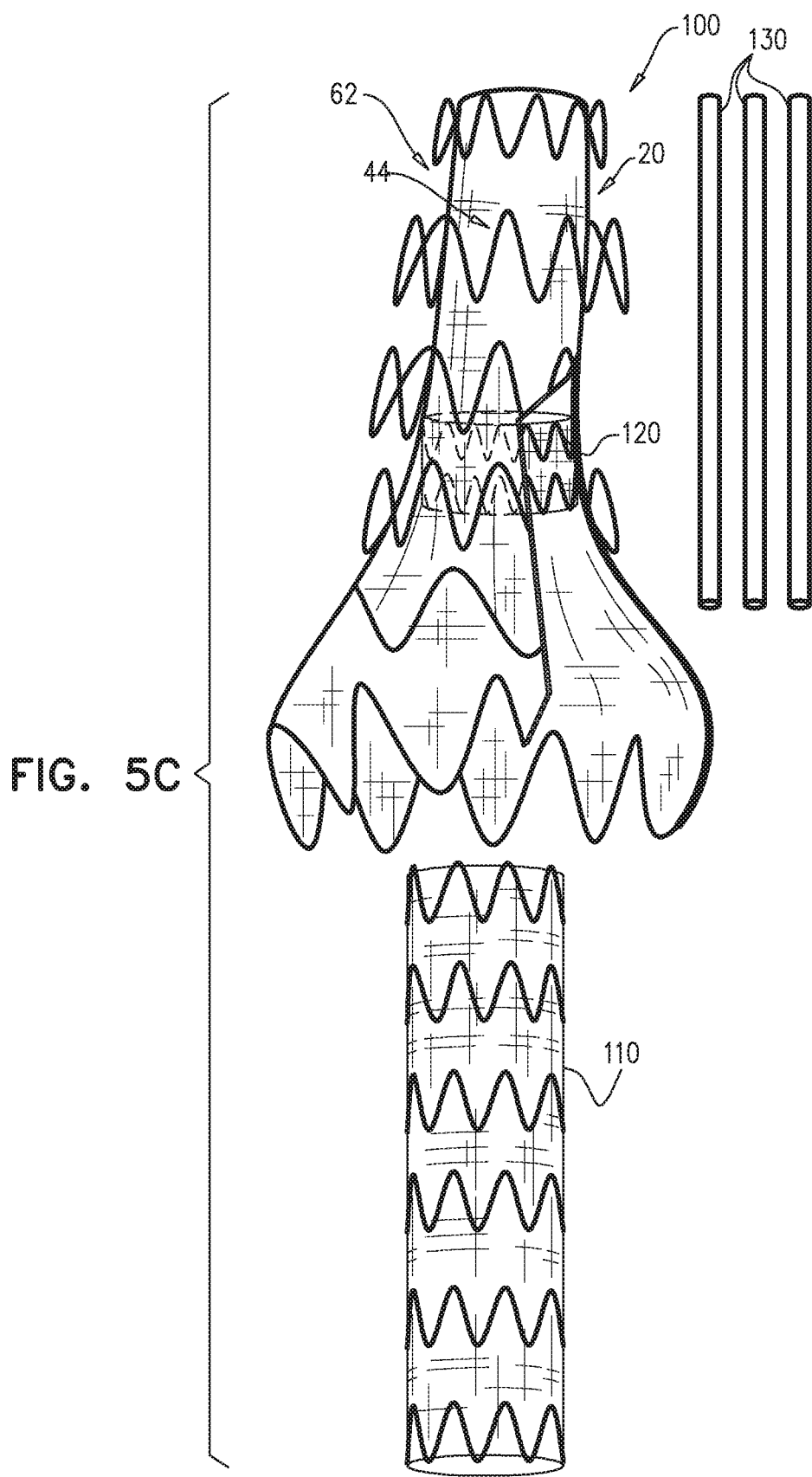

Reference is now made to FIGS. 5A-C, which are schematic illustrations of a multi-component endovascular system 100, in accordance with respective applications of the present invention. Endovascular system 100 comprises endovascular prosthesis 20, described hereinabove with reference to FIGS. 1-4B, which, in these applications, is a main endovascular prosthesis 20. Endovascular system 100 further comprises an extension endovascular prosthesis 110, which is configured to transition from a radially-compressed delivery state to a radially-expanded state. Main and extensions endovascular prostheses 20 are configured to be sealingly coupleable together, typically in situ during an implantation procedure, so as to together define a blood-flow path from proximal blood-carrying tubular structure 44 to extension endovascular prosthesis 110, when main and extension endovascular prostheses 20 and 110 are in their respective radially-expanded states.

Typically, a proximal end of extension endovascular prosthesis 110 is configured to be sealingly coupleable to main endovascular prosthesis 20, such as by outward force applied by extension endovascular prosthesis 110 to an inner surface of proximal blood-carrying tubular structure 44. For some applications, an average inner cross-sectional area of a proximal-most 30 mm of extension endovascular prosthesis 110 equals between 105% and 130% of the average proximal-blood-carrying inner cross-sectional area of proximal blood-carrying tubular structure 44, when main and extension endovascular prostheses 20 and 110 are in their respective radially-expanded states (and not coupled together).

Alternatively or additionally, endovascular system 100 further comprises one or more branching endovascular prostheses 130, such as exactly two or exactly three branching endovascular prostheses 130. Each of branching endovascular prostheses 130 comprises a stent-graft that is configured to transition from a radially-compressed delivery state to a radially-expanded state. Typically, when main and branching endovascular prostheses 20 and 130 are in their respective radially-expanded states, (a) each of branching endovascular prostheses 130 has an average inner cross-sectional area that equals at least 15%, no more than 50%, and/or between 15% and 50% of the average proximal-blood-carrying inner cross-sectional area of proximal blood-carrying tubular structure 44, and/or (b) each of branching endovascular prostheses 130 has an average inner perimeter that equals at least 40%, no more than 70%, and/or between 40% and 70% of an average inner perimeter of proximal blood-carrying tubular structure 44. Branching endovascular prostheses 130 and structurally-supported space 62 along proximal branch-enabling longitudinal portion 40 are sized and shaped to accommodate placement of respective portions of branching endovascular prostheses 130 within structurally-supported space 62 along proximal branch-enabling longitudinal portion 40. The low average graft surface area coverage of non-contacting portion 66 of blood-vessel-fixation structure 60, described hereinabove with reference to FIGS. 1 and 2A, provides lateral openings 132 through which branching endovascular prostheses 130 pass out of structurally-supported space 62 and into branching arteries.

For some applications, main endovascular prosthesis 20 further comprises a prosthesis-engagement member 120, which (a) is tubular, (b) is disposed at least partially within main endovascular prosthesis 20, and (c) is in fluid communication with proximal blood-carrying tubular structure 44, when main endovascular prosthesis 20 is in the radially-expanded state. Prosthesis-engagement member 120 and extension endovascular prosthesis 110 are configured to be sealingly coupled together, such as by outward force applied by extension endovascular prosthesis 110 to an inner surface of prosthesis-engagement member 120, or inward force applied by extension endovascular prosthesis 110 to an outer surface of prosthesis-engagement member 120. For some applications, endovascular system 10 implements techniques described in U.S. Pat. No. 8,870,938, which is incorporated herein by reference, with reference to FIGS. 9A-D thereof, mutatis mutandis.

Reference is now made to FIGS. 6A-B, which are schematic illustrations of two stages of an exemplary transvascular delivery procedure for deploying endovascular system 100 in an aneurysmal descending aorta 150, in accordance with an application of the present invention. FIGS. 6A-B schematically show a portion of a typical aorta 150, as well as left and right renal arteries 152A and 152B, left and right iliac arteries 154A and 154B, and a superior mesenteric artery (SMA) 156 (which is on the anterior surface of the aorta). Endovascular system 100 may be used to treat a blood vessel, such as an artery, e.g., descending aorta 150, suffering from an aneurysm, a dissection, or, more generally, a pathologically dilated blood vessel. Although FIGS. 6A-B illustrate the deployment using the particular configuration of distal skirt longitudinal portion 42 shown in FIG. 4B, the configurations shown in FIG. 1 or 4A, or other configurations, may be similarly used.

FIG. 6A shows main endovascular prosthesis 20 upon deployment thereof in descending aorta 150, spanning left and right renal arteries 152A and 152B. Techniques for deployment may be used that are described in one or more of the patent applications incorporated hereinbelow by reference, or otherwise known in the art. Although the deployment is illustrated with reference to the descending aorta, renal arteries, and SMA, endovascular system 100 may also be deployed in the vicinity of other main and branching blood vessels, such as arteries, e.g., visceral arteries. For some applications, a smallest one of the one or more branching arteries has a proximal diameter that is no more than 30% (e.g., no more than 20%) of a diameter of the main artery at a branching location.

Blood-vessel-fixation structure 60 creates structurally-supported space 62 alongside proximal blood-carrying tubular structure 44, between proximal blood-carrying tubular structure 44 and a circumferential portion of a wall of aorta 150, upstream of and alongside renal arteries 152A and 152B, and, optionally, downstream of renal arteries 152A and 152B (such that blood-vessel-fixation structure 60 longitudinally spans the renal arteries). Distal skirt longitudinal portion 42 presses against the aortic wall downstream of the renal arteries, thereby limiting blood flow into a subrenal aneurysmal sac 158. Distal skirt longitudinal portion 42 thus isolates aneurysmal sac 158 from the "gutter" created by blood-vessel-fixation structure 60 in structurally-supported space 62. Typically, proximal blood-carrying tubular structure 44 is positioned entirely within aorta 150.

FIG. 6B shows endovascular system 100 upon the additional deployment of three branching endovascular prostheses 130. The three branching endovascular prostheses 130 are positioned extending along a portion of main endovascular prosthesis 20 and into respective branching arteries: left renal artery 152A, right renal artery 152B, and SMA 156. These branching prostheses thus provide a blood-flow path from the main artery to the branching arteries. Structurally-supported space 62 creates a non-compressible path for deployment of branching endovascular prostheses 130 around proximal blood-carrying tubular structure 44. The low average graft surface area coverage of non-contacting portion 66 of blood-vessel-fixation structure 60, described hereinabove with reference to FIGS. 1 and 2A-B, provides lateral openings 132 through which branching endovascular prostheses 130 can be readily advanced out of structurally-supported space 62 for cannulation of the renal arteries and SMA. As a result, endovascular system 100 accommodates common anatomic variations in the axial and circumferential locations of the branching arteries, without the need to customize main endovascular prosthesis 20 for each patient.

Typically, respective proximal ends of branching endovascular prostheses 130 are disposed at or near a proximal end of main endovascular prosthesis 20, such as within 2 cm of the proximal end of main endovascular prosthesis 20 (either proximal or distal the proximal end). Preferably, the respective proximal ends of branching endovascular prosthesis 130 are disposed not proximally to the proximal end of main endovascular prosthesis 20, because if they were disposed proximally to the proximal end of main endovascular prosthesis 20, blood flow might cause them to bend, curve, and whip in accordance with the aortic systole cycle.

For some applications, endovascular system 100 does not comprise branching endovascular prostheses 130. Blood flow to the branching blood vessels is instead directly provided by structurally-supported space 62 along proximal branch-enabling longitudinal portion 40. For these application, the complete deployment of main endovascular prosthesis 20 is shown in FIG. 6A (extension endovascular prosthesis 110 is also deployed subsequently).

FIG. 6B also shows endovascular system 100 upon the additional deployment of extension endovascular prosthesis 110, and, optionally, one or more additional extension prostheses, which collectively bypass aneurysmal sac 158 to left and right iliac arteries 154A and 154B. As described hereinabove with reference to FIGS. 5A-C, extension endovascular prosthesis 110 is sealingly coupled to main endovascular prosthesis 20 during the deployment procedure. As can be seen in FIG. 6B, upon deployment of all of the endoluminal prostheses, multi-component endovascular system 100 defines a blood-flow path from upstream of the renal arteries to the renal arteries, SMA, and iliac arteries.

Reference is still made to FIGS. 6A-B. For some applications, such as shown in Section A-A of FIGS. 6A-B, contact circumferential portion 80 of proximal blood-carrying tubular structure 44 is entirely circumferentially contiguous along at least a longitudinal portion of proximal blood-carrying tubular structure 44, when prosthesis 20 is unconstrained in the radially-expanded state. In other words, at any given longitudinal position within the at least a longitudinal portion of proximal blood-carrying tubular structure 44, contact circumferential portion 80 circumferentially spans exactly one continuous range of angles about central longitudinal axis 50. For example, in Section A-A, proximal blood-carrying tubular structure 44 is entirely circumferentially contiguous because contacting portion 64 of blood-vessel-fixation structure 60 contacts proximal blood-carrying tubular structure 44 only, and circumferentially continuously, between about half past ten o'clock and half past one o'clock. (It is noted that although FIGS. 6A-B show prosthesis 20 somewhat radially constrained by the wall of aorta 150, these figures still illustrate many of the features of prosthesis 20 when it is unconstrained in the radially-expanded state.)

Alternatively or additionally, for some applications, as shown in Section B-B of FIGS. 6A-B, contact circumferential portion 80 of proximal blood-carrying tubular structure 44 is circumferentially non-contiguous along at least a longitudinal portion of proximal blood-carrying tubular structure 44, when prosthesis 20 is unconstrained in the radially-expanded state. In other words, at any given longitudinal position within the at least a longitudinal portion of proximal blood-carrying tubular structure 44, contact circumferential portion 80 circumferentially spans at least two continuous, but non-contiguous, ranges of angles about central longitudinal axis 50. For example, in Section B-B, proximal blood-carrying tubular structure 44 is circumferentially non-contiguous because contacting portion 64 comprises two contacting sub-portions (first and second contacting sub-portions 64A and 64B). These two contacting sub-portions are circumferentially non-contiguous with one another. Each of these two contacting sub-portions is circumferentially contiguous within itself. First contacting sub-portion 64A contacts proximal blood-carrying tubular structure 44 at a first contact circumferential sub-portion 80A between about half past ten o'clock and half past one o'clock, and (b) second contacting sub-portion 64B contacts proximal blood-carrying tubular structure 44 at a second contact circumferential sub-portion 80B between about five o'clock and seven o'clock.

For some applications, an average arc angle β (beta) of first contact circumferential sub-portion 80A, measured about central longitudinal axis 50, is at least 40 degrees (e.g., at least 70 degrees), no more than 180 degrees (e.g., no more than 150 degrees), and/or between 40 and 180 degrees, such as between 70 and 150 degrees, and/or an average arc angle γ (gamma) of second contact circumferential sub-portion 80B, measured about central longitudinal axis 50, is at least 40 degrees (e.g., at least 60 degrees), no more than 170 degrees (e.g., no more than 140 degrees), and/or between 40 and 170 degrees, such as between 60 and 140 degrees. Typically, first and second contact circumferential sub-portions 80A and 80B are generally circumferentially opposite one another, i.e., respective circumferential centers of the sub-portions are disposed between 160 and 180 degrees from each other.

For some applications, as shown in FIGS. 6A-B, an arc angle of contact circumferential portion 80 of proximal blood-carrying tubular structure 44 (i.e., the sum of all sub-portions thereof), measured about central longitudinal axis 50, is greater at distal end 54 of proximal blood-carrying tubular structure 44 than at proximal end 52 of proximal blood-carrying tubular structure 44, when prosthesis 20 is unconstrained in the radially-expanded state. For some of these applications, the arc angle monotonically non-decreases from proximal end 52 to distal end 54 of proximal blood-carrying tubular structure 44 (and is optionally greater at distal end 54 than at proximal end 52), when prosthesis 20 is unconstrained in the radially-expanded state.

For some of these applications, contact circumferential portion 80 is circumferentially non-contiguous at at least distal end 54 of proximal blood-carrying tubular structure 44, when prosthesis 20 is unconstrained in the radially-expanded state. In addition, in these applications, contact circumferential portion 80 is typically entirely circumferentially contiguous at at least proximal end 52 of proximal blood-carrying tubular structure 44, when prosthesis 20 is unconstrained in the radially-expanded state. In the present application, including the claims, at any longitudinal site of proximal blood-carrying tubular structure 44 at which contact circumferential portion 80 is circumferentially non-contiguous, the arc angle of contact circumferential portion 80 at the site equals the sum of all of the contact circumferential sub-portions of contact circumferential portion 80. For example, at the longitudinal site of Section B-B, the arc angle of contact circumferential portion 80 equals the sum of angles β (beta) and γ (gamma).

For others of these applications, contact circumferential portion 80 is entirely circumferentially contiguous at both proximal and distal ends 52 and 54 of proximal blood-carrying tubular structure 44, when prosthesis 20 is unconstrained in the radially-expanded state.

Reference is now made to FIGS. 7A-17, which are schematic illustrations of several configurations of an endovascular prosthesis 200, in accordance with respective applications of the present invention. Endovascular prosthesis 200 may be provided as part of an endovascular system 260, which may additionally comprise other components, such as an endovascular delivery tool 770 (e.g., comprising a delivery sheath 772), such as described hereinbelow with reference to FIG. 14A, and/or additional endovascular stent-grafts, such as described regarding endovascular prosthesis 20 hereinabove with reference to FIGS. 5A-C and/or 6A-B, mutatis mutandis, and/or hereinbelow with reference to FIGS. 14A-C, 15, 16, and/or 17.

Figure 14A:
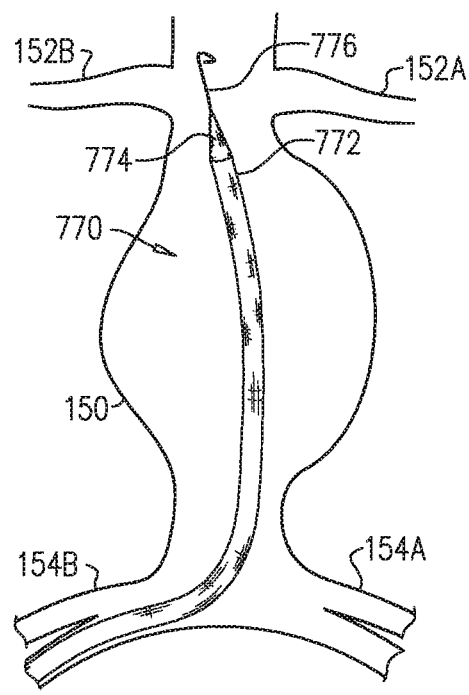
FIGS. 14A-C are schematic illustrations of three stages of an exemplary transvascular delivery procedure for deploying the endovascular prosthesis of FIGS. 7A-B in an aneurysmal descending aorta, in accordance with an application of the present invention.

Endovascular prosthesis 200 (a) is removably disposed in the delivery sheath in a radially-compressed delivery state, such as shown in FIG. 14A, and (b) is configured to assume a radially-expanded state when unconstrained, such as shown in FIGS. 7A-B, 8, 9A-B. 10A-B, 11A-C, 12A-B, 14B-C, 15, 16, and 17. For some applications, endovascular prosthesis 200 is self-expanding, i.e., is configured to automatically transition from the radially-compressed delivery state to the radially-expanded state upon being released from the delivery sheath. For other applications, prosthesis 200 is plastically expandable, such as balloon-expandable.

For some applications, endovascular prosthesis 200 comprises:
  a stent-graft 240, which comprises structural strut members 230 and a graft member 232; structural strut members 230 and graft member 232 are attached to each other and, when endovascular prosthesis 200 is unconstrained in the radially-expanded state, together are shaped so as to define a blood-carrying tubular structure 244 defining a lumen; and
  an external coagulation inducer 250, which (a) is fixed to an external surface 252 of stent-graft 240 both when stent-graft 240 is and is not removably disposed in the delivery sheath, and (b) comprises a solid material, such as polyethylene, polyurethane, ePTFE, silicone, polystyrene, polypropylene, nitinol and other polymers and/or implantable-graft flexible metals, or metallic alloys.

As used in the present application, including in the claims, "solid" refers to one of the fundamental states of matter, and does not include liquid, gas, plasma, or gel. That the material of external coagulation inducer 250 is "solid" does not imply that the material has any particular rigidity, stiffness, or other mechanical properties, or that the material is not porous. Although external coagulation inducer 250 comprises a solid material, external coagulation inducer 250 may optionally comprise one or more non-solid materials in addition to the solid material.

Typically, blood-carrying tubular structure 244 is generally cylindrical, when prosthesis 200 is unconstrained in the radially-expanded state. Typically, structural strut members 230 comprise a metal, such as a flexible metal, an elastic metal, stainless steel (e.g., elastic stainless steel), cobalt-chromium, or a superelastic alloy (such as Nitinol). Graft member 232 comprises one or more biologically-compatible substantially blood-impervious thin flexible sheets, which may be arranged, for example, as a cylinder or other tubular structure. The flexible sheets may comprise, for example, a polymeric material (e.g., a polyester, or polytetrafluoroethylene (PTFE)), a textile material (e.g., polyethylene terephthalate (PET), e.g., Dacron®, manufactured by E. I. du Pont de Nemours and Company, Wilmington, Del., USA), or expanded polytetrafluoroethylene (ePTFE), e.g., manufactured by W. L. Gore & Associates, Newark, Del., USA), natural tissue (e.g., saphenous vein or collagen), or a combination thereof.

Figure 8:
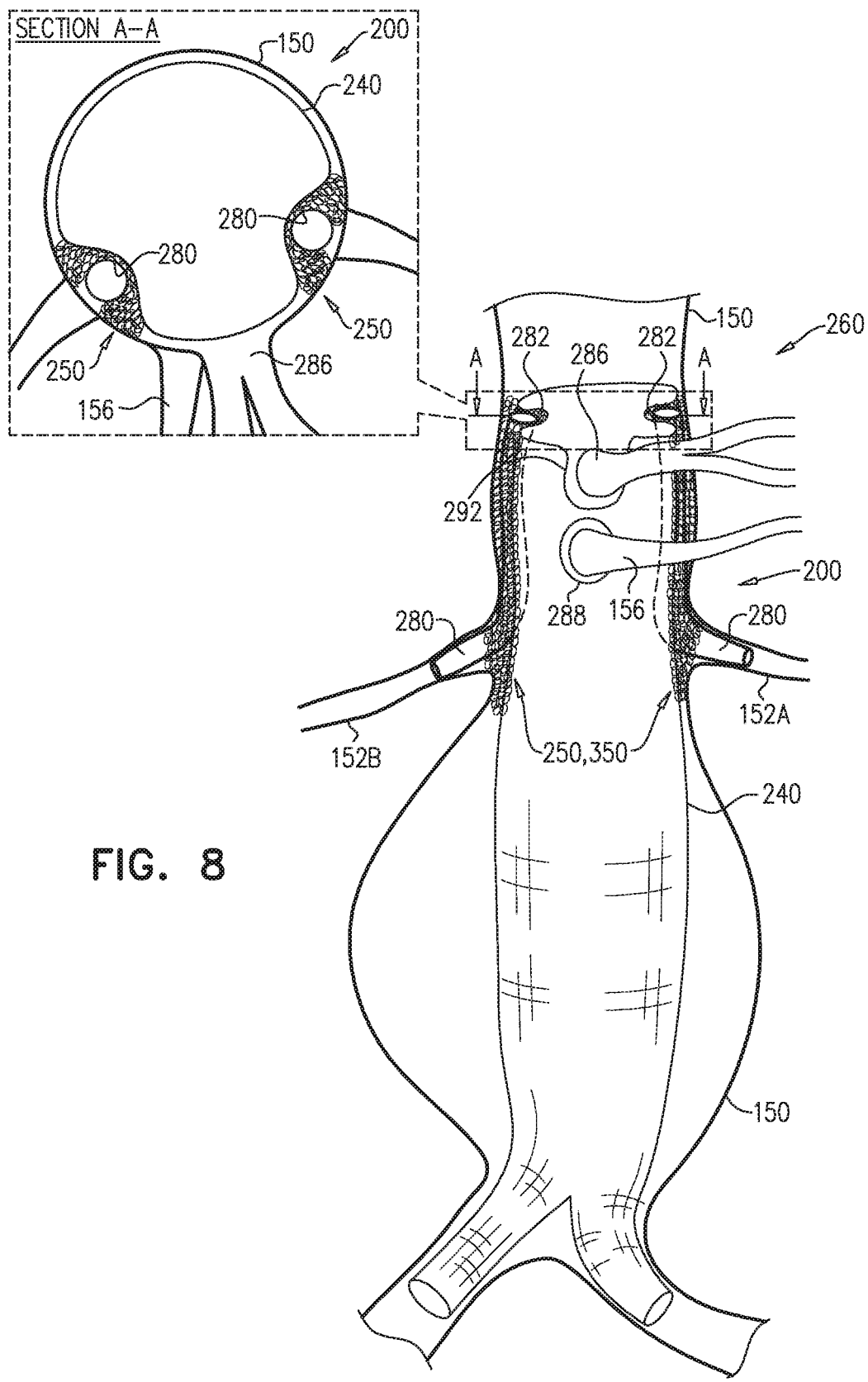
FIG. 8 is a schematic illustration of the endovascular prosthesis of FIGS. 7A-B deployed in a descending aorta and branching arteries, in accordance with an application of the present invention.

Reference is now made to FIG. 8, which is a schematic illustration of endovascular system 260 deployed in descending aorta 150 and branching arteries, in accordance with an application of the present invention. In this particular configuration, endovascular system 260 comprises endovascular prosthesis 200 and two branching stent-grafts 280. External coagulation inducer 250 is configured to impede blood flow external to the lumen of blood-carrying tubular structure 244 when a longitudinal portion of endovascular prosthesis 200 is placed side-by-side (i.e., in parallel with) with one or more branching stent-grafts 280. External coagulation inducer 250 reduces the likelihood of long-term leakage (i.e., blood flow) through "gutters" 282, which are the residual intravascular space disposed outside the lumens of stent-graft 240 and branching stent-graft(s) 280. As a result, the likelihood of type 1 endoleak is reduced. Although in FIG. 8 stent-graft 240 is shown deployed in descending aorta 150 and branching stent-grafts 280 are shown deployed in left and right renal arteries 152A and 152B, stent-graft 240 may also be deployed in other arteries, such the ascending aorta or the aortic arch, and branching stent-grafts 280 may also be deployed in other arteries, such as superior mesenteric artery (SMA) 156, a celiac artery 286, a subclavian artery, and/or a common carotid artery.

For some applications, external coagulation inducer 250 comprises a plurality of non-contiguous external coagulation regions 290, which together define external coagulation inducer 250. For example, external coagulation regions 290 may be disposed and configured to impede blood flow in respective chimneys of respective branching arteries.

For some applications, when endovascular prosthesis 200 is unconstrained in the radially-expanded state, external coagulation inducer 250 has a greatest radial dimension, measured radially outward from external surface 252 of stent-graft 240, the greatest radial dimension at least 2 mm, such as at least 3 mm, e.g., at least 5 mm.

For some applications, stent-graft 240 is shaped so as to define at least one fenestration 288 through graft member 232. For some applications, a perimeter of fenestration 288 equals between 20% and 40% of a perimeter of stent-graft 240 at an axial location of fenestration 288. For some applications, fenestration 288 is substantially circular, such as circular. For some applications, endovascular system 260 further comprises a branching stent-graft that is configured to be externally connected to fenestration 288, creating a blood flow channel between a lumen of the branching stent-graft and the lumen of stent-graft 240. For some applications, fenestration 288 is circumferentially reinforced with a metallic structural member having substantially the same shape as the perimeter of the fenestration. For some applications, a radiopaque marker is circumferentially disposed along fenestration 288. For some applications, fenestration 288 is disposed proximally (i.e., upstream) to external coagulation inducer 250. For some applications, a pre-cannulated guidewire is disposed inside the lumen of stent-graft 240 and exits the lumen via fenestration 288, when endovascular prosthesis 200 is in the radially-compressed delivery state. For some applications, fenestration 288 is disposed proximally to external coagulation inducer 250.

For some applications, graft member 232 of stent-graft 240 is shaped so as to define at least one scallop 292 (shown in FIG. 8). Typically, a circumference of scallop 292 is between 25 and 50 ram. For some applications, scallop 292 is U-shaped, V-shaped, or rectangular. For some applications, scallop 292 is disposed proximally (i.e., upstream) to fenestration 288. For some applications, an axial midpoint of scallop 292 is disposed between 1 and 3 centimeters proximally to an axial midpoint of fenestration 288. Alternatively or additionally, for some applications, scallop 292 is disposed proximally to external coagulation inducer 250.

Figure 7A:
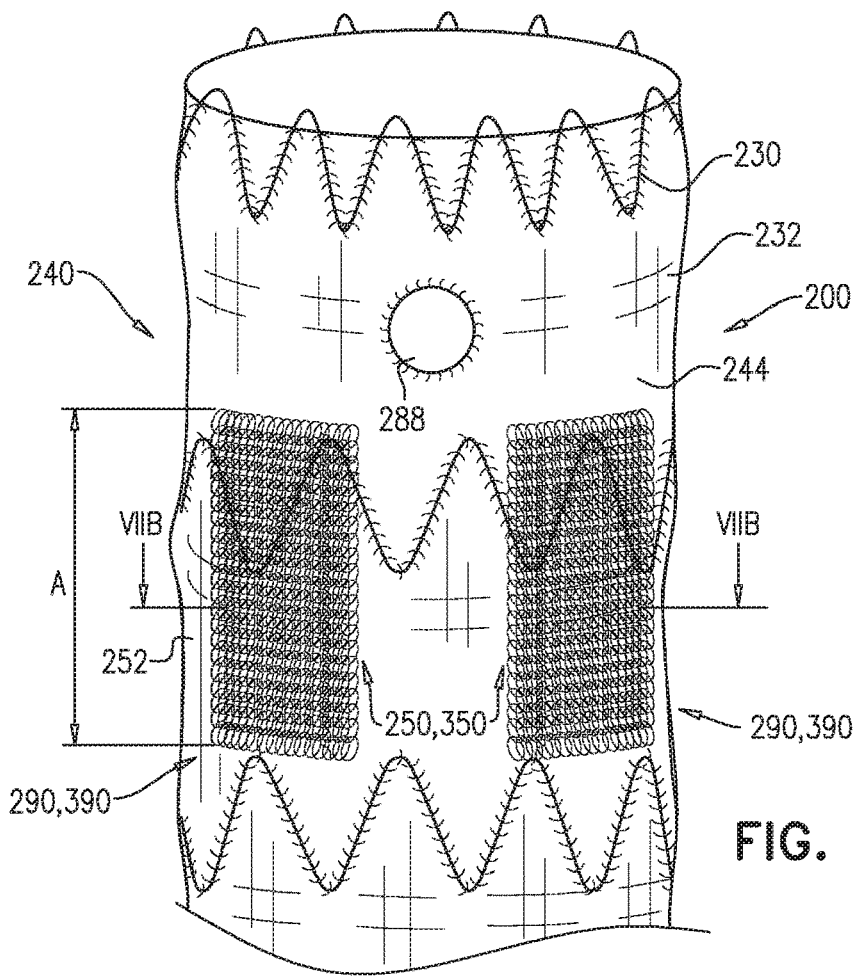
FIGS. 7A-B are schematic illustrations of an endovascular prosthesis, in accordance with an application of the present invention.
Figure 7B:
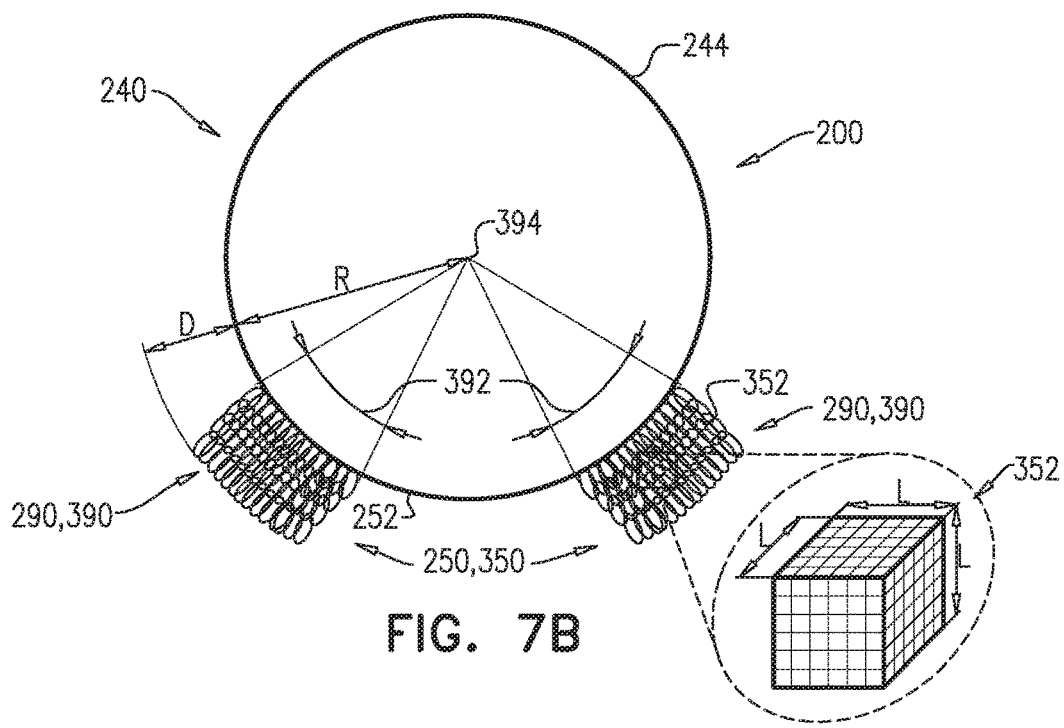

Reference is made to FIGS. 7A-8. FIG. 7B is a cross-sectional view of endovascular prosthesis 200 taken along line VIIB-VIIB of FIG. 7A. In this configuration, external coagulation inducer 250 comprises an external coagulation inducer 350, the material of which may be considered "fluffy," e.g., similar to steel wool. When endovascular prosthesis 200 is unconstrained in the radially-expanded state, (a) external coagulation inducer 350 is shaped so as to encompass at least a cube 352 having an edge length L of 3 mm and entirely filled with 216 sub-cubes, each of which has an edge length of 0.5 mm, and (b) at least 50% e.g., at least 70% or at least 85%, such as 100%) of the sub-cubes contain some of the solid material of external coagulation inducer 350. FIG. 7B shows the edge length L of 3 mm, which is entirely filled with 216 sub-cubes (6×6×6). Typically, at least 10% (e.g., at least 20%, at least 50%, or at least 80%) of the volume of cube 352 is void of solid matter (on a macroscopic or microscopic level, without taking into account inter- or intra-atomic space). Alternatively or additionally, for some applications, at least 50% (e.g., at least 70%, such as at least 85%) of the sub-cubes contain at least one external surface (i.e., macroscopic external surface) of the solid material of external coagulation inducer 350, when endovascular prosthesis 200 is unconstrained in the radially-expanded state.

As used in the present application, including in the claims, a "cube" and a "sub-cube" is a three-dimensional solid object bounded by six equal square sides. It is to be understood that the cubes and sub-cubes are not components of the apparatus, but are instead abstract geometric shapes used to describe a concrete structural property of the structure of the apparatus.

For some applications, when endovascular prosthesis 200 is unconstrained in the radially-expanded state, (a) external coagulation inducer 350 is shaped so as to encompass at least a cube having an edge length of 4 mm and entirely filled with 512 sub-cubes, each of which has an edge length of 0.5 mm, and (b) at least 50% (e.g., at least 70%, such as at least 85%) of the sub-cubes contain some of the solid material of external coagulation inducer 350. For some applications, when endovascular prosthesis 200 is unconstrained in the radially-expanded state, (a) external coagulation inducer 350 is shaped so as to encompass at least a cube having an edge length of 5 mm and entirely filled with 1000 sub-cubes, each of which has an edge length of 0.5 mm, and (b) at least 50% (e.g., at least 70%, such as at least 85%) of the sub-cUbes contain some of the solid material of external coagulation inducer 350.

For some applications, the solid material is shaped as one or more elongate members, e.g., comprising a metal or a polymer. For some applications, an average diameter of the one or more elongate members is between 0.05 and 0.2 microns. For some applications, each of the elongate members comprises a wire, i.e., a single extruded fiber. For other applications, each of the elongate members comprises yarn, which comprises interlocked fibers.

For some applications, such as shown in FIGS. 7A-8, external coagulation inducer 350 comprises a plurality of non-contiguous external coagulation regions 390, e.g., two non-contiguous external coagulation regions 390 that are configured to impede blood flow at the renal arteries' respective gutters. For some applications, respective radiopaque markers are provided that indicate the respective borders of non-contiguous external coagulation regions 390.

For some applications, when endovascular prosthesis 200 is unconstrained in the radially-expanded state, external coagulation inducer 350 extends along an axial length A of stent-graft 240 equal to at least 1 cm, such as at least 2 cm. For some applications, endovascular prosthesis 200 is unconstrained in the radially-expanded state, external coagulation inducer 350 (including the plurality of non-contiguous external coagulation regions 390, if provided) circumscribes one or more circumferential arcs 392 having an aggregate angle measured about a central longitudinal axis 394 of stent-graft 240, the aggregate angle at least 25 degrees, such as at least 50 degrees, e.g., at least 90 degrees, such as at least 180 degrees, e.g., at least 300 degrees. Alternatively or additionally, for some applications, the aggregate angle is no more than 90 degrees, such as no more than 40 degrees. For some applications, the one or more circumferential arcs 392 include two or more non-contiguous circumferential arcs 392, such as shown in FIG. 7B; for some of these applications, a circumferential gap between the two or more non-contiguous circumferential arcs 392 is between 40 and 100 degrees.

For some applications, when endovascular prosthesis 200 is unconstrained in the radially-expanded state, external coagulation inducer 350 has a greatest radial dimension D, measured radially outward from external surface 252 of stent-graft 240, the greatest radial dimension D at least 20% (e.g., at least 40%) of a radius R of stent-graft 240 at an axial location, along stent-graft 240, of the greatest radial dimension D. Alternatively or additionally, for some applications, when endovascular prosthesis 200 is unconstrained in the radially-expanded state, external coagulation inducer 350 has a greatest radial dimension D, measured radially outward from external surface 252 of stent-graft 240, the greatest radial dimension D at least 5 mm, such as at least 7.5 mm, e.g., at least 10 mm, and/or no more than 15 mm.

For some applications, when endovascular prosthesis 200 is unconstrained in the radially-expanded state, stent-graft 240, at all axial locations therealong farther than respective distances from axial ends of stent-graft 240, includes at least one circumferentially-contiguous circumferential arc free of all material more than 1 mm radially outward from an external surface of graft member 232. Each of the respective distances is 5 mm (e.g., at least 10 mm), and the circumferentially-contiguous circumferential arc has an angle measured about central longitudinal axis 394 of stent-graft 240, the angle equal to at least 90 degrees (e.g., at least 180 degrees). (In configurations in which an end of the stent-graft is bifurcated, the end has two axial ends.)

For some applications, when endovascular prosthesis 200 is unconstrained in the radially-expanded state, external coagulation inducer 350 is located farther than respective distances from axial ends of stent-graft 240, each of the respective distance at least 5 mm (e.g., at least 10 mm). (In configurations in which an end of the stent-graft is bifurcated, the end has two axial ends.)

Figure 9A:
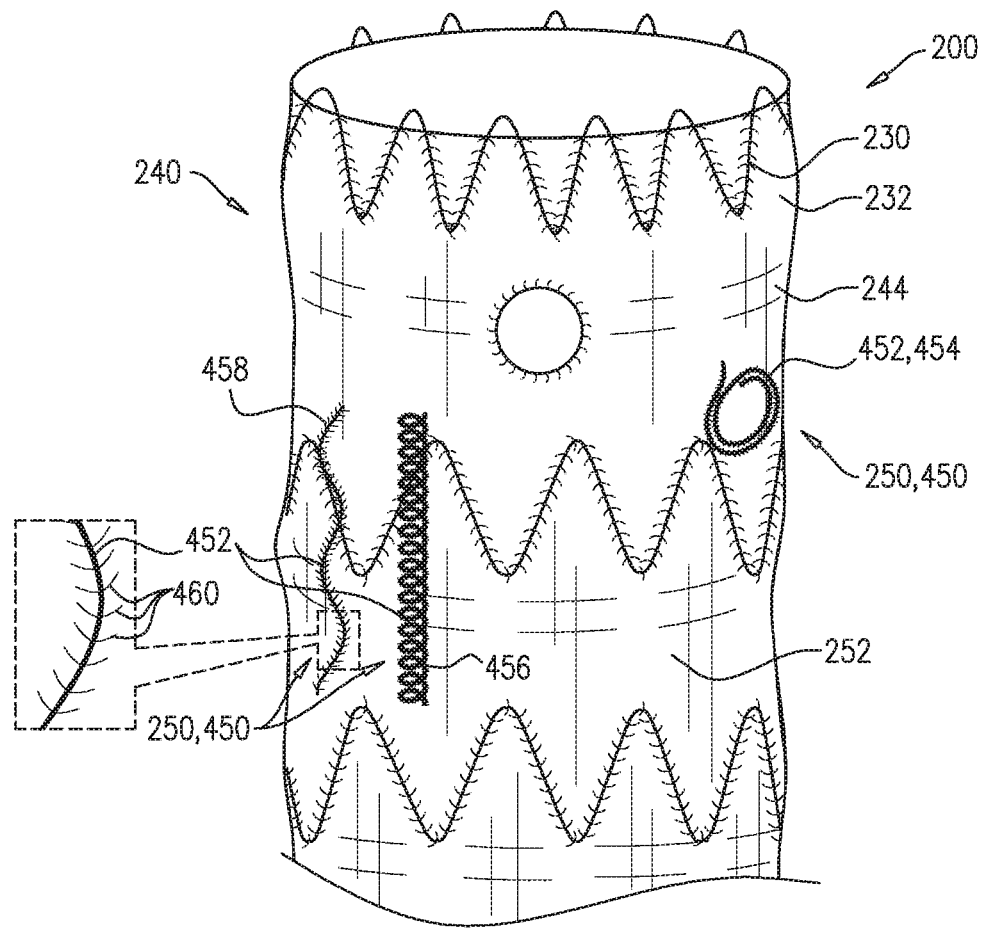
FIGS. 9A-B are schematic illustrations of another configuration of the endovascular prosthesis of FIGS. 7A-B, in accordance with an application of the present invention.
Figure 9B:
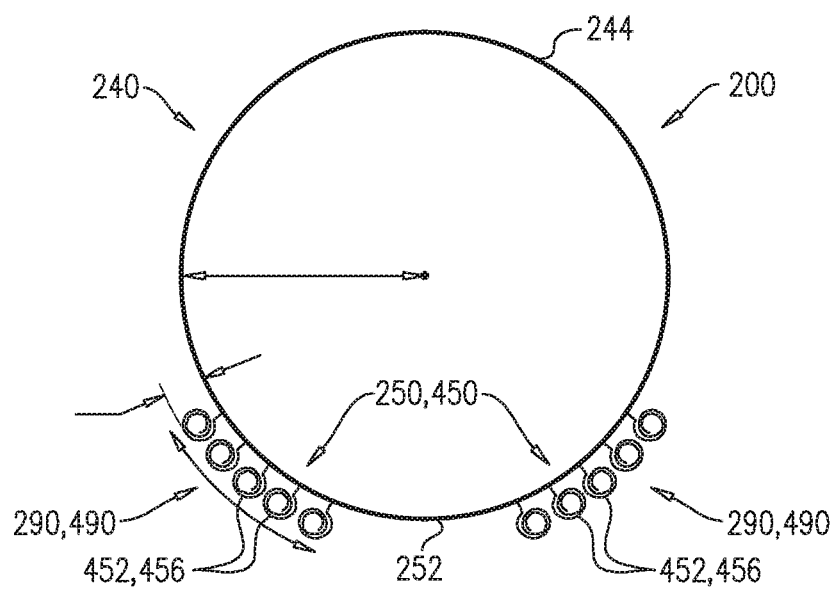

Reference is now made to FIGS. 9A-B, which are schematic illustrations of another configuration of endovascular prosthesis 200, in accordance with an application of the present invention. FIG. 9B is a cross-sectional view of a configuration of endovascular prosthesis 200. In this configuration, external coagulation inducer 250 comprises an external coagulation inducer 450, which comprises a plurality of elongate coagulation members 452, each of which (a) is fixed, at at least one point along elongate coagulation member 452, to external surface 252 of stent-graft 240 both when stent-graft 240 is and is not removably disposed in the delivery sheath, and (b) has a length of between 1 and 15 cm when endovascular prosthesis 200 is unconstrained in the radially-expanded state. For some applications, external coagulation inducer 450 comprises (a) two elongate coagulation members 452 (one for each of the renal arteries), or (b) three elongate coagulation members 452 (one for each of the renal arteries and one for the SMA, in order to prevent leakage from fenestration 288). For some applications, elongate coagulation members 452 comprise a metal or a polymer. For some applications, each of elongate coagulation members 452 comprises one or more elongated members, which may, for example, have a diameter of between 0.1 and 0.5 mm. For some applications, each of the elongate members comprises a wire, i.e., a single extruded strand, or a fiber. For other applications, each of the elongate members comprises yarn, which comprises interlocked fibers.

FIG. 9A shows three different types of elongate coagulation members 452. In practice, endovascular prosthesis 200 may comprise a combination of different types of elongate coagulation members 452, such as shown in FIG. 9A, or a single type of elongate coagulation members 452, such as shown in FIG. 9B. For some applications, elongate coagulation members 452 are configured to self-curl to preset shapes when endovascular prosthesis 200 is unconstrained in the radially-expanded state; for example, the preset shapes may be substantially circular (as labeled with reference numeral 454), substantially helical (as labeled with reference numeral 456 in FIGS. 9A and 9B), substantially sinusoidal (as labeled with reference numeral 458), or substantially spiral (configuration not shown). Alternatively, elongate coagulation members 452 are configured to assume amorphous and/or random shapes, such as steel wool.

For some applications, each of elongate coagulation members 452 further comprises of a plurality of coagulation-fibers 460, which are connected to elongate coagulation member 452 and distributed therealong. For some applications, coagulation-fibers 460 have an average diameter of between 0.01 and 0.1 mm, and/or an average length of between 1 and 15 mm.

For some applications, such as shown in FIG. 9B, external coagulation inducer 450 comprises a plurality of non-contiguous external coagulation regions 490, e.g., two non-contiguous external coagulation regions 490 that are configured to impede blood flow at the renal arteries' respective gutters.

Figure 10B:
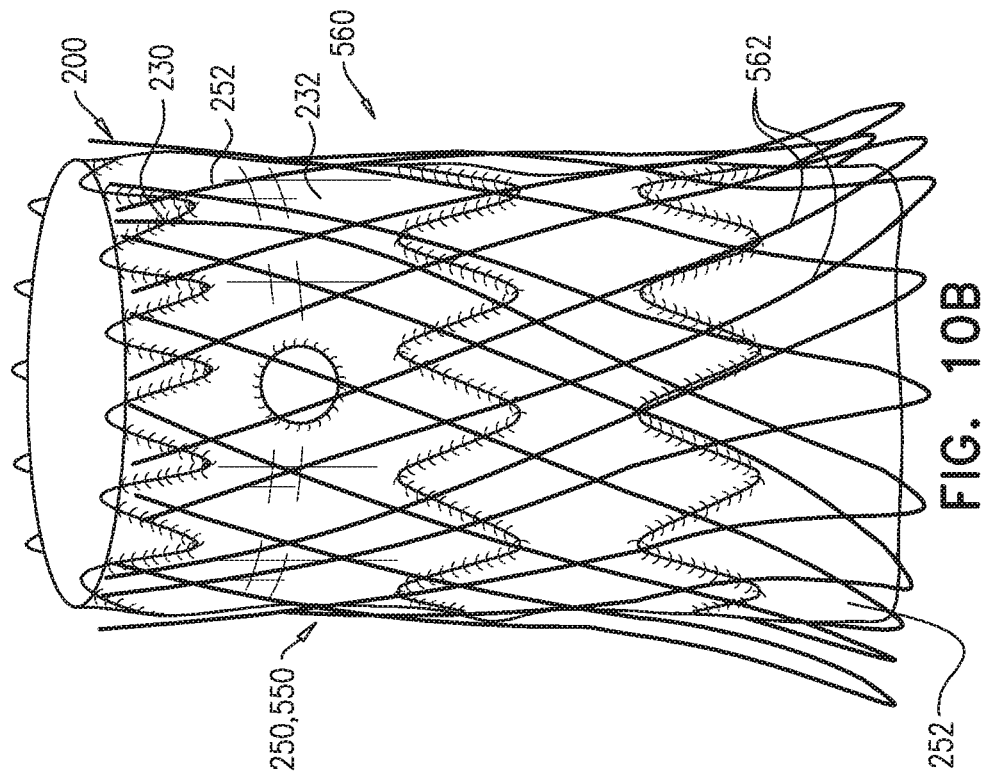
FIGS. 10A-B are schematic illustrations of additional configurations of the endovascular prosthesis of FIGS. 7A-B, in accordance with respective applications of the present invention.
Figure 10A:
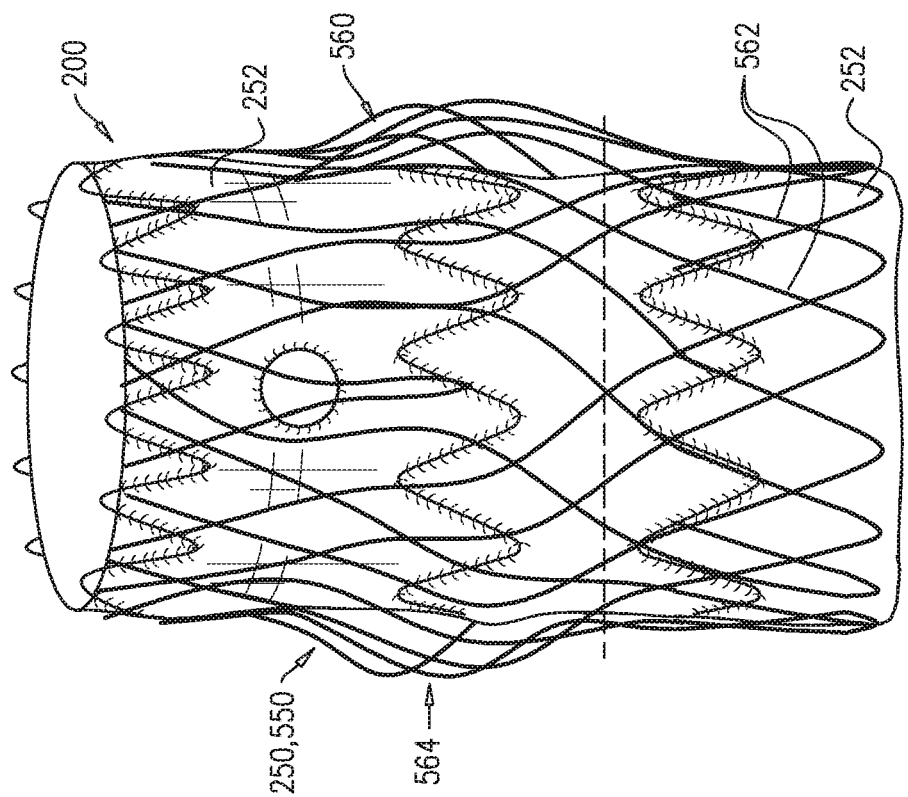

Reference is now made to FIGS. 10A-B, which are schematic illustrations of additional configurations of endovascular prosthesis 200, in accordance with respective applications of the present invention. In these configurations, external coagulation inducer 250 comprises an external coagulation inducer 550, which comprises an extra-luminal skirt 560, which comprises a fiber mesh 562. Typically, at least 50% of an outer surface of fiber mesh 562 is not covered (either inside or outside) with graft material, such as at least 80%, or at least 100% (as shown). For some applications, extra-luminal skirt 560 further comprises graft material, which covers less than 50% of the outer surface of fiber mesh 562 (configuration not shown).

Extra-luminal skirt 560 is configured to assume (i) when endovascular prosthesis 200 is removably disposed in the delivery sheath, a radially-compressed delivery state, and (ii) when endovascular prosthesis 200 is unconstrained, such as shown in FIGS. 10A-B, a radially-expanded state, in which extra-luminal skirt 560 extends radially outward from external surface 252 of stent-graft 240.

For some applications, external coagulation inducer 550 comprises a plurality of extra-luminal skirts 560 (configuration not shown).

For some applications, extra-luminal skirt 560 completely circumferentially encircles stent-graft 240. For other applications, extra-luminal skirt 560 only partially circumferentially encircles stent-graft 240.

For some applications, such as shown in FIG. 10A, extra-luminal skirt 560 (a) widens (e.g., monotonically) in a proximal-to-distal direction to a longitudinal location 564 having a greatest skirt outer cross-sectional area, and (b) narrows (e.g., monotonically) in a proximal-to-distal direction from longitudinal location 564 having the greatest skirt outer cross-sectional area, when endovascular prosthesis 200 is unconstrained in the radially-expanded state. In other words, extra-luminal skirt 560 defines a bulge, and/or is convex when viewed from outside.

For other applications, such as shown in FIG. 10B, extra-luminal skirt 560 monotonically widens along an entire length of extra-luminal skirt 560, when endovascular prosthesis 200 is unconstrained in the radially-expanded state, either in a proximal-to-distal direction (as shown) or a distal-to-proximal direction (configuration not shown).

For some applications, a greatest external perimeter of extra-luminal skirt 560 equals at least 110% of a greatest external perimeter of stent-graft 240, when endovascular prosthesis 200 is unconstrained in the radially-expanded state.

For some applications, extra-luminal skirt 560 adds less than 30% (e.g., less than 20%) to a diameter of the stent-graft when endovascular prosthesis 200 is removably disposed in the delivery sheath in the radially-compressed delivery state.

For some applications, fiber mesh 562 comprises Nitinol. For some applications, fiber mesh 562 comprises a polymer coating. For some applications, fiber mesh 562 comprises braided fibers. For some applications, fiber mesh 562 comprises fibers that are arranged to slide with respect to each other so as to cause a change in outer diameter of extra-luminal skirt 560. Alternatively or additionally, for some applications, fiber mesh 562 is arranged such that a change in an axial length of extra-luminal skirt 560 causes a change in an outer diameter of extra-luminal skirt 560. To this end, typically only one axial end of extra-luminal skirt 560 is axially fixed with respect to stent-graft 240.

Figure 11A:
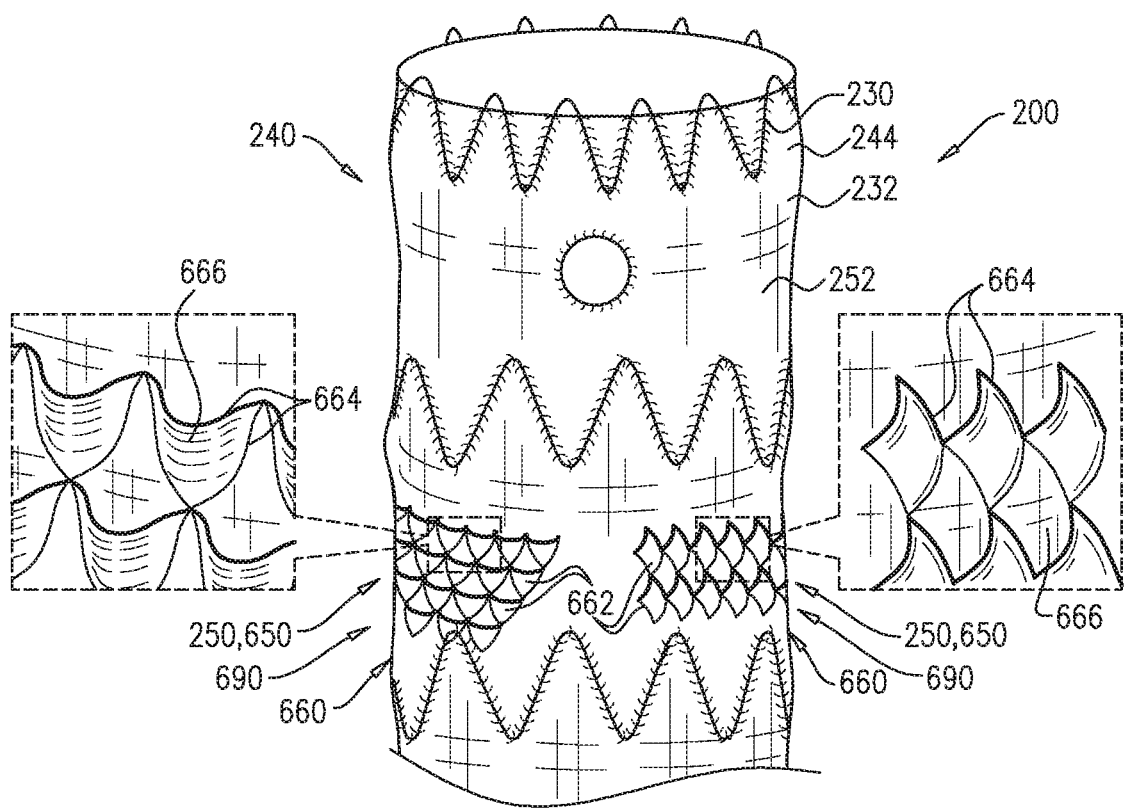
FIGS. 11A-C are schematic illustrations of another configuration of the endovascular prosthesis of FIGS. 7A-B, in accordance with an application of the present invention.
Figure 11B:
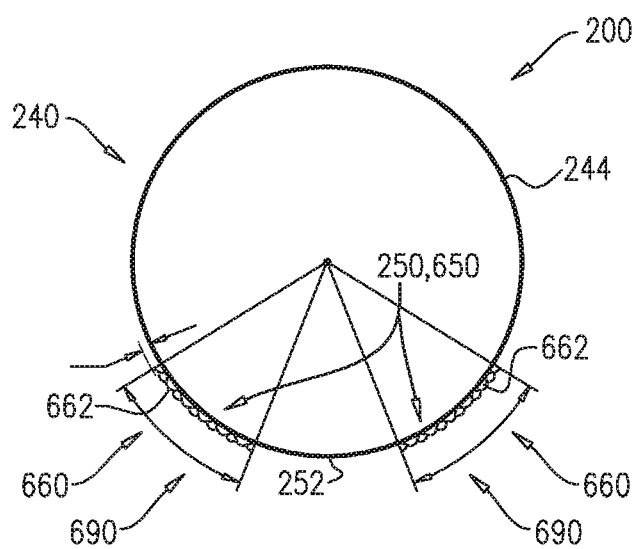
Figure 11C:
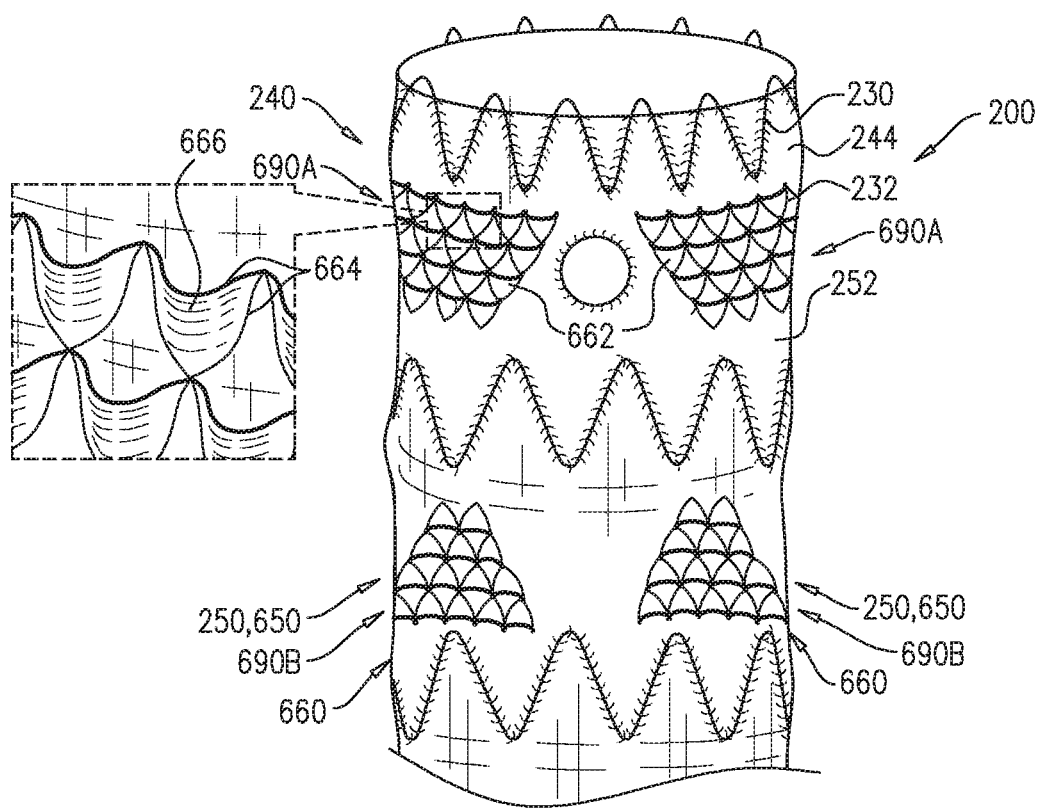

Reference is now made to FIGS. 11A-C, which are schematic illustrations of another configuration of endovascular prosthesis 200, in accordance with an application of the present invention. FIG. 11B is a cross-sectional view of a configuration of endovascular prosthesis 200. In this configuration, external coagulation inducer 250 comprises an external coagulation inducer 650, which comprises one or more scales-segment members 660, such as two or three scales-segment members 660, each of which (a) comprises a plurality of scales 662, such as 25-80 scales 662, (b) is fixed, at at least one point along scales-segment member 660, to external surface 252 of stent-graft 240 both when stent-graft 240 is and is not removably disposed in the delivery sheath, and (c) extends around at least 20 mm (e.g., at least 30 mm) of a circumference of stent-graft 240. Typically, scales 662 extend, on average, around at least 5 mm of the circumference of stent-graft 240. (As used in the present application, including in the claims, an "average" means an arithmetic mean, unless otherwise defined.)

FIG. 11A shows two different types of scales 662. In practice, endovascular prosthesis 200 may comprise a combination of different types of scales 662, such as shown in FIG. 11A, or a single type of scale 662, such as shown in FIGS. 11B and 11C. Typically, scales 662 are configured to assume a radially-compressed state and a radially-expanded state.

For some applications, such as shown in FIGS. 11A-C, external coagulation inducer 650 comprises a plurality of non-contiguous external coagulation regions 690, e.g., two non-contiguous external coagulation regions 690 that are configured to impede blood flow at the renal arteries' respective gutters.

For some applications, each of scales 662 comprises a scale structural member 664 and a scale graft member 666, and scale structural member 664 is biased to increase an effective radial extent of scale 662 when scale 662 is radially unconstrained. For some applications, scale structural member 664 comprises a self-expandable elongate member, such as a self-expandable wire, e.g., comprising Nitinol. Scale graft member 666 may have any of the characteristics of graft member 232, described hereinabove with reference to FIGS. 7A-8.

For some applications, as shown in the left scales-segment members 660 in FIG. 11A and all scales-segment members 660 in FIGS. 11B and 11C, a planar shape of each of one or more (e.g., all) of scales 662 is a triangle with a proximally-facing base. For other applications, as shown in the right scales-segment members 660 in FIG. 11A, a planar shape of each of one or more (e.g., all) of scales 662 is a deltoid with proximally, distally, and laterally oriented vertices.

For some applications, a planar shape of each of one or more of scales-segment members 660 is a rectangle. For other applications, a planar shape of each of one or more of the scales-segment members 660 is a parallelogram.

For some applications, an average radial extent of scales 662, when radially expanded, is at least 3 millimeters. For some applications, when endovascular prosthesis 200 is unconstrained in the radially-expanded state, at least one of scales-segment members 660, taken alone, circumscribes an arc having an angle of at least 50 degrees.

For some applications, at least one of scales 662 is open proximally (i.e., upstream) and attached to external surface 252 of stent-graft 240 at a distal (i.e., downstream) portion of the scale. In other words, each of scales 662 is shaped as a pouch with a proximally-pointing opening.

For some applications, such as shown in FIG. 11C, external coagulation inducer 650 comprises at least one proximal coagulation region 690A and at least one distal coagulation region 690B, disposed more distally than the at least one proximal coagulation region 690A. For some of these applications, the openings of scales 662 of the two regions face in opposite directions; for example, the openings of the scales of the at least one proximal coagulation region 690A may face proximally, and the openings of the scales of the at least one distal coagulation region 690B may face distally, such as shown in FIG. 11C; as a result, the at least one proximal coagulation region 690A may prevent leakage from a chimney (i.e., from above), and the at least one distal coagulation region 690B may prevent retrograde leakage from a "periscope" (i.e., from below), such as described hereinbelow with reference to FIG. 16.

Figure 12A:
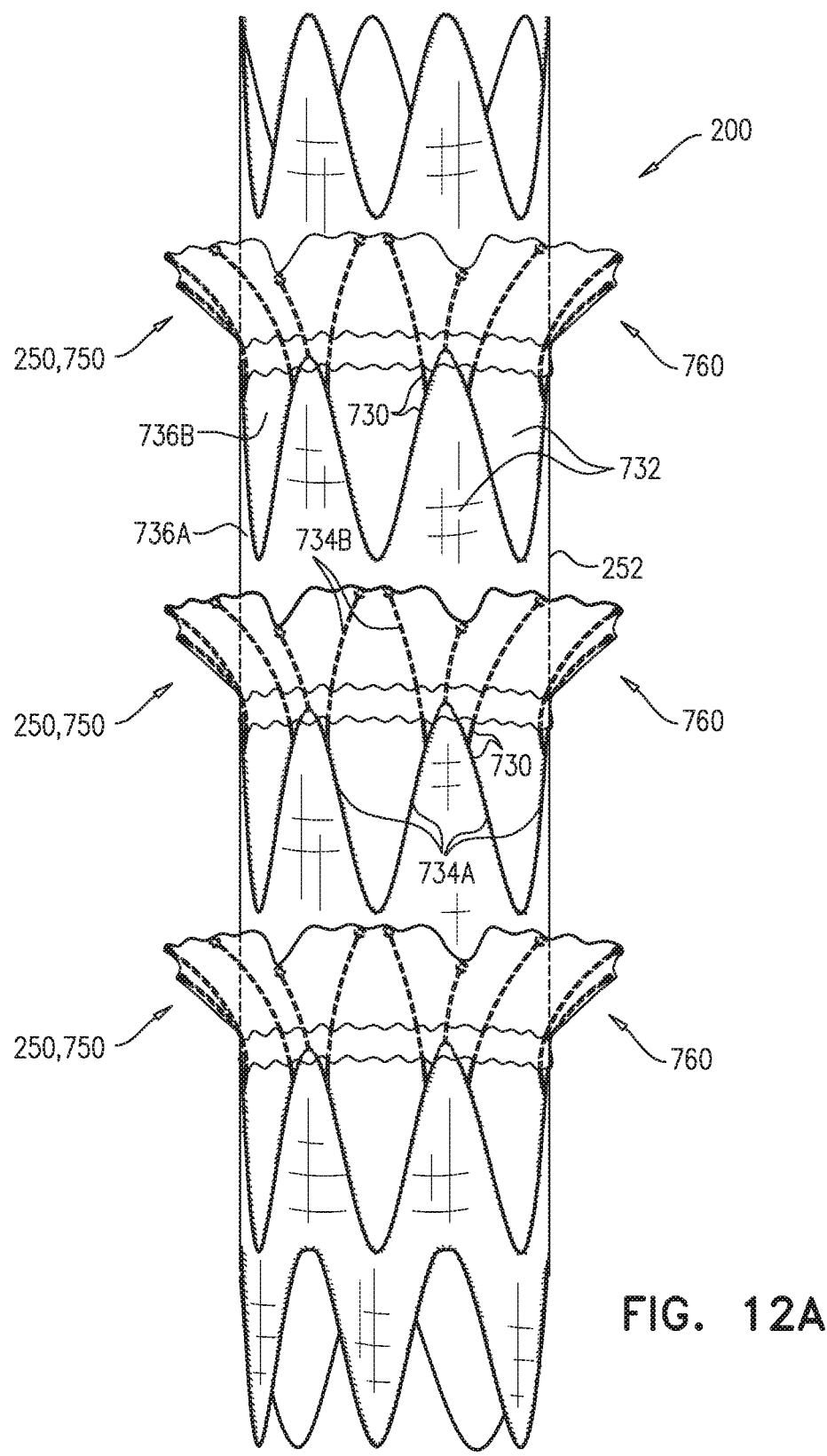
FIGS. 12A-B are schematic illustrations of yet other configurations of the endovascular prosthesis of FIGS. 7A-B, in accordance with respective applications of the present invention.
Figure 12B:
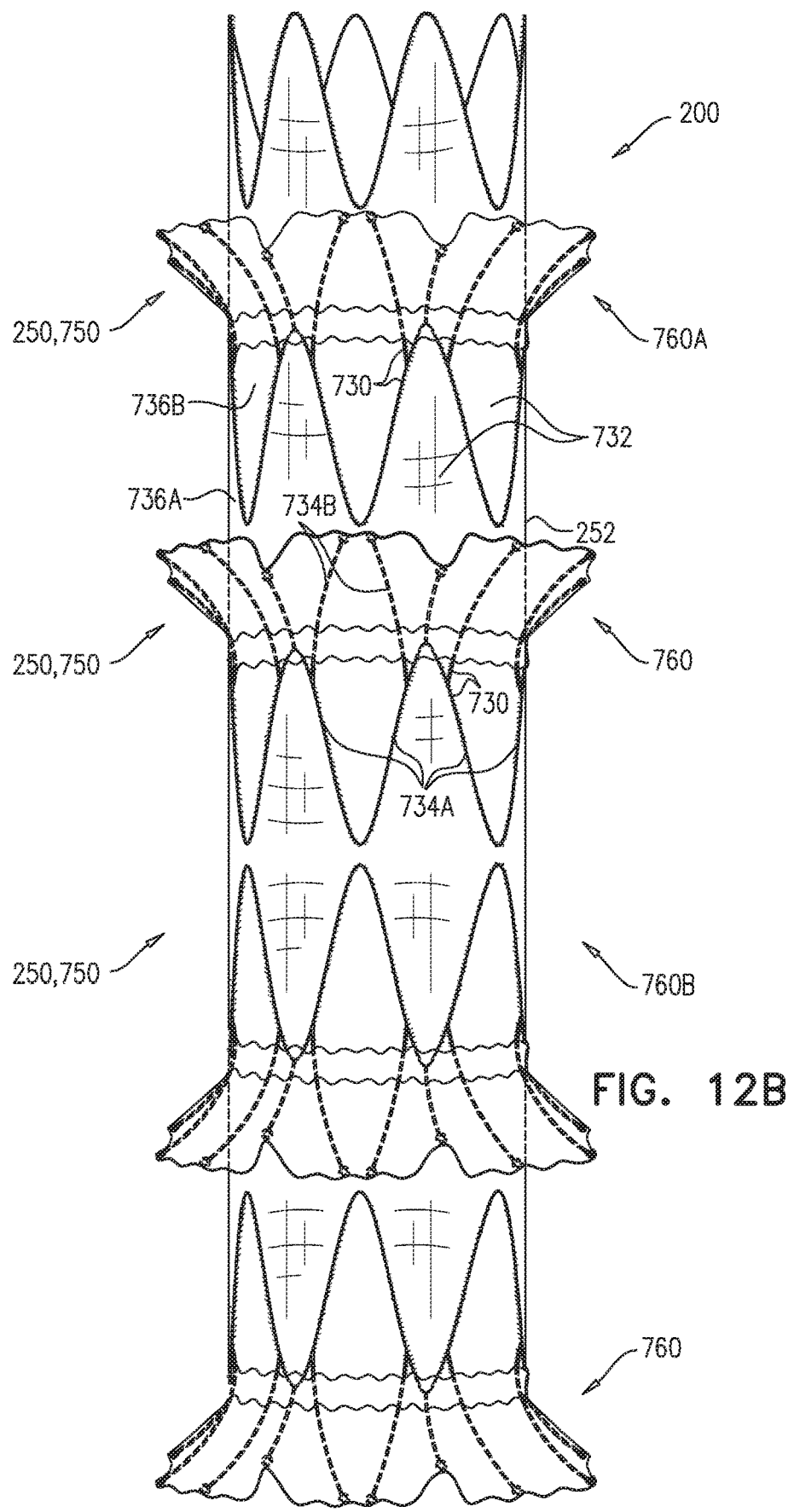

Reference is now made to FIGS. 12A-B, which are schematic illustrations of yet other configurations of endovascular prosthesis 200, in accordance with respective applications of the present invention. In this configuration, external coagulation inducer 250 comprises an external coagulation inducer 750, which comprises an extra-luminal skirt 760. Extra-luminal skirt 760 is configured to reduce the likelihood of long-term leakage (i.e., blood flow) through gutters, i.e., the residual intravascular space disposed outside the lumens of endovascular prosthesis 200 and branching stent-grafts disposed alongside endovascular prosthesis 200. As a result, the likelihood of type 1 endoleak is reduced, in this configuration, endovascular prosthesis 200 comprises structural strut members 730 and a graft member 732. Structural strut members 730 may have any of the characteristics of structural strut members 230 described hereinabove with reference to FIGS. 7A-8. Graft member 732 may have any of the characteristics of graft member 232 described hereinabove with reference to FIGS. 7A-8, including that graft member 732 may comprise one or more biologically-compatible substantially blood-impervious thin flexible sheets.

In this configuration, stent-graft 240 comprises a first portion 734A of structural strut members 730 and a first portion 7364 of graft member 732. Structural strut members 730 of first portion 734A and graft member 732 of first portion 736A are attached to each other, and, when endovascular prosthesis 200 is unconstrained in the radially-expanded state, together are shaped so as to define a blood-carrying tubular structure defining a lumen.

Extra-luminal skirt 760 comprises a second portion 734B of structural strut members 730 and a second portion 73613 of graft member 732 (as mentioned above, graft member 732 may comprise a plurality of biologically-compatible substantially blood-impervious thin flexible sheets). Extra-luminal skirt 760 is configured to assume:
  a radially-compressed delivery state when endovascular prosthesis 200 is removably disposed in the delivery sheath; in this state, structural strut members 730 of first portion 734A do not coincide with structural strut members 730 of second portion 734B (as described hereinbelow with reference to FIG. 13), and
  a radially-expanded state when endovascular prosthesis 200 is unconstrained; in this state, extra-luminal skirt 760 extends radially outward from external surface 252 of stent-graft 240, such as shown in FIGS. 12A-B.

For some applications, external coagulation inducer 750 comprises a plurality of extra-luminal skirts 760, such as shown in FIGS. 12A-B. For some applications, such as shown in FIG. 12B, a first one 760A of the plurality of extra-luminal skirts 760 is disposed proximally (i.e., upstream) to a second one 7608 of the plurality of extra-luminal skirts 760, and, when endovascular prosthesis 200 is unconstrained in the radially-expanded state: (a) the first extra-luminal skirt 760A monotonically widens in a distal-to-proximal direction along an entire length of the first extra-luminal skirt 760A, and (b) the second extra-luminal skirt 760B monotonically widens in a proximal-to-distal direction along an entire length of the second extra-luminal skirt 760B. As a result, first extra-luminal skirt 760A may prevent leakage from a chimney (i.e., from above), and second extra-luminal skirt 760B may prevent retrograde leakage from a "periscope" (i.e., from below), such as described hereinbelow with reference to FIG. 16.

For some applications, first and second ones of the first extra-luminal skirts 760A monotonically widen in a same axial direction (e.g., a distal-to-proximal direction, as shown in FIG. 12B) along respective entire lengths of the first and the second ones of the first extra-luminal skirts 760A. Alternatively or additionally, for some applications, first and second ones of the second extra-luminal skirts 760B monotonically widen in a same axial direction (e.g., a proximal-to-distal direction, as shown in FIG. 12B) along entire respective lengths of the first and the second ones of the second extra-luminal skirts 760B.

For some applications, extra-luminal skirt 760 completely circumferentially encircles stent-graft 240. For other applications, extra-luminal skirt 760 only partially circumferentially encircles stent-graft 240.

For some applications, extra-luminal skirt 760 monotonically widens along an entire length of extra-luminal skirt 760, when endovascular prosthesis 200 is unconstrained in the radially-expanded state, either in a distal-to-proximal direction (as shown in FIGS. 12A and 12B) or a proximal-to-distal direction (as shown in FIG. 12B). For some applications, a greatest external perimeter of extra-luminal skirt 760 equals at least 110% of a greatest external perimeter of stent-graft 240, when endovascular prosthesis 200 is unconstrained in the radially-expanded state.

Figure 13:
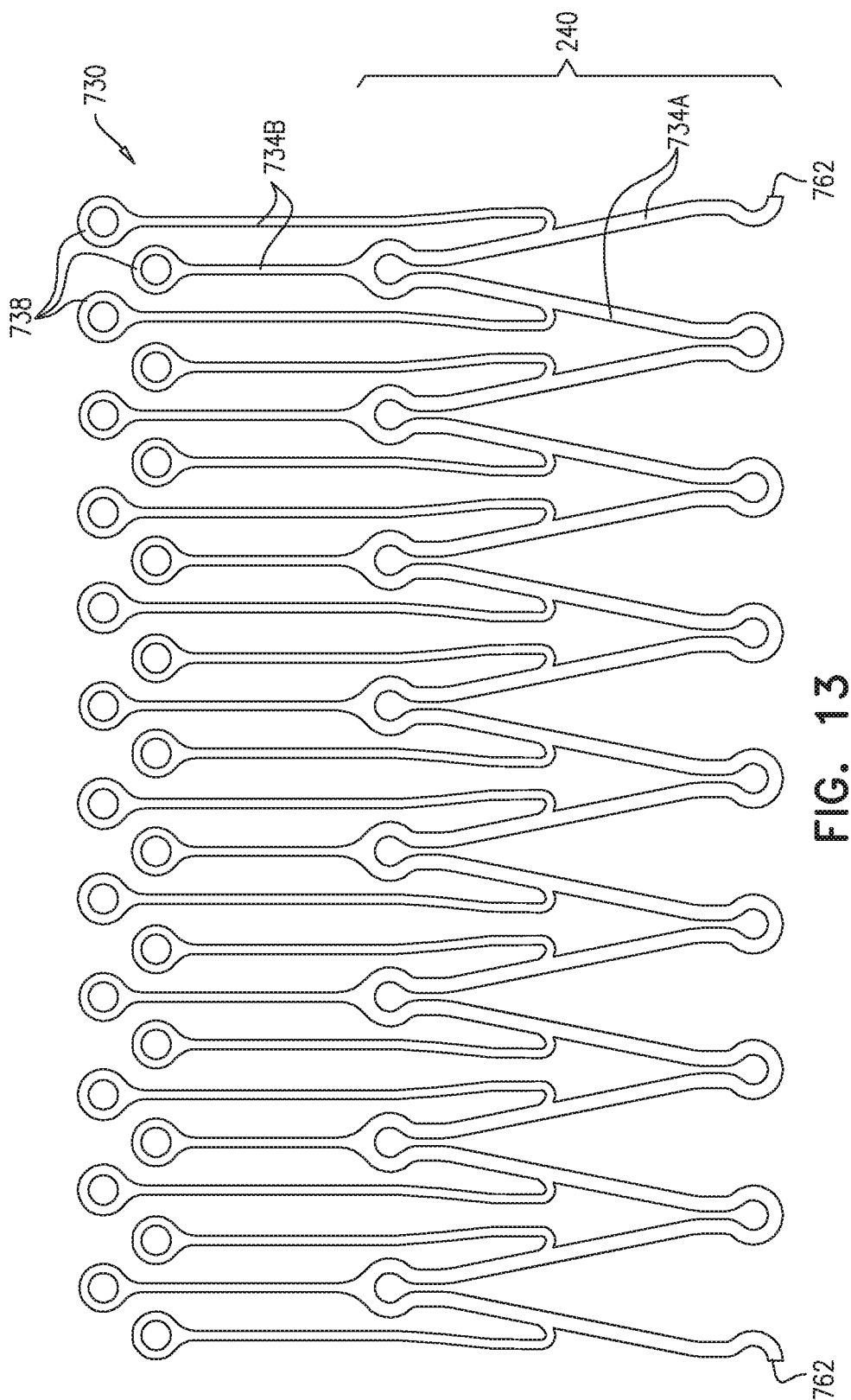
FIG. 13 is a schematic illustration of a set of structural strut members of the endovascular prostheses of FIGS. 12A-B, in accordance with an application of the present invention.

Reference is still made to FIGS. 12A-B, and is additionally made to FIG. 13, which is a schematic illustration of a set of structural strut members 730, in accordance with an application of the present invention. The set of structural strut members 730 is shown cut at a circumferential site 762 of one of structural strut members 730 of first portion 734A and laid flat; in the finished endovascular prosthesis 200, the left side of the set of structural strut members 730 is joined to the right side of set of structural strut members 730 to form a generally tubular structure. The set of structural strut members 730 defines the structure of a single extra-luminal skirt 760 and a single band that supports stent-graft 240. Structural strut members of first portion 734A 730 define the band of stent-graft 240, and structural strut members 730 of second portion 734B define the structure of extra-luminal skirt 760.

As mentioned above with reference to FIGS. 12A-B, extra-luminal skirt 760 is configured to assume a radially-compressed delivery state when endovascular prosthesis 200 is removably disposed in the delivery sheath. In this state, structural strut members 730 of first portion 734A do not coincide with structural strut members 730 of second portion 734B. In other words, if structural strut members 730 are cut at circumferential site 762 of one of structural strut members 730 of first portion 734A and laid flat, as shown in FIG. 13, structural strut members 730 of first portion 734A do not overlap structural strut members 730 of second portion 734B, i.e., do not occupy any of the same locations in the plane. This arrangement of structural strut members 730 avoids the increased crossing profile in the radially-compressed delivery state that would result if the structural strut members overlapped one another. As a result, for some applications, extra-luminal skirt 760 adds less than 30% (e.g., less than 20%) to a diameter of the stent-graft when endovascular prosthesis 200 is removably disposed in the delivery sheath in the radially-compressed delivery state.

For some applications, as shown in FIGS. 12A-B and 13, (a) first and second portions 734A and 734B are fabricated from a single piece of a tubular material (e.g., by laser cutting the material), (b) structural strut members 730 of second portion 734B are directly connected to structural strut members 730 of first portion 734A, (b) none of structural strut members 730 of second portion 734B is directly connected to any of the other structural strut members 730 of second portion 734B, and none of structural strut members 730 of second portion 734B is indirectly stent-connected to any of the other structural strut members 730 of second portion 734B other than via one or more of structural strut members 730 of first portion 734A. (In addition to being indirectly stent-connected, i.e., indirectly connected by stent struts, structural strut members 730 of second portion 734B are typically also indirectly connected by graft member 732.) This arrangement of structural strut members 730 allows each circumferential portion of extra-luminal skirt 760 to radially expand generally separately from one another, because circumferentially-adjacent end portions of structural strut members 730 of second portion 734B do not pull on each other.

For some applications, structural strut members 730 of second portion 734B are thinner on average than structural strut members 730 of first portion 734A. Loops 738 defined by structural strut members 730 function as suturing rings.

For some applications, when endovascular prosthesis 200 is unconstrained in the radially-expanded state, structural strut members 730 of second portion 734B extend radially outward from external surface 252 of stent-graft 240 at an angle of between 30 and 40 degrees with external surface 252.

Figure 14B:
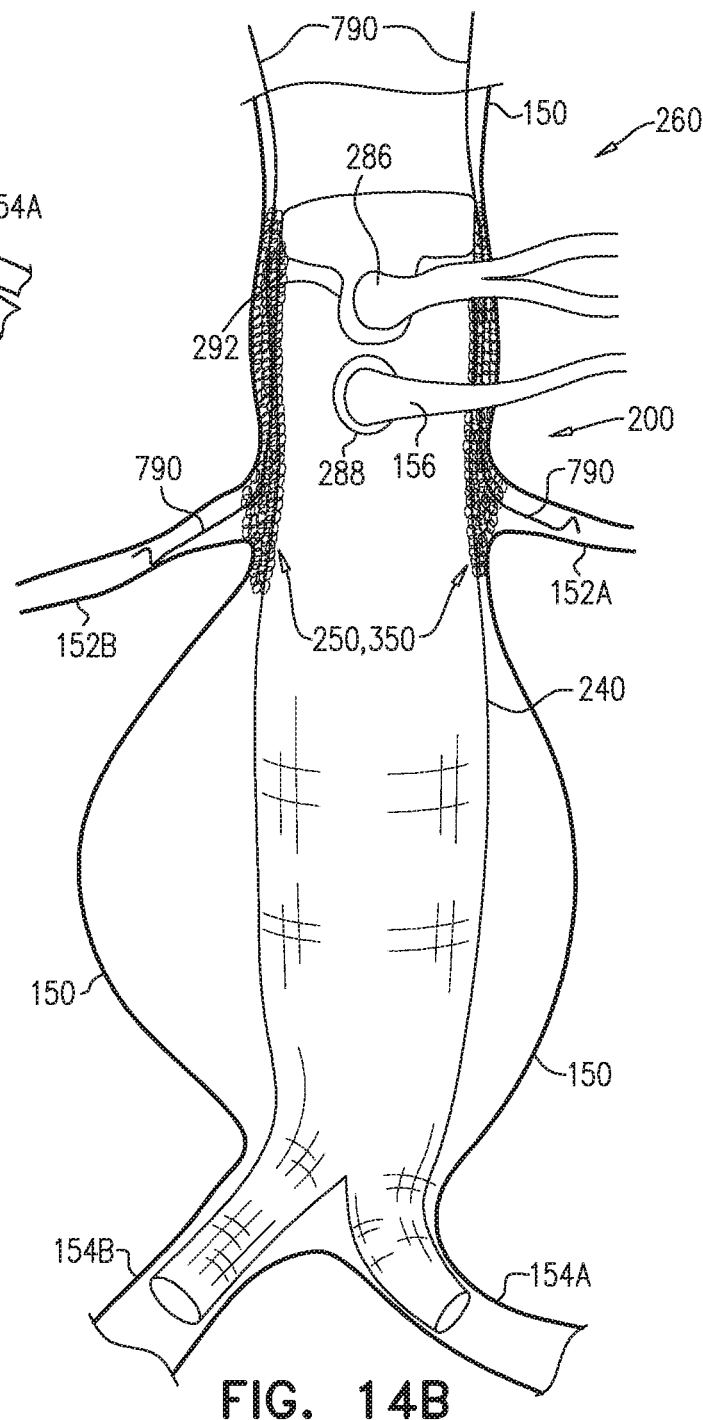
Figure 14C:
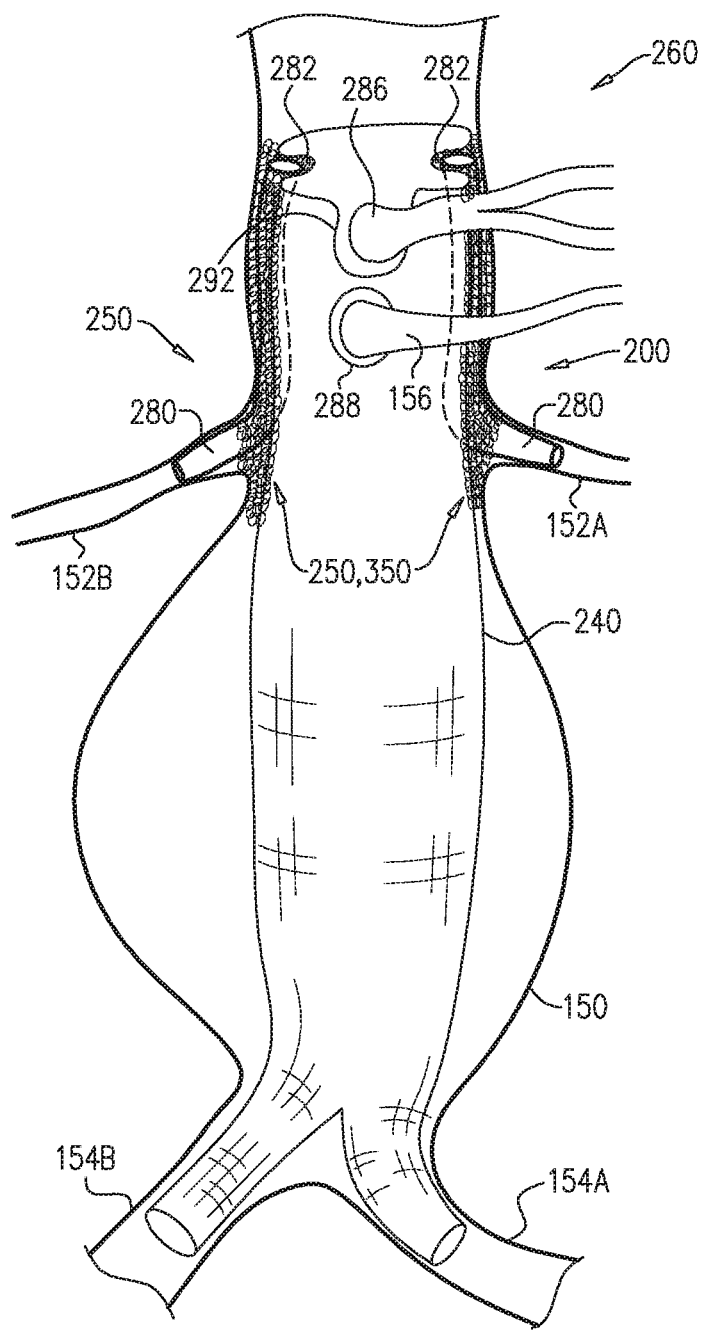

Reference is now made to FIGS. 14A-C, which are schematic illustrations of three stages of an exemplary transvascular delivery procedure for deploying endovascular system 260 in an aneurysmal descending aorta 150, in accordance with an application of the present invention. This deployment is typically used for treating dilations that are distal (i.e., downstream) to branching arteries, such as left and right renal arteries 152A and 152B. FIGS. 14A-C schematically show a portion of a typical aorta 150, as well as left and right renal arteries 152A and 152B, left and right iliac arteries 154A and 154B, superior mesenteric artery (SMA) 156 (which is on the anterior surface of the aorta), and celiac artery 286. Endovascular system 260 may be used to treat a blood vessel, such as an artery, e.g., descending aorta 150, suffering from an aneurysm, a dissection, or, more generally, a pathologically dilated blood vessel. Although FIGS. 14A-C illustrate the deployment using the particular configuration of external coagulation inducer 250 shown in FIGS. 7A-8 (external coagulation inducer 350), the other configurations of external coagulation inducer 250 described herein may be similarly used. In this deployment, stent-graft 240 is a main stent-graft 240.

As shown in FIG. 14A, endovascular prosthesis 200 is deployed using endovascular delivery tool 770, which typically comprises delivery sheath 772, a distal tip 774, and a guidewire 776. Endovascular prosthesis 200 is initially positioned in delivery sheath 772, restrained in the radially-compressed delivery state by sheath 772. Endovascular prosthesis 200 is transvascularly (typically percutaneously) introduced into aorta 150, e.g., via one of iliac arteries 154A or 154B, while positioned in delivery sheath 772. In this exemplary deployment, delivery sheath 772 and distal tip 774 are advanced over guidewire 776 until the distal tip is positioned at or above renal arteries 152A and 152B.

FIG. 14B shows endovascular prosthesis 200 upon deployment thereof in descending aorta 150, spanning left and right renal arteries 152A and 152B, after delivery sheath 772 has been withdrawn to release the prosthesis. Techniques for deployment may be used that are described in one or more of the patent applications incorporated hereinbelow by reference, or otherwise known in the art. Although the deployment is illustrated with reference to the descending aorta, renal arteries, SMA, and the celiac artery, endovascular system 260 may also be deployed in the vicinity of other main and branching blood vessels, such as arteries, e.g., visceral arteries. For some applications, a smallest one of the one or more branching arteries has a proximal diameter that is no more than 30% (e.g., no more than 20%) of a diameter of the main artery at a branching location. Typically, respective guidewires 790 are introduced into the branching arteries before deployment of endovascular prosthesis 200.

FIG. 14C shows endovascular system 260 upon the additional deployment of two branching stent-grafts 280, typically using guidewires 790. The two branching stent-grafts 280 are positioned partially extending along a portion of endovascular prosthesis 200 and into respective branching arteries: left renal artery 152A and right renal artery 152B, such that portions of branching stent-grafts 280 contact external coagulation inducer 250. These branching prostheses thus provide a blood-flow path from the main artery to the branching arteries. External coagulation inducer 250 reduces the likelihood of long-term leakage (i.e., blood flow) through "gutters" 282. As a result, the likelihood of type 1 endoleak is reduced.

Typically, respective proximal ends of branching stent-grafts 280 are disposed at or near a proximal end of endovascular prosthesis 200, such as within 2 cm of the proximal end of endovascular prosthesis 200 (either proximal or distal the proximal end). Preferably, the respective proximal ends of branching stent-grafts 280 are disposed not proximally to the proximal end of endovascular prosthesis 200, because if they were disposed proximally to the proximal end of endovascular prosthesis 200, blood flow might cause them to bend, curve, and whip in accordance with the aortic systole cycle. Respective distal ends of branching stent-grafts 280 are disposed in left and right renal arteries 152A and 152B.

Optionally, endovascular system 260 includes one or more extension endovascular prostheses, which collectively bypass the aneurysmal sac to left and right iliac arteries 154A and 154B. The extension endovascular prostheses are sealingly coupled to endovascular prosthesis 200 during the deployment procedure. As can be seen in FIG. 14C, upon deployment of all of the endoluminal prostheses, multi-component endovascular system 260 defines a blood-flow path from upstream of the renal arteries to the renal arteries, SMA, celiac artery, and iliac arteries. For some applications, endovascular prosthesis 200 is further shaped so as to define a distal skirt longitudinal portion, such as distal skirt longitudinal portion 42, described hereinabove with reference to FIGS. 1-6B, which may further risk the likelihood of type 1 endoleak. For some applications, a distal portion of endovascular prosthesis 200 is bifurcated, as shown in FIGS. 14A-C.

Figure 15:
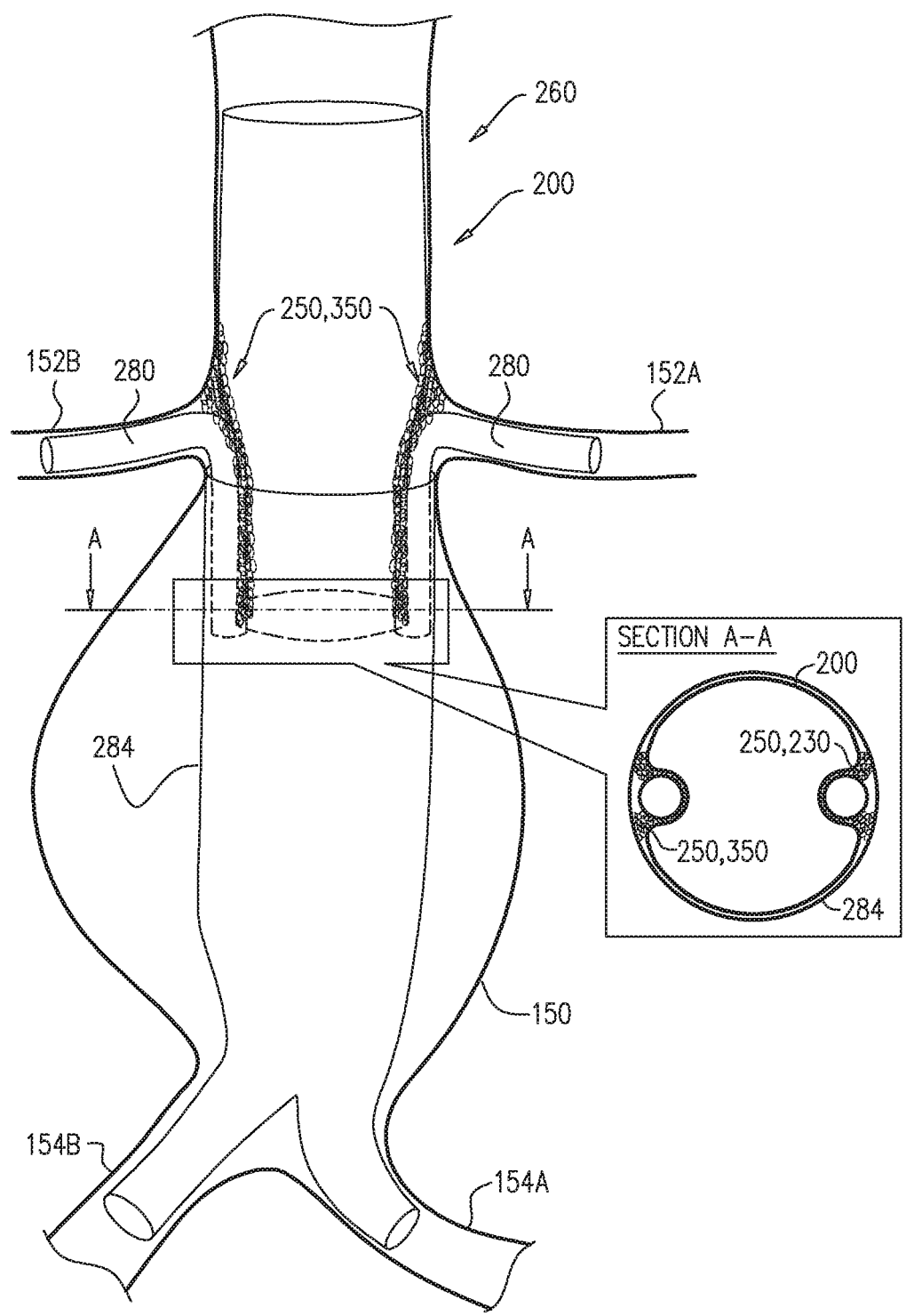
FIG. 15 is schematic illustration of another exemplary deployment of the endovascular prosthesis of FIGS. 7A-B in an aneurysmal descending aorta, in accordance with an application of the present invention.

Reference is now made to FIG. 15, which is schematic illustration of another exemplary deployment of endovascular system 260 in an aneurysmal descending aorta 150, in accordance with an application of the present invention. This "sandwich" deployment is typically used for treating dilations that are distal (i.e., downstream) to branching arteries, such as left and right renal arteries 152A and 152B. Although FIG. 15 illustrates the deployment using the particular configuration of external coagulation inducer 250 shown in FIGS. 7A-8 (external coagulation inducer 350), the other configurations of external coagulation inducer 250 described herein may be similarly used. In this deployment, stent-graft 240 is a main stent-graft 240.

FIG. 15 shows endovascular system 260 upon deployment of
  endovascular prosthesis 200 in descending aorta 150, spanning left and right renal arteries 152A and 152B,
  two branching stent-grafts 280, positioned extending (a) along a portion of endovascular prosthesis 200 distal (i.e., downstream) to branching left renal and right renal arteries 152A and 152B, and (b) into the renal arteries; these branching prostheses thus provide a blood-flow path from the main artery to the branching arteries. External coagulation inducer 250 reduces the likelihood of long-term leakage (i.e., blood flow) between endovascular prosthesis 200 and branching stent-grafts 280; as a result, the likelihood of type 1 endoleak is reduced, and
  at least one extension endovascular prosthesis 284, which bypasses the aneurysmal sac to left and right iliac arteries 154A and 154B, and which is sealingly coupled to endovascular prosthesis 200 during the deployment procedure.

Upon deployment of all of the endoluminal prostheses, multi-component endovascular system 260 defines a blood-flow path from upstream of the renal arteries to the renal arteries, SMA, celiac artery, and iliac arteries (the SMA and celiac arteries are not shown in FIG. 15, but can be seen in FIGS. 14A-C, for example).

Typically, respective distal ends of branching stent-grafts 280 are disposed at or near a distal end of endovascular prosthesis 200, such as within 2 cm of the distal end of endovascular prosthesis 200 (either proximal or distal the distal end). Respective proximal ends of branching stent-grafts 280 are disposed in left and right renal arteries 152A and 152B.

Figure 16:
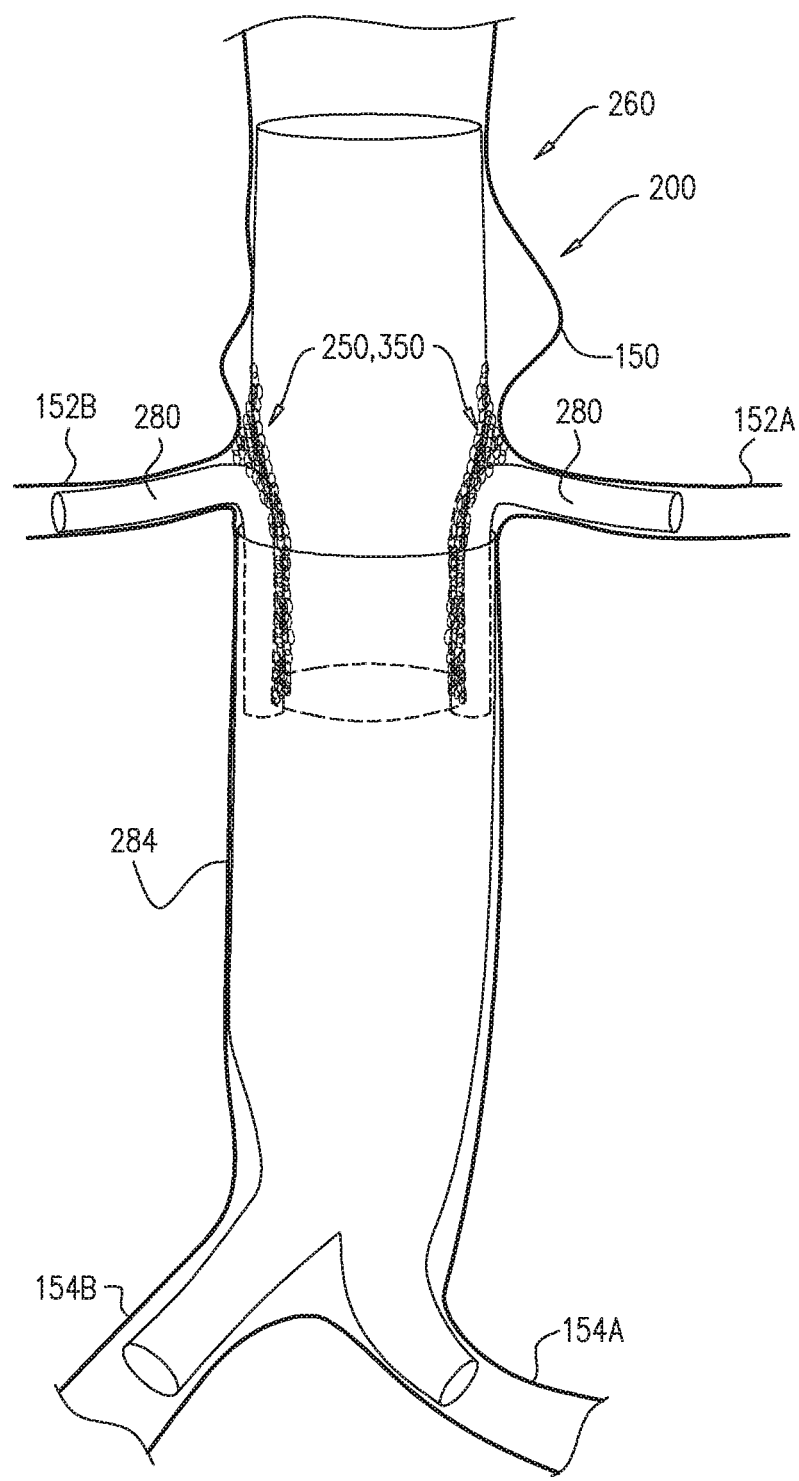
FIG. 16 is schematic illustration of yet another exemplary deployment of the endovascular prosthesis of FIGS. 7A-B in an aneurysmal descending aorta, in accordance with an application of the present invention.

Reference is now made to FIG. 16, which is schematic illustration of yet another exemplary deployment of endovascular system 260 in an aneurysmal descending aorta 150, in accordance with an application of the present invention. This "periscope" deployment is typically used for treating dilations that are proximal (i.e., upstream) to branching arteries, such as left and right renal arteries 152A and 152B. Although FIG. 16 illustrates the deployment using the particular configuration of external coagulation inducer 250 shown in FIGS. 7A-8 (external coagulation inducer 350), the other configurations of external coagulation inducer 250 described herein may be similarly used. In this deployment, stent-graft 240 is a main stent-graft 240.

FIG. 16 shows endovascular system 260 upon deployment of:
  endovascular prosthesis 200 in descending aorta 150, spanning left and right renal arteries 152A and 152B, and
  two branching stent-grafts 280, positioned extending (a) along a portion of endovascular prosthesis 200 distal (i.e., downstream) to branching left renal and right renal arteries 152A and 1523, and (h) into the renal arteries; these branching prostheses thus provide a blood-flow path from the main artery to the branching arteries. External coagulation inducer 250 reduces the likelihood of long-term leakage (i.e., blood flow) between endovascular prosthesis 200 and branching stent-grafts 280; as a result, the likelihood of type 1 endoleak is reduced.

Upon deployment of all of the endoluminal prostheses, multi-component endovascular system 260 defines a blood-flow path from upstream of the renal arteries to the renal arteries, SMA, and celiac artery (the SMA and celiac arteries are not shown in FIG. 16, but can be seen in FIGS. 14A-C, for example). In this configuration, endovascular system 260 typically does not span the portion of the descending aorta between the renal arteries and the iliac arteries, because this portion is typically not dilated; therefore, extension endovascular prostheses are typically not needed.

Typically, respective distal ends of branching stent-grafts 280 are disposed at or near a distal end of endovascular prosthesis 200, such as within 2 cm of the distal end of endovascular prosthesis 200 (either proximal or distal the distal end). Respective proximal ends of branching stent-grafts 280 are disposed in left and right renal arteries 152A and 152B.

Figure 17:
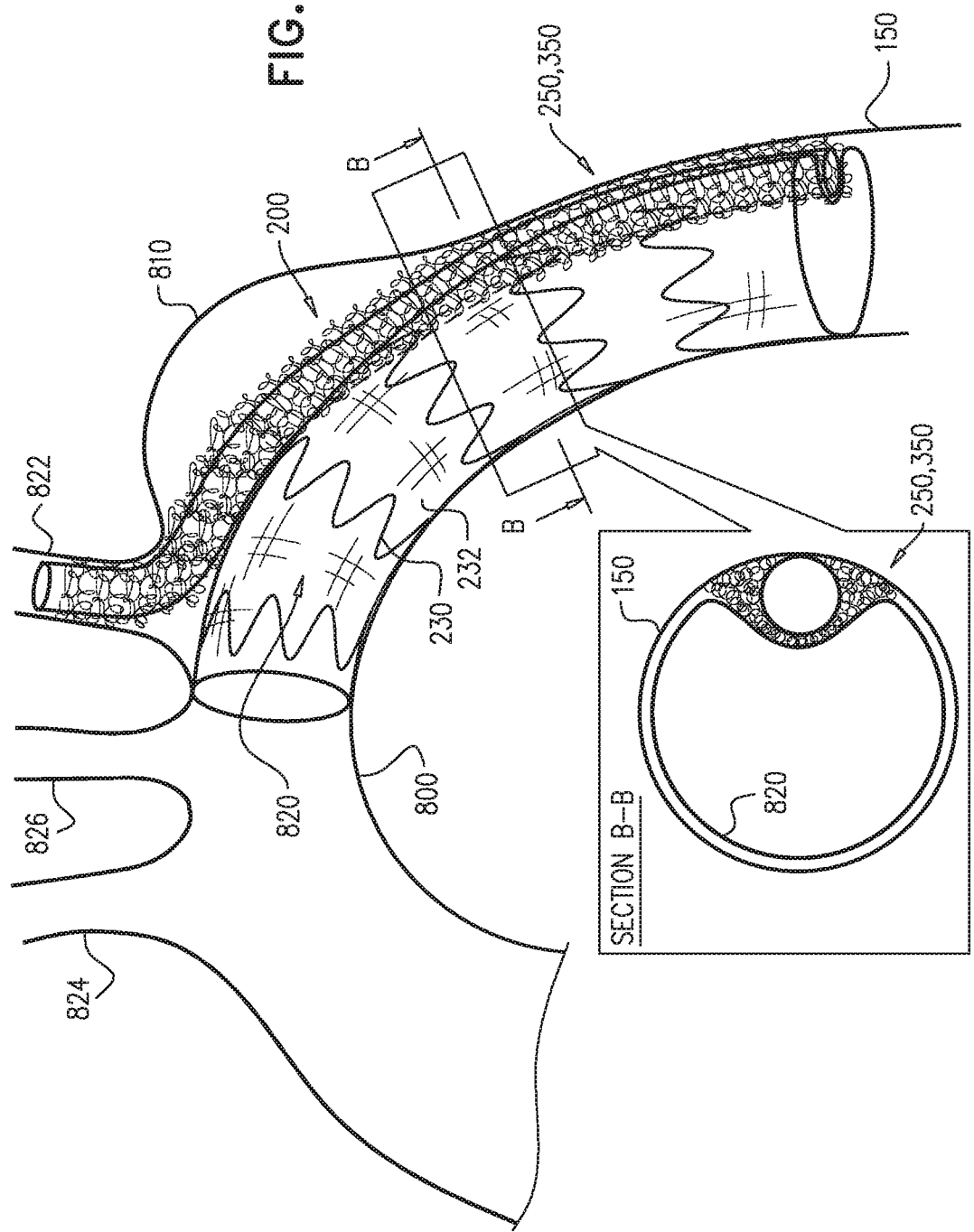
FIG. 17 is a schematic illustration of another configuration of the endovascular prosthesis of FIGS. 7A-B deployed in an aortic arch and an upper portion of a descending aorta, in accordance with an application of the present invention.

Reference is now made to FIG. 17, which is a schematic illustration of another configuration of endovascular prosthesis 200 deployed in an aortic arch 800 and an upper portion of descending aorta 150, in accordance with an application of the present invention in this configuration of endovascular prosthesis 200, external coagulation inducer 250 surrounds an entire circumference of stent-graft 240, when endovascular prosthesis 200 is unconstrained in the radially-expanded state. Typically, external coagulation inducer 250 extends along at least 50% (e.g., at least 75%, such as at least 90%, e.g., 100%) of a total length of stent-graft 240, either longitudinally contiguously (as shown) or in a plurality of longitudinally non-contiguous longitudinal segments (configuration not shown).

In this configuration, endovascular prosthesis 200 may be deployed as a branching stent-graft. Typically, a substantial portion of the length (e.g., at least 50%, such at least 75%) of endovascular prosthesis 200 is disposed alongside a main stent-graft 820, and a portion of endovascular prosthesis 200 is disposed in a branching artery. External coagulation inducer 250 reduces the likelihood of long-term leakage outside the lumens of endovascular prosthesis 200 and main stent-graft 820. For example, in the exemplary deployment shown in FIG. 17, a portion of endovascular prosthesis 200 is disposed in a left subclavian artery 822, and the proximal (i.e., upstream) end of main stent-graft 820 is disposed upstream of the ostium of left subclavian artery 822. A portion of endovascular prosthesis 200 may alternatively deployed in a brachiocephalic artery 824 or a left common carotid artery 826, for example. Endovascular prosthesis 200 and main stent-graft 820 together bypass a dilation 810 of the wall of the aortic arch 800, such as an aneurysm or a dissection.

For some applications, a distal (i.e., downstream) end of endovascular prosthesis 200 is disposed at or near a distal end of and main stent-graft 820, such as within 2 cm of the distal end of main stent-graft 820 (either proximal or distal the proximal end).

For some applications, one end of endovascular prosthesis 200 is disposed in left common carotid artery 826 or brachiocephalic artery 824, and the other end of endovascular prosthesis 200 is disposed either distally in aorta 150 (similar to the configuration shown in FIG. 17), or proximally in a chimney configuration (i.e., with antegrade blood flow rather than retrograde blood flow).

Although FIG. 17 illustrates the deployment using the particular configuration of external coagulation inducer 250 shown in FIGS. 7A-8 (external coagulation inducer 350), the other configurations of external coagulation inducer 250 described herein may be similarly used.

Figure 18:
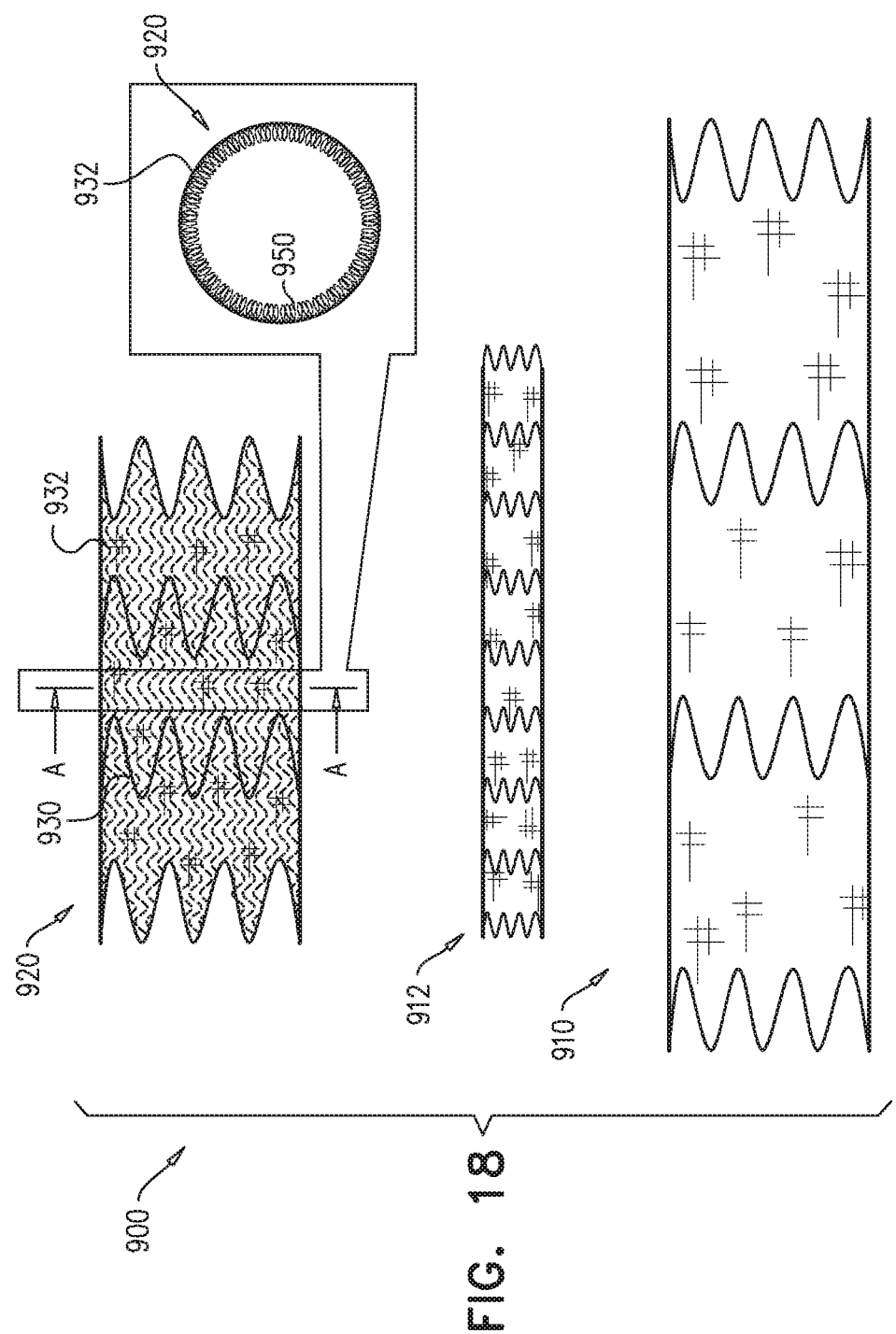
FIG. 18 is a schematic illustration of an endovascular system, in accordance with an application of the present invention.

Reference is now made to FIG. 18, which is a schematic illustration of an endovascular system 900, in accordance with an application of the present invention. Endovascular system 900 comprises a main stent-graft 910, a branching stent-graft 912, and an anti-gutter linking endovascular prosthesis 920. For some applications, main stent-graft 910 and branching stent-graft 912 are conventional stent-grafts, as known in the art, and may be self-expanding or otherwise expandable, such as balloon-expandable; typically, each of the main and the branching stent-grafts comprises structural strut members and a graft member, which may have any of the characteristics of structural strut members 230 and/or graft member 232 described hereinabove with reference to FIGS. 7A-8, mutates mutandis. Typically, main stent-graft 910 is larger than branching stent-graft 912, e.g., may have a larger circumference, e.g., 3-6 times larger than that of branching stent-graft 912, and/or a longer length, e.g., greater than the length of branching stent-graft 912, typically up to 4 times greater (for applications in which main stent-graft 910 comprises a plurality of serially-adjacent modules, the length of the main stent-graft includes the length of the assembly of the modules). Endovascular system 900 typically further comprise an endovascular delivery tool (e.g., comprising a delivery sheath), such as described hereinbelow with reference to FIG. 14A, mutatis mutandis, and/or additional endovascular stent-grafts.

Anti-gutter linking endovascular prosthesis 920 comprises structural strut members 930 and a graft member 932, which may have any of the characteristics of structural strut members 230 and/or graft member 232 described hereinabove with reference to FIGS. 7A-8, mutatis mutandis. Anti-gutter linking endovascular prosthesis 920 further comprises an internal coagulation inducer 950, which is attached to an internal surface of a lumen defined by anti-gutter linking endovascular prosthesis 920. Internal coagulation inducer 950 typically extends entirely around the circumference of anti-gutter linking endovascular prosthesis 920, and typically has an axial length equal to between 10% and 100% (e.g., between 10% and 90%) of the length of anti-gutter linking endovascular prosthesis 920. Internal coagulation inducer 950 may implement any of the configurations of external coagulation inducer 250, described hereinabove with reference to FIGS. 7A-8, 9A-B, 11A-C, and 12A-13, mutatis mutandis (in the case of the configurations of FIGS. 10A-B and 12A-13, the skirt, when implemented in internal coagulation inducer 950, is an intra-luminal skirt rather than an extra-luminal skirt as shown in FIGS. 10A-B and 12A-13). By way of example, internal coagulation inducer 950 is shown implementing the configuration of external coagulation inducer 350, described hereinabove with reference to FIG. 7A-8, mutatis mutandis.

As described hereinbelow with reference to FIGS. 19A-C, main stent-graft 910, branching stent-graft 912, anti-gutter linking endovascular prosthesis 920, and internal coagulation inducer 950 are sized such that main stent-graft 910 and branching stent-graft 912 are disposable alongside each other passing through internal coagulation inducer 950 of anti-gutter linking endovascular prosthesis 920, main stent-graft 910, branching stent-graft 912, and anti-gutter linking endovascular prosthesis 920 are in respective radially-expanded states.

Figure 19A:
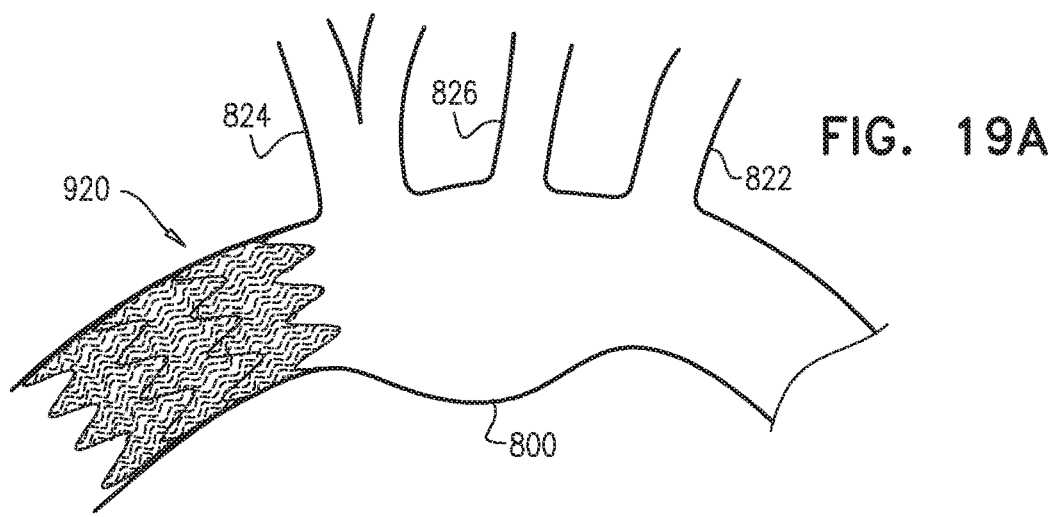
Figure 19B:
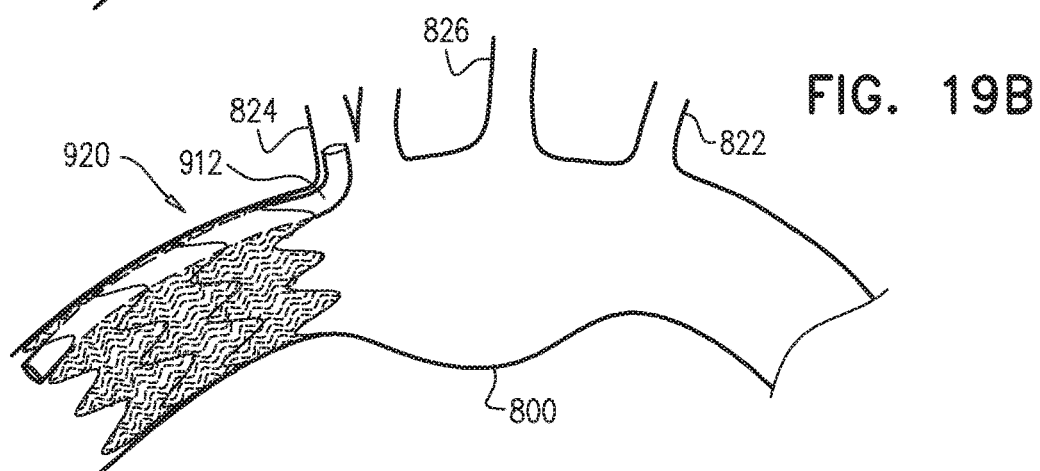
Figure 19C:
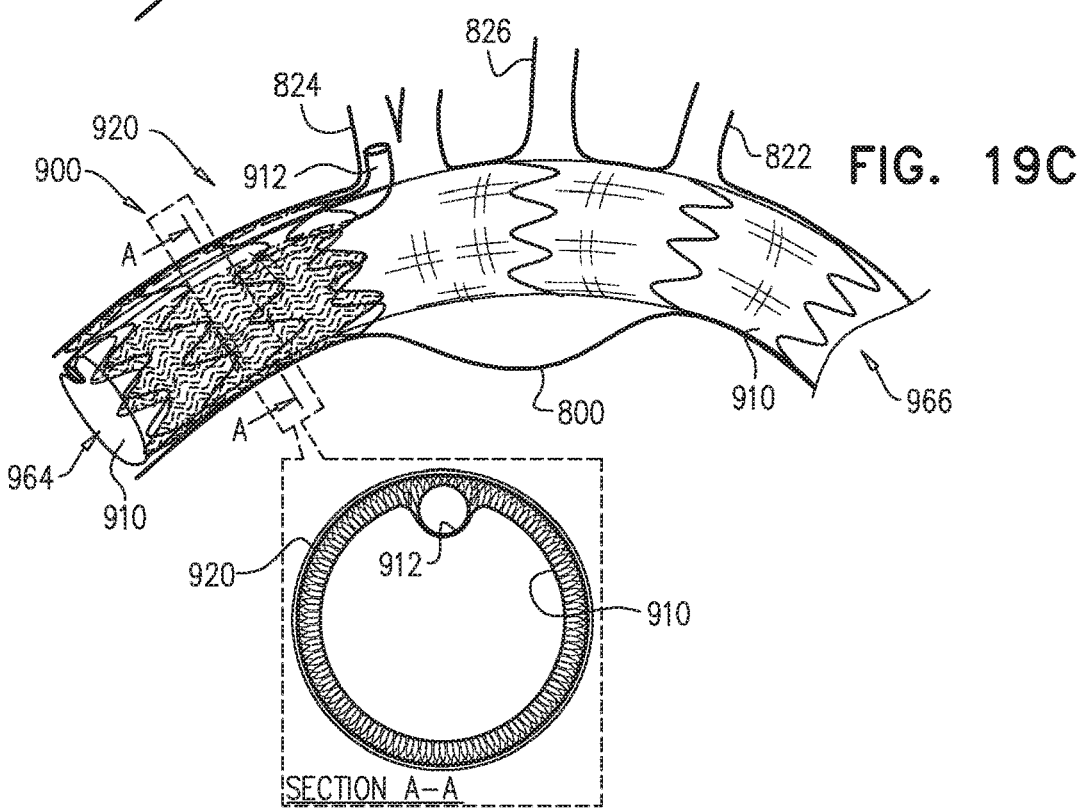

Reference is now made to FIGS. 19A-C, which are schematic illustrations of three stages of an exemplary transvascular delivery procedure for deploying endovascular system 900 in aneurysmal aortic arch 800, in accordance with an application of the present invention. Endovascular system 900 may be used to treat a blood vessel, such as an artery, e.g., aortic arch 800, suffering from an aneurysm, a dissection, or, more generally, a pathologically dilated blood vessel. Although FIGS. 19A-C illustrate the deployment using the particular configuration of internal coagulation inducer 950 shown in FIG. 18, the other configurations of external coagulation inducer 250 described herein may be similarly used.

As shown in FIG. 19A, anti-gutter linking endovascular prosthesis 920 is deployed in the artery, upstream of the branching artery (in the example shown, brachiocephalic artery 824) using the endovascular delivery tool, which typically comprises a delivery sheath similar to delivery sheath 772 described hereinabove with reference to FIG. 19A, a distal tip, and a guidewire. Anti-gutter linking endovascular prosthesis 920 is initially positioned in the delivery sheath, restrained in a radially-compressed delivery state by the sheath. Anti-gutter linking endovascular prosthesis 920 is transvascularly (typically percutaneously) introduced into the aortic arch, e.g., via one of iliac arteries 154A or 154B or one of the arteries that branches off the aortic arch, while positioned in the delivery sheath. For some applications, anti-gutter linking endovascular prosthesis 920 is self-expanding to a radially-expanded state, i.e., is configured to automatically expand during the transition of from the radially-compressed delivery state to the radially-expanded state upon being released from the delivery sheath; alternatively, for example, anti-gutter linking endovascular prosthesis 920 may be balloon-expandable.

As shown in FIG. 19B, branching stent-graft 912 is deployed passing through internal coagulation inducer 950 of anti-gutter linking endovascular prosthesis 920, with (a) a proximal end 960 proximal (i.e., upstream) to anti-gutter linking endovascular prosthesis 920 or axially aligned with the proximal end of the linking prosthesis, and (b) a distal end 962 disposed in a branching artery, such as brachiocephalic artery 824.

As shown in FIG. 19C, main stent-graft 910 is deployed passing through internal coagulation inducer 950 of anti-gutter linking endovascular prosthesis 920, with (a) a proximal end 964 proximal (i.e., upstream) to anti-gutter linking endovascular prosthesis 920 or axially aligned with the proximal end of the linking prosthesis, and (b) a distal end 966 distal (i.e., downstream) to anti-gutter linking endovascular prosthesis 920 or axially aligned with the distal end of the linking prosthesis. Alternatively, main stent-graft 910 is deployed before deploying branching stent-graft 912.

Upon full deployment, main stent-graft 910 and branching stent-graft 912 run parallel to one another through internal coagulation inducer 950 of anti-gutter linking endovascular prosthesis 920, with portions of main stent-graft 910 and branching stent-graft 912 touching internal coagulation inducer 950, such that internal coagulation inducer 950 reduces the likelihood of long-term leakage (i.e., blood flow) through any gutters that might be created outside of the lumens of the main and branching stent-grafts.

In an embodiment, techniques and apparatus described in one or more of the following patents and patent applications, which are assigned to the assignee of the present application and are incorporated herein by reference, are combined with techniques and apparatus described herein.

PCT Application PCT/IL2008/000287, filed Mar. 5, 2008, which published as PCT Publication WO 2008/107885

PCT Application PCT/IB2010/052861, filed Jun. 23, 2010, which published as PCT Publication WO 2010/150208

PCT Application PCT/IL2010/000564, filed Jul. 14, 2010, which published as PCT Publication WO 2011/007354

PCT Application PCT/IL2010/000917, filed Nov. 4, 2010, which published as PCT Publication WO 2011/055364

PCT Application PCT/IL2010/000999, filed Nov. 30, 2010, which published as PCT Publication WO 2011/064782

PCT Application PCT/IL2010/001018, Fled Dec. 2, 2010, which published as PCT Publication WO 2011/067764

PCT Application PCT/IL2010/001037, filed Dec. 8, 2010, which published as PCT Publication WO 2011/070576

PCT Application PCT/IL2011/000135, filed Feb. 8, 2011, which published as PCT Publication WO 2011/095979

PCT Application PCT/IL2012/000060, filed Feb. 2, 2012, which published as PCT Publication WO 2012/104842

PCT Application PCT/IL2012/000241, filed Jun. 19, 2012, which published as PCI Publication WO 2012/176187

PCT Application PCT/IL2012/000300, filed Aug. 12, 2012, which published as PCT Publication WO 2013/030819

U.S. Pat. No. 8,317,856 to Shalee et al.

U.S. Pat. No. 8,574,287 to Benary et al.

U.S. Provisional Application 60/892,885, filed Mar. 5, 2007

U.S. Provisional Application 60/991,726, filed Dec. 2, 2007

U.S. Provisional Application 61/219,758, filed Jun. 23, 2009

U.S. Provisional Application 61/221,074, filed Jun. 28, 2009

U.S. application Ser. No. 13/031,871, Filed Feb. 22, 2011, which published as US Patent Application Publication 2011/0208289

U.S. Provisional Application 61/496,613, filed Jun. 14, 2011

U.S. Provisional Application 61/499,195, filed Jun. 21, 2011

U.S. Provisional Application 61/505,132, filed Jul. 7, 2011

U.S. Provisional Application 61/529,931, filed Sep. 1, 2011

U.S. Provisional Application 61/553,209, filed Oct. 30, 2011

U.S. Pat. No. 8,870,938 to Shalev et al.

U.S. application Ser. No. 13/384,075, filed Jan. 13, 2012, which published as US Patent Application Publication 2012/0179236

U.S. application Ser. No. 13/505,996, filed May 3, 2012, which published as US Patent Application Publication 2012/0310324

U.S. application Ser. No. 13/513,397, filed Jun. 1, 2012, which published as US Patent Application Publication 2012/0330399

U.S. application Ser. No. 13/514,240, filed Jun. 6, 2012, which published as US Patent Application Publication 2013/0013051

U.S. Provisional Application 61/678,182, filed Aug. 1, 2012

U.S. application Ser. No. 13/577,161, filed Aug. 3, 2012, which published as US Patent Application Publication 2013/0035751

U.S. Pat. No. 8,945,203 to Shalev et al.

U.S. application Ser. No. 13/807,880, filed Dec. 31, 2012, which published as US Patent Application Publication 2013/0131783

PCT Application PCT/IL2012/000095, filed Mar. 1, 2012, which published as PCT Publication WO 2012/117395

PCT Application PCT/IL2012/000148, filed Apr. 4, 2012, which published as PCT Publication WO 2013/030818

PCT Application PCT/IL2012/000190, filed May 15, 2012, which published as PCT Publication WO 2013/171730

PCT Application PCT/IL2012/000269, filed Jul. 2, 2012, which published as PCT Publication WO 2013/005207

PCT Application PCT/IL2012/050424, filed Oct. 29, 2012, which published as PCT Publication WO 2013/065040

PCT Application PCT/IL2012/050506, filed Dec. 4, 2012, which published as PCT Publication WO 2013/084235

U.S. Provisional Application 61/749,965, filed Jan. 8, 2013

U.S. Pat. No. 8,951,298 to Shalev

U.S. Provisional Application 61/775,964, filed Mar. 11, 2013

U.S. Provisional Application 61/826,544, filed May 23, 2013

U.S. application Ser. No. 13/979,551, filed Jul. 12, 2013, which published as US Patent Application Publication 2013/0289587

PCT Application PCT/IL2013/050656, filed Jul. 31, 2013, which published as PCT Publication WO 2014/020609

U.S. Provisional Application 61/906,014, filed Nov. 19, 2013

PCT Application PCT/IL2014/050019, filed Jan. 7, 2014, which published as PCT Publication WO 2014/108895

U.S. Provisional Application 61/926,533, filed Jan. 13, 2014

PCT Application PCT/2014/050174, filed Feb. 18, 2014, which published as PCT Publication WO 2014/141232

PCT Application PCT/IL2014/050434, filed May 18, 2014, which published as PCI Publication WO 2014/188412

PCT Application PCT/IL2014/050973, filed Nov. 6, 2014, which published as PCT Publication WO 2015/075708

U.S. Provisional Application 62/093,497, filed Dec. 18, 2014

U.S. Provisional Application 62/102,265, filed Jan. 12, 2015

U.S. application Ser. No. 14/416,236, filed Jan. 21, 2015, which published as US Patent Application Publication 2015/0202065

U.S. Provisional Application 62/110,659, filed Feb. 2, 2015

PCT Application PCT/IL2015/051221, filed Dec. 16, 2015, which published as PCT Publication WO 2016/098113

PCT Application PCT/IL2016/050014, filed Jan. 6, 2016, which published as PCT Publication WO 2016/113731

PCT Application PCT/IL2016/050049, filed Jan. 14, 2016

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An endovascular system comprising:
a delivery sheath; and
an endovascular prosthesis, which (a) is removably disposed in the delivery sheath in a radially-compressed delivery state, (b) is configured to assume a radially-expanded state when unconstrained, (c) comprises structural strut members and a graft member, and (d) comprises:
  a stent-graft, which comprises a first portion of the structural strut members and a first portion of the graft member, wherein the structural strut members of the first portion and the graft member of the first portion are attached to each other and, when the endovascular prosthesis is unconstrained in the radially-expanded state, together are shaped so as to define a blood-carrying tubular structure defining a lumen, wherein the structural strut members of the first portion are arranged in discrete bands that support the blood-carrying tubular structure; and
  an external coagulation inducer, which comprises an extra-luminal skirt, which (a) comprises a second portion of the structural strut members and a second portion of the graft member, and (b) is configured to assume:
    (i) when the endovascular prosthesis is removably disposed in the delivery sheath, a radially-compressed delivery state, in which the structural strut members of the first portion do not coincide with the structural stent members of the second portion, and
    (ii) when the endovascular prosthesis is unconstrained, a radially-expanded state, in which the extra-luminal skirt extends radially outward from an external surface of the stent-graft,
  wherein a set of the structural strut members defines a single generally tubular stent structure that includes both the structural strut members of the extra-luminal skirt and the structural strut members of a single one of the bands, and
  wherein the extra-luminal skirt completely circumferentially encircles the stent-graft.

2. The endovascular system according to claim 1, wherein the extra-luminal skirt monotonically widens along an entire length of the extra-luminal skirt, when the endovascular prosthesis is unconstrained in the radially-expanded state.

3. The endovascular system according to claim 2, wherein the extra-luminal skirt monotonically widens in a distal-to-proximal direction along an entire length of the extra-luminal skirt, when the endovascular prosthesis is unconstrained in the radially-expanded state.

4. The endovascular system according to claim 2, wherein the extra-luminal skirt monotonically widens in a proximal-to-distal direction along an entire length of the extra-luminal skirt, when the endovascular prosthesis is unconstrained in the radially-expanded state.

5. The endovascular system according to claim 1, wherein the stent-graft is a main stent-graft, and wherein the endovascular system further comprises one or more branching stent-grafts.

6. The endovascular system according to claim 1,
wherein the extra-luminal skirt is a first extra-luminal skirt,
wherein the external coagulation inducer further comprises a second extra-luminal skirt, which (a) comprises a third portion of the structural strut members and a third portion of the graft member, and (b) is configured to assume:
  (i) when the endovascular prosthesis is removably disposed in the delivery sheath, a radially-compressed delivery state, in which the structural strut members of the first portion do not coincide with the structural stent members of the third portion, and
  (ii) when the endovascular prosthesis is unconstrained, a radially-expanded state, in which the second extra-luminal skirt extends radially outward from the external surface of the stent-graft,
wherein the set of the structural strut members is a first set of the structural strut members, the single generally tubular stent structure is a first single generally tubular stent structure, and the single one of the bands is a first single one of the bands, and
wherein a second set of the structural strut members defines a second single generally tubular stent structure that includes both the structural strut members of the second extra-luminal skirt and the structural strut members of a second single one of the bands.

7. The endovascular system according to claim 6,
wherein the first extra-luminal skirt is disposed proximally to the second extra-luminal skirt, and
wherein when the endovascular prosthesis is unconstrained in the radially-expanded state:
   the first extra-luminal skirt monotonically widens in a distal-to-proximal direction along an entire length of the first extra-luminal skirt, and
   the second extra-luminal skirt monotonically widens in a proximal-to-distal direction along an entire length of the second extra-luminal skirt.

8. The endovascular system according to claim 1,
wherein the structural strut members of the second portion are directly connected to the structural strut members of the first portion,
wherein none of the structural strut members of the second portion is directly connected to any of the other structural strut members of the second portion, and
wherein none of the structural strut members of the second portion is indirectly stent-connected to any of the other structural strut members of the second portion other than via one or more of the structural strut members of the first portion.

9. An endovascular system comprising:
a delivery sheath; and
an endovascular prosthesis, which (a) is removably disposed in the delivery sheath in a radially-compressed delivery state, (b) is configured to assume a radially-expanded state when unconstrained, (c) comprises structural strut members and a graft member, and (d) comprises:
   a stent-graft, which comprises a first portion of the structural strut members and a first portion of the graft member, wherein the structural strut members of the first portion and the graft member of the first portion are attached to each other and, when the endovascular prosthesis is unconstrained in the radially-expanded state, together are shaped so as to define a blood-carrying tubular structure defining a lumen, wherein the structural strut members of the first portion are arranged in discrete bands that support the blood-carrying tubular structure; and
   an external coagulation inducer, which comprises an extra-luminal skirt, which (a) comprises a second portion of the structural strut members and a second portion of the graft member, and (b) is configured to assume:
      (i) when the endovascular prosthesis is removably disposed in the delivery sheath, a radially-compressed delivery state, in which the structural strut members of the first portion do not coincide with the structural stent members of the second portion, and
      (ii) when the endovascular prosthesis is unconstrained, a radially-expanded state, in which the extra-luminal skirt extends radially outward from an external surface of the stent-graft,
wherein a set of the structural strut members defines a single generally tubular stent structure that includes both the structural strut members of the extra-luminal skirt and the structural strut members of a single one of the bands, and
wherein when the endovascular prosthesis is unconstrained in the radially-expanded state, the structural strut members of the second portion extend radially outward from the external surface of the stent-graft at an angle of between 30 and 40 degrees with the external surface.

10. The endovascular system according to claim 9, wherein the extra-luminal skirt completely circumferentially encircles the stent-graft.

11. An endovascular system comprising:
a delivery sheath; and
an endovascular prosthesis, which (a) is removably disposed in the delivery sheath in a radially-compressed delivery state, (b) is configured to assume a radially-expanded state when unconstrained, (c) comprises structural strut members and a graft member, and (d) comprises:
   a stent-graft, which comprises a first portion of the structural strut members and a first portion of the graft member, wherein the structural strut members of the first portion and the graft member of the first portion are attached to each other and, when the endovascular prosthesis is unconstrained in the radially-expanded state, together are shaped so as to define a blood-carrying tubular structure defining a lumen, wherein the structural strut members of the first portion are arranged in discrete bands that support the blood-carrying tubular structure; and
   an external coagulation inducer, which comprises an extra-luminal skirt, which (a) comprises a second portion of the structural strut members and a second portion of the graft member, and (b) is configured to assume:
      (i) when the endovascular prosthesis is removably disposed in the delivery sheath, a radially-compressed delivery state, in which the structural strut members of the first portion do not coincide with the structural stent members of the second portion, and
      (ii) when the endovascular prosthesis is unconstrained, a radially-expanded state, in which the extra-luminal skirt extends radially outward from an external surface of the stent-graft,
wherein a set of the structural strut members defines a single generally tubular stent structure that includes both the structural strut members of the extra-luminal skirt and the structural strut members of a single one of the bands, and
wherein a greatest external perimeter of the extra-luminal skirt equals at least 110% of a greatest external perimeter of the stent-graft, when the endovascular prosthesis is unconstrained in the radially-expanded state.

12. An endovascular system comprising:
a delivery sheath; and
an endovascular prosthesis, which (a) is removably disposed in the delivery sheath in a radially-compressed delivery state, (b) is configured to assume a radially-expanded state when unconstrained, (c) comprises structural strut members and a graft member, and (d) comprises:
   a stent-graft, which comprises a first portion of the structural strut members and a first portion of the graft member, wherein the structural strut members of the first portion and the graft member of the first portion are attached to each other and, when the endovascular prosthesis is unconstrained in the radially-expanded state, together are shaped so as to define a blood-carrying tubular structure defining a lumen, wherein the structural strut members of the first portion are arranged in discrete bands that support the blood-carrying tubular structure; and an external coagulation inducer, which comprises an extra-luminal skirt, which (a) comprises a second portion of the structural strut members and a second portion of the graft member, and (b) is configured to assume:
  (i) when the endovascular prosthesis is removably disposed in the delivery sheath, a radially-compressed delivery state, in which the structural strut members of the first portion do not coincide with the structural stent members of the second portion, and
  (ii) when the endovascular prosthesis is unconstrained, a radially-expanded state, in which the extra-luminal skirt extends radially outward from an external surface of the stent-graft, wherein a set of the structural strut members defines a single generally tubular stent structure that includes both the structural strut members of the extra-luminal skirt and the structural strut members of a single one of the bands, wherein the extra-luminal skirt is a first extra-luminal skirt, wherein the external coagulation inducer further comprises a second extra-luminal skirt, which (a) comprises a third portion of the structural strut members and a third portion of the graft member, and (b) is configured to assume:
  (i) when the endovascular prosthesis is removably disposed in the delivery sheath, a radially-compressed delivery state, in which the structural strut members of the first portion do not coincide with the structural stent members of the third portion, and
  (ii) when the endovascular prosthesis is unconstrained, a radially-expanded state, in which the second extra-luminal skirt extends radially outward from the external surface of the stent-graft, wherein the set of the structural strut members is a first set of the structural strut members, the single generally tubular stent structure is a first single generally tubular stent structure, and the single one of the bands is a first single one of the bands, and wherein a second set of the structural strut members defines a second single generally tubular stent structure that includes both the structural strut members of the second extra-luminal skirt and the structural strut members of a second single one of the bands, wherein the first extra-luminal skirt is disposed proximally to the second extra-luminal skirt, and wherein when the endovascular prosthesis is unconstrained in the radially-expanded state:
  the first extra-luminal skirt monotonically widens in a distal-to-proximal direction along an entire length of the first extra-luminal skirt, and
  the second extra-luminal skirt monotonically widens in the distal-to-proximal direction along an entire length of the second extra-luminal skirt.

13. An endovascular system comprising:
a delivery sheath; and
an endovascular prosthesis, which (a) is removably disposed in the delivery sheath in a radially-compressed delivery state, (b) is configured to assume a radially-expanded state when unconstrained, (c) comprises structural strut members and a graft member, and (d) comprises:
  a stent-graft, which comprises a first portion of the structural strut members and a first portion of the graft member, wherein the structural strut members of the first portion and the graft member of the first portion are attached to each other and, when the endovascular prosthesis is unconstrained in the radially-expanded state, together are shaped so as to define a blood-carrying tubular structure defining a lumen, wherein the structural strut members of the first portion are arranged in discrete bands that support the blood-carrying tubular structure; and
  an external coagulation inducer, which comprises an extra-luminal skirt, which (a) comprises a second portion of the structural strut members and a second portion of the graft member, and (b) is configured to assume:
    (i) when the endovascular prosthesis is removably disposed in the delivery sheath, a radially-compressed delivery state, in which the structural strut members of the first portion do not coincide with the structural stent members of the second portion, and
    (ii) when the endovascular prosthesis is unconstrained, a radially-expanded state, in which the extra-luminal skirt extends radially outward from an external surface of the stent-graft, wherein a set of the structural strut members defines a single generally tubular stent structure that includes both the structural strut members of the extra-luminal skirt and the structural strut members of a single one of the bands, wherein the structural strut members of the second portion are thinner on average than the structural strut members of the first portion.

14. An endovascular system comprising:
a delivery sheath; and
an endovascular prosthesis, which (a) is removably disposed in the delivery sheath in a radially-compressed delivery state, (b) is configured to assume a radially-expanded state when unconstrained, (c) comprises structural strut members and a graft member, and (d) comprises:
  a stent-graft, which comprises a first portion of the structural strut members and a first portion of the graft member, wherein the structural strut members of the first portion and the graft member of the first portion are attached to each other and, when the endovascular prosthesis is unconstrained in the radially-expanded state, together are shaped so as to define a blood-carrying tubular structure defining a lumen, wherein the structural strut members of the first portion are arranged in discrete bands that support the blood-carrying tubular structure; and
  an external coagulation inducer, which comprises an extra-luminal skirt, which (a) comprises a second portion of the structural strut members and a second portion of the graft member, and (b) is configured to assume:
    (i) when the endovascular prosthesis is removably disposed in the delivery sheath, a radially-compressed delivery state, in which the structural strut members of the first portion do not coincide with the structural stent members of the second portion, and (ii) when the endovascular prosthesis is unconstrained, a radially-expanded state, in which the extra-luminal skirt extends radially outward from an external surface of the stent-graft, wherein a set of the structural strut members defines a single generally tubular stent structure that includes both the structural strut members of the extra-luminal skirt and the structural strut members of a single one of the bands, and wherein the extra-luminal skirt adds less than 30% to a diameter of the stent-graft when the endovascular prosthesis is removably disposed in the delivery sheath in the radially-compressed delivery state.

15. The endovascular system according to claim 14, wherein the extra-luminal skirt adds less than 20% to the diameter of the stent-graft when the endovascular prosthesis is removably disposed in the delivery sheath in the radially-compressed delivery state.

16. A method comprising:
advancing, into a main artery of a subject, an endovascular prosthesis, which is removably disposed in a delivery sheath in a radially-compressed delivery state, and includes (a) structural strut members and a graft member, (b) a main stent-graft, which includes a first portion of the structural strut members and a first portion of the graft member, wherein the structural strut members of the first portion and the graft member of the first portion are attached to each other, and (c) an external coagulation inducer, which includes an extra-luminal skirt, which includes a second portion of the structural strut members and a second portion of the graft member, wherein, when the endovascular prosthesis is removably disposed in the delivery sheath, the external coagulation inducer assumes a radially-compressed delivery state, in which the structural strut members of the first portion do not coincide with the structural stent members of the second portion; and deploying the endovascular prosthesis from the delivery sheath such that (a) the endovascular prosthesis assumes a radially-expanded state in which the first portion of the structural strut members and the first portion of the graft member together are shaped so as to define a blood-carrying tubular structure defining a lumen, wherein the structural strut members of the first portion are arranged in discrete bands that support the blood-carrying tubular structure, and (b) the extra-luminal skirt assumes a radially-expanded state, in which the extra-luminal skirt extends radially outward from an external surface of the stent-graft, wherein a set of the structural strut members defines a single generally tubular stent structure that includes both the structural strut members of the extra-luminal skirt and the structural strut members of a single one of the bands, wherein some of the structural strut members of the second portion axially overlap the structural strut members of the first portion.

17. The method according to claim 16, further comprising deploying one or more branching stent-grafts partially alongside the main stent-graft and partially in respective branching arteries that branch from the main artery, such that portions of the branching stent-grafts contact the extra-luminal skirt.

18. The method according to claim 16,
wherein the structural strut members of the second portion are directly connected to the structural strut members of the first portion,
wherein none of the structural strut members of the second portion is directly connected to any of the other structural strut members of the second portion, and
wherein none of the structural strut members of the second portion is indirectly stent-connected to any of the other structural strut members of the second portion other than via one or more of the structural strut members of the first portion.

\* \* \* \* \*